United States Patent [19]
Yoon

[11] Patent Number: 5,921,993
[45] Date of Patent: Jul. 13, 1999

[54] METHODS OF ENDOSCOPIC TUBAL LIGATION

[76] Inventor: InBae Yoon, 2101 Highland Ridge Dr., Phoenix, Md. 21131

[21] Appl. No.: 08/847,186

[22] Filed: May 1, 1997

[51] Int. Cl.[6] .................................................. A61B 17/04
[52] U.S. Cl. ........................ 606/140; 606/139; 606/141; 606/148
[58] Field of Search .................... 606/139, 144, 606/147, 145, 146, 141, 148

[56] References Cited

U.S. PATENT DOCUMENTS

| | | |
|---|---|---|
| 1,916,722 | 7/1933 | Ende . |
| 2,012,776 | 5/1932 | Roeder ..................... 606/144 |
| 2,162,297 | 4/1941 | Southerland et al. . |
| 2,227,270 | 1/1939 | Moore . |
| 2,610,631 | 11/1949 | Calicchio . |
| 2,856,933 | 10/1958 | Hilbebrand et al. . |
| 3,033,204 | 5/1958 | Wood . |
| 3,870,048 | 3/1975 | Yoon . |
| 3,871,379 | 3/1975 | Clarke . |
| 3,911,923 | 10/1975 | Yoon ..................... 606/144 |
| 3,967,625 | 7/1976 | Yoon ..................... 606/144 |
| 3,985,138 | 10/1976 | Jarvik ..................... 606/144 |
| 3,989,049 | 11/1976 | Yoon ..................... 606/144 |
| 4,018,229 | 4/1977 | Komiya ..................... 606/144 |
| 4,085,743 | 4/1978 | Yoon ..................... 606/144 |
| 4,103,680 | 8/1978 | Yoon ..................... 606/144 |
| 4,177,813 | 12/1979 | Miller et al. . |
| 4,230,116 | 10/1980 | Watson . |
| 4,374,523 | 2/1983 | Yoon . |
| 4,471,766 | 9/1984 | Terayama . |
| 4,478,221 | 10/1984 | Heiss . |
| 4,773,420 | 9/1988 | Green . |
| 4,890,615 | 1/1990 | Caspari et al. . |
| 4,935,027 | 6/1990 | Yoon ..................... 606/144 |
| 5,037,433 | 8/1991 | Wilk et al. . |
| 5,100,415 | 3/1992 | Hayhurst . |
| 5,144,961 | 9/1992 | Chen et al. . |
| 5,147,373 | 9/1992 | Ferzli . |
| 5,163,942 | 11/1992 | Rydell . |
| 5,181,919 | 1/1993 | Bergman et al. . |
| 5,196,022 | 3/1993 | Bilweis . |
| 5,217,030 | 6/1993 | Yoon . |
| 5,234,443 | 8/1993 | Phan et al. . |
| 5,236,434 | 8/1993 | Callicrate . |
| 5,242,459 | 9/1993 | Buelna . |
| 5,257,637 | 11/1993 | El Gazayerli . |
| 5,281,236 | 1/1994 | Bagnato et al. . |
| 5,281,238 | 1/1994 | Chin et al. . |
| 5,282,809 | 2/1994 | Kammerer et al. ..................... 606/144 |
| 5,290,284 | 3/1994 | Adair . |
| 5,300,078 | 4/1994 | Buelna . |
| 5,312,423 | 5/1994 | Rosenbluth et al. . |

(List continued on next page.)

FOREIGN PATENT DOCUMENTS

| | | |
|---|---|---|
| 0477020 | 3/1992 | European Pat. Off. . |
| 509640 | 10/1930 | Germany . |

OTHER PUBLICATIONS

PortSaver® PercLoop® , Advanced Surgical, Inc., 305 College Road East, Princeton, NJ 08540.

"Laparoscopic Suturing and Ligation Techniques", Resad Pasic, M.D., Ph.D., and Ronald L.Levine, M.D., The Journal of the American Association of Gynecologic Laparoscopists, Nov., 1995, vol. 3, No. 1.

*Primary Examiner*—Gary Jackson
*Attorney, Agent, or Firm*—Blank Rome Comisky & McCauley LLP

[57] ABSTRACT

A method of endoscopic tubal ligation includes the steps of introducing a distal end of an instrument assembly at an internal operative site through a small size port, visualizing the internal operative site with an endoscope from externally of the internal operative site, grasping an anatomical tubular structure at the internal operative site with a grasping member of the instrument assembly and drawing the anatomical tubular structure into a loop formation and contracting a ligature loop of filamentous ligature material of the instrument assembly around the loop formation to form a ligature without withdrawing the instrument assembly from the internal operative site.

26 Claims, 23 Drawing Sheets

U.S. PATENT DOCUMENTS

| | | |
|---|---|---|
| 5,334,199 | 8/1994 | Yoon . |
| 5,403,330 | 4/1995 | Tuason . |
| 5,405,351 | 4/1995 | Kinet et al. . |
| 5,417,684 | 5/1995 | Jackson et al. . |
| 5,466,241 | 11/1995 | Leroy et al. . |
| 5,486,186 | 1/1996 | Yoon ........................................ 606/144 |
| 5,571,120 | 11/1996 | Yoon ........................................ 606/144 |
| 5,722,990 | 3/1998 | Sugarbaker et al. .................... 606/207 |
| 5,788,716 | 8/1998 | Kobren et al. .......................... 606/141 |
| 5,810,805 | 9/1998 | Sutcu et al. .............................. 606/45 |

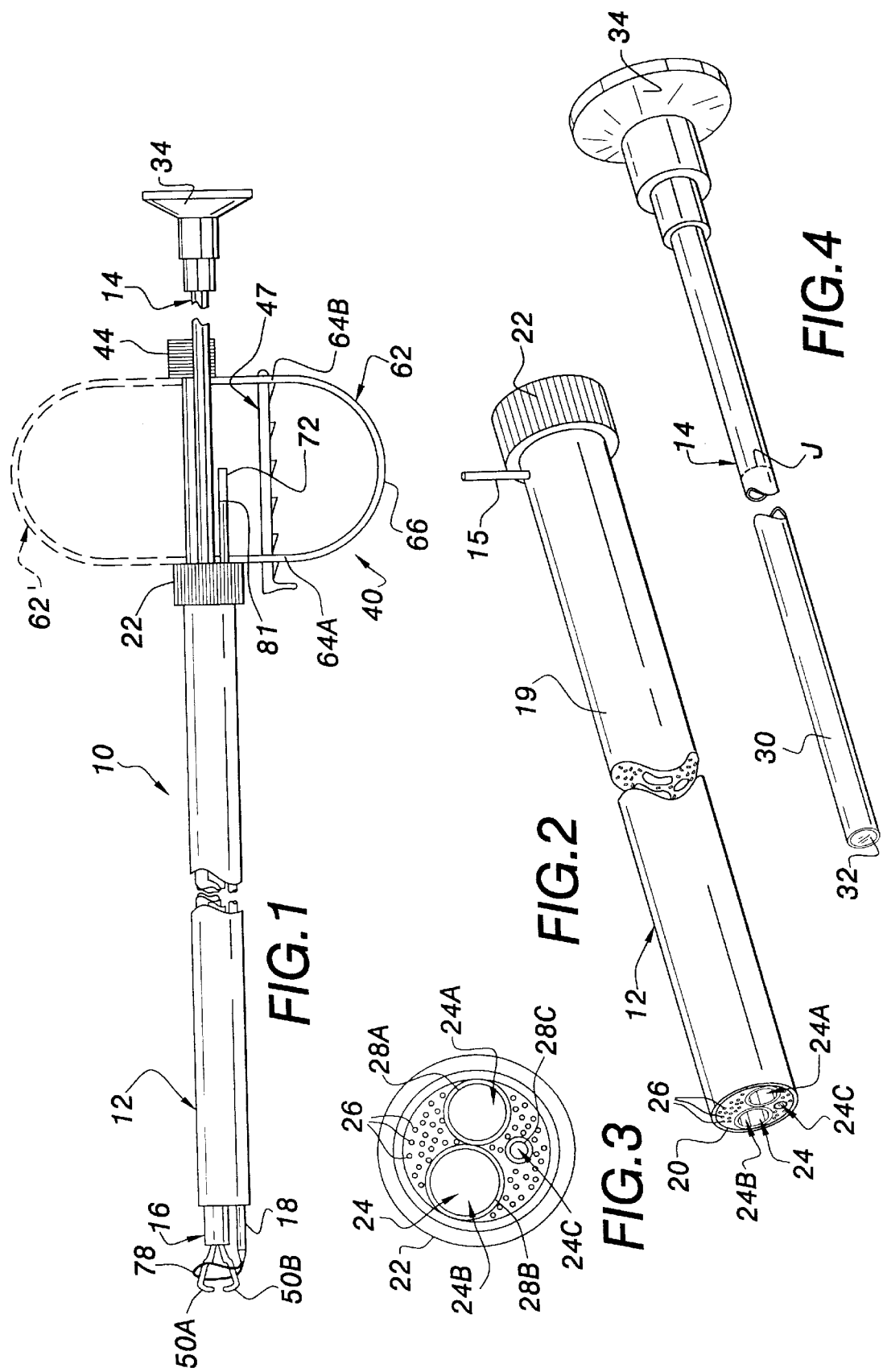

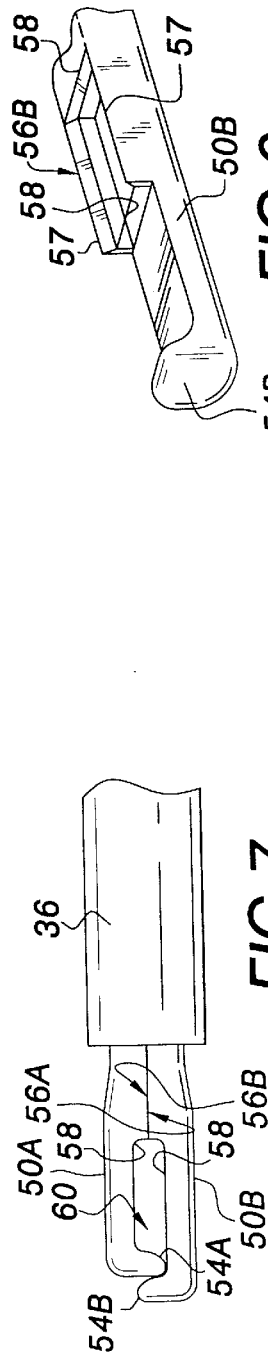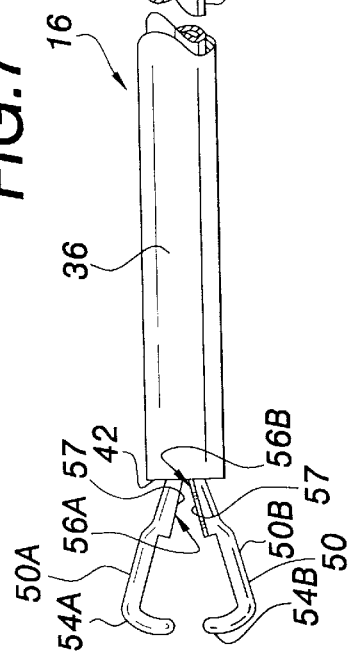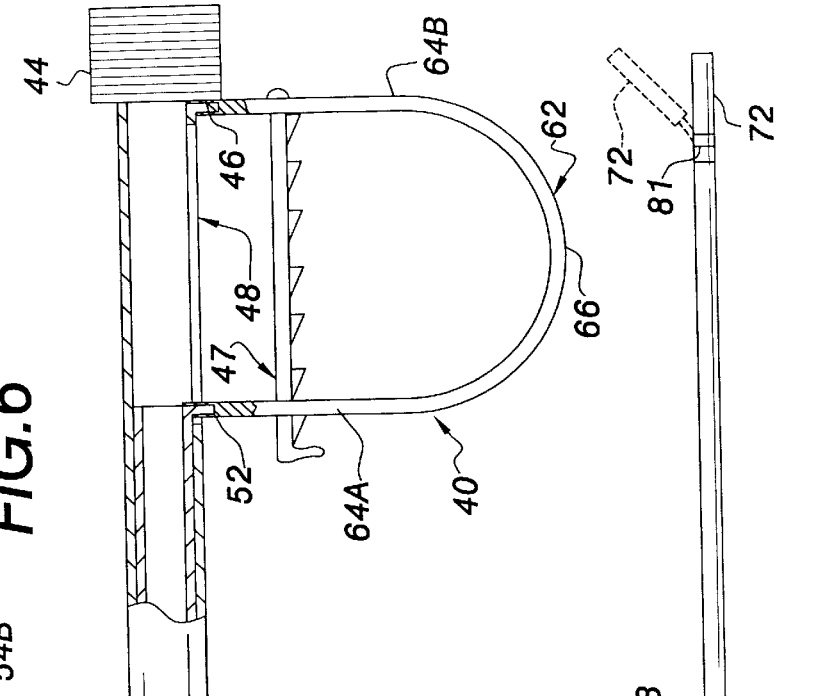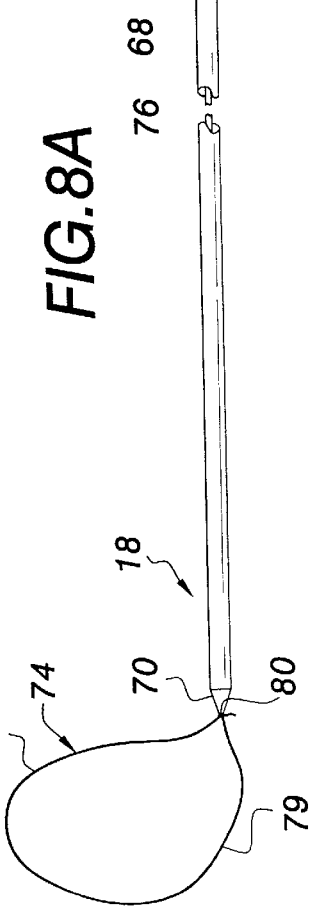

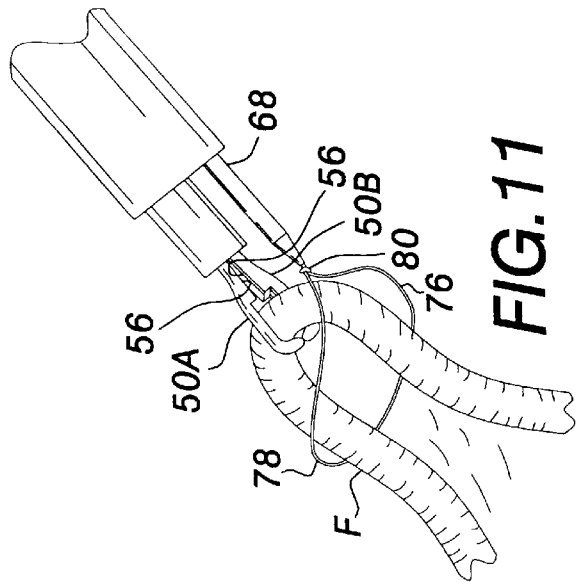
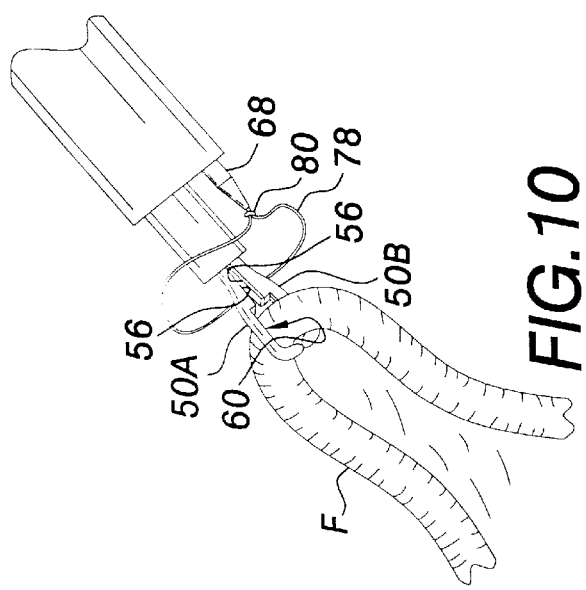
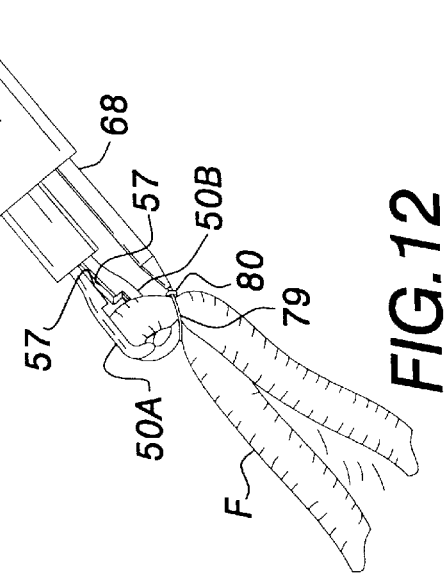
FIG. 10
FIG. 11
FIG. 12

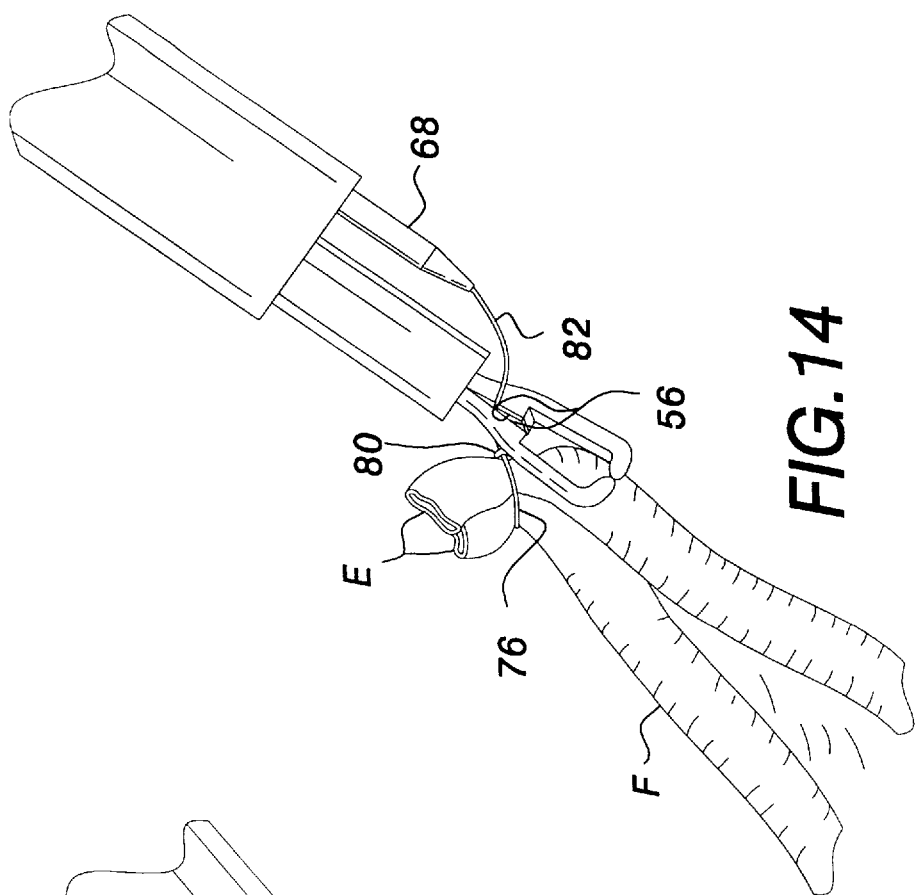
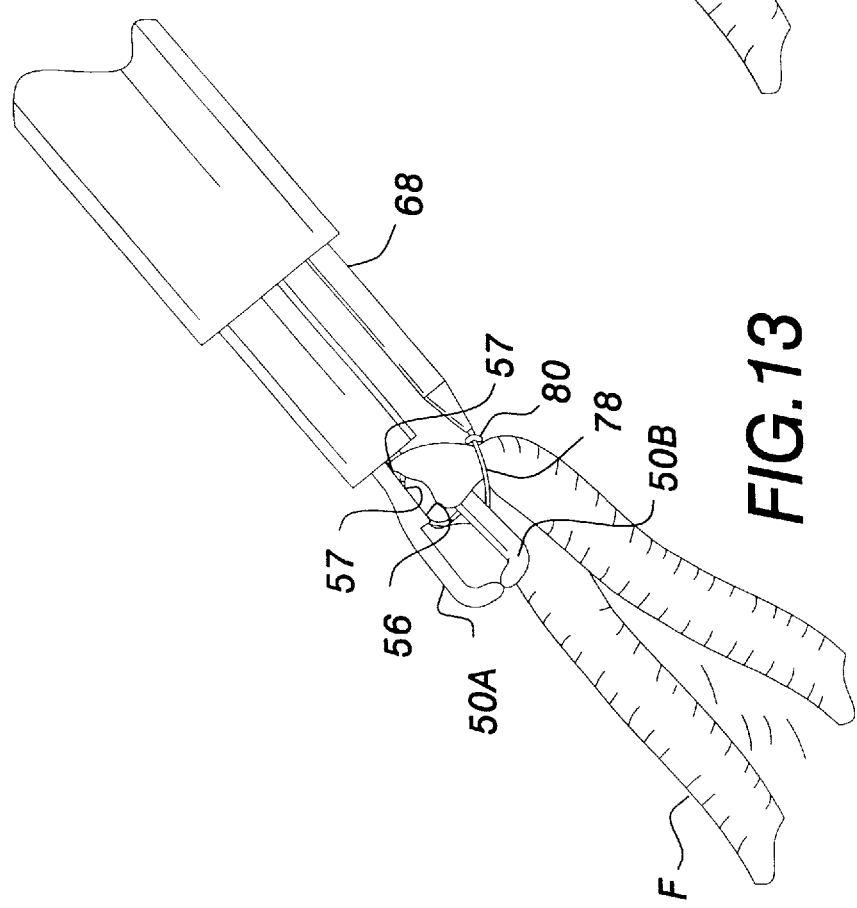

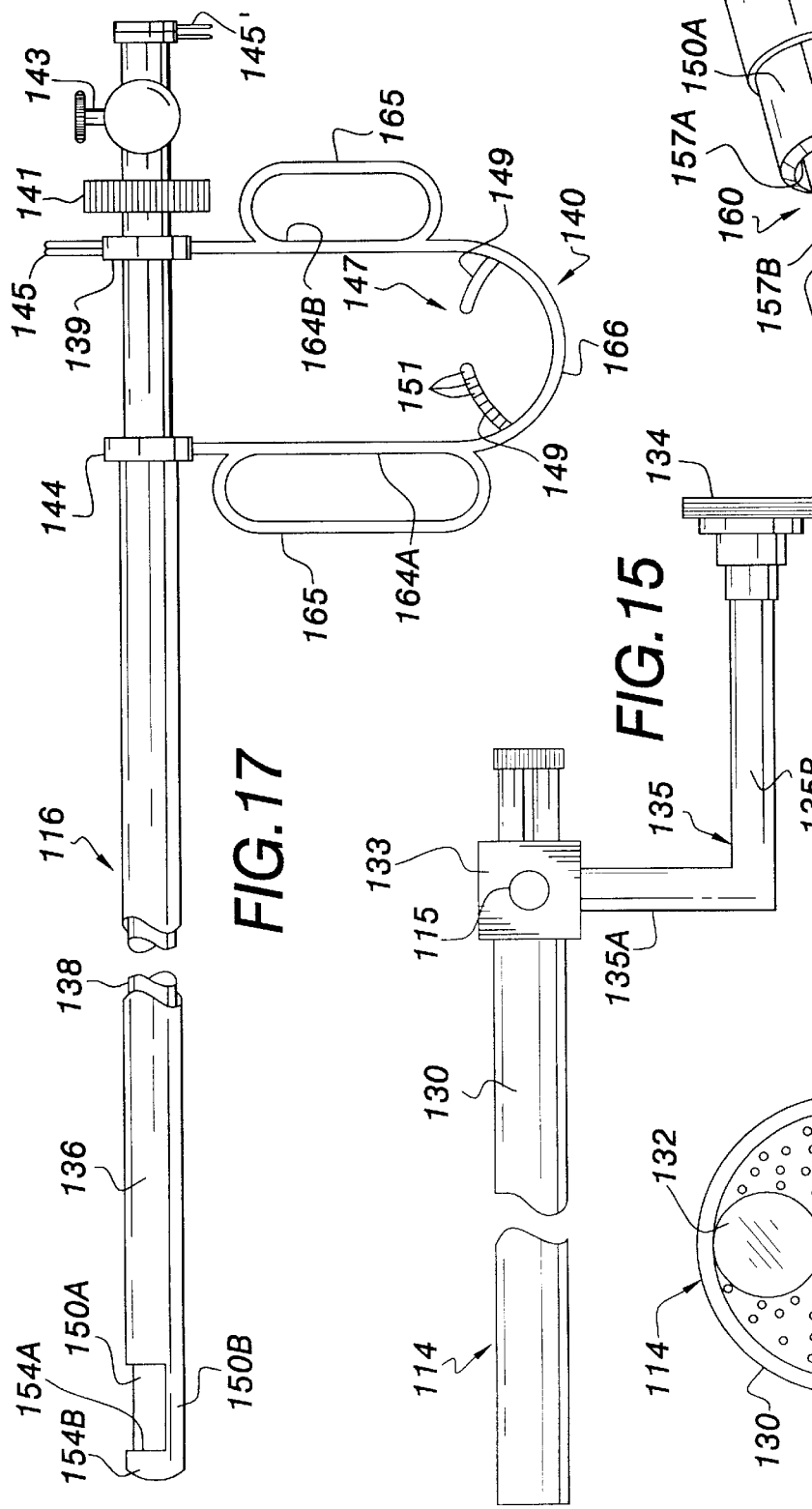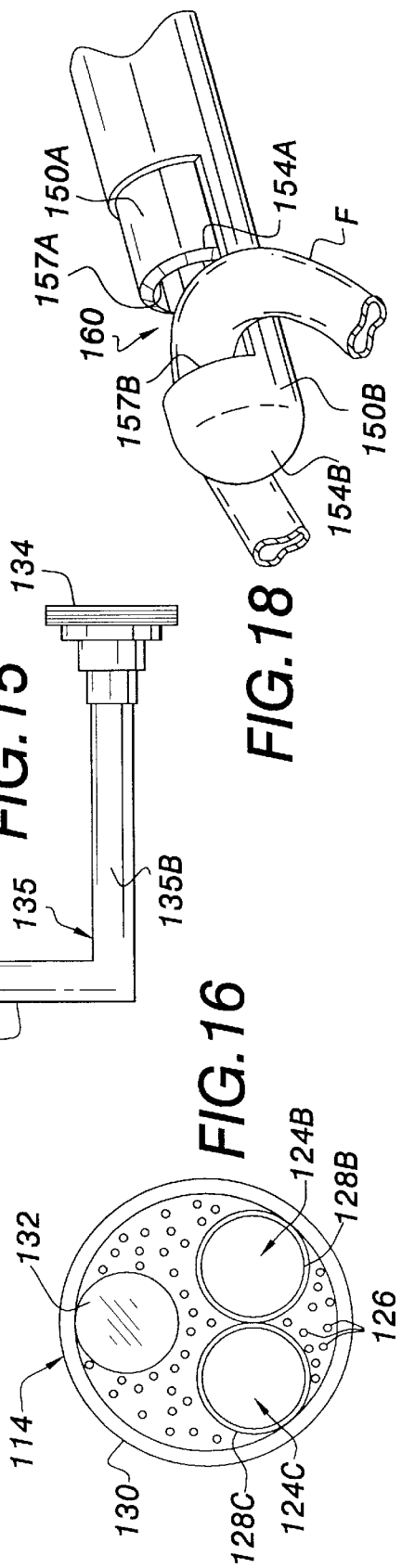

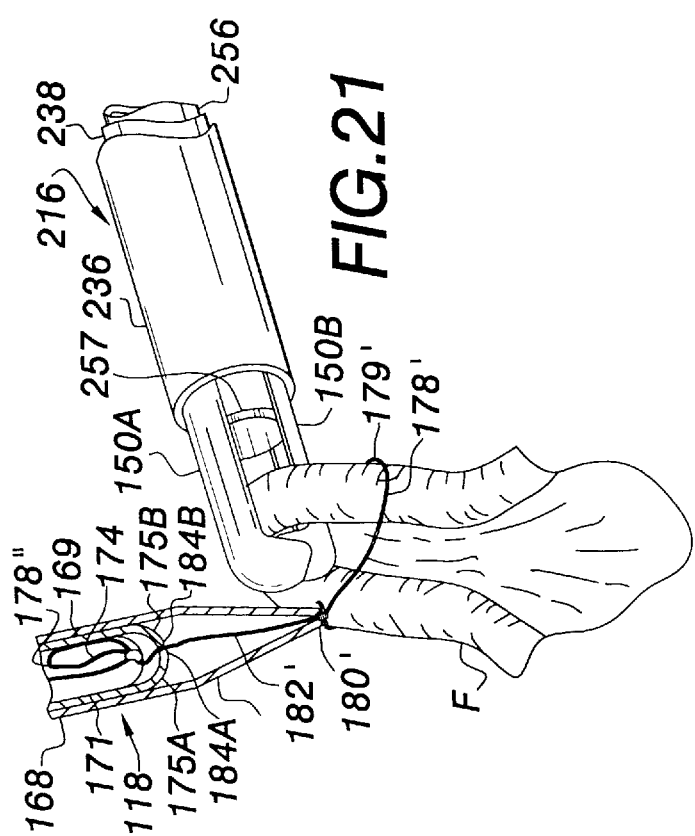
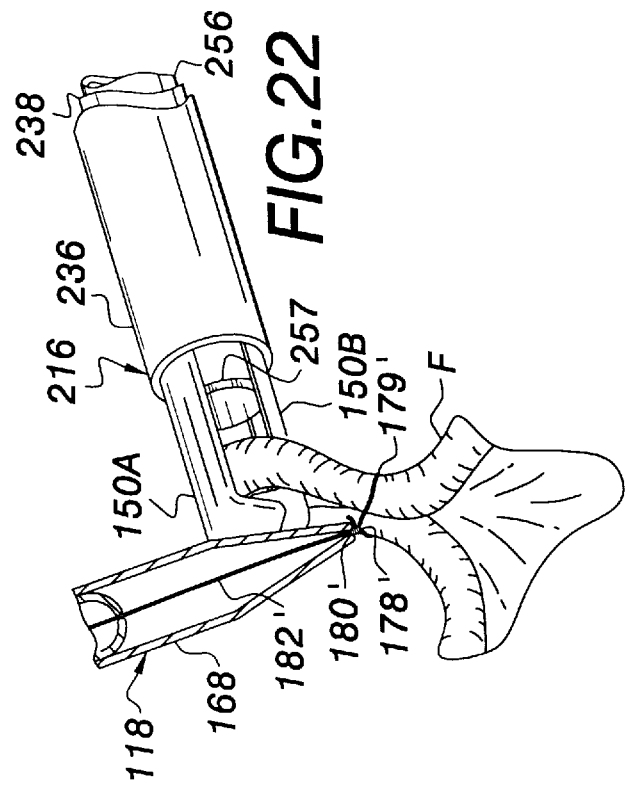

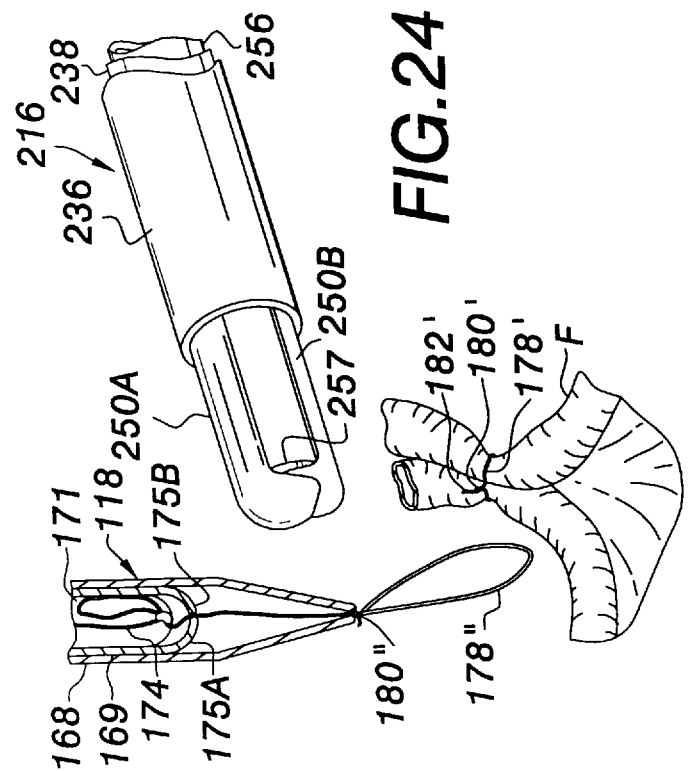
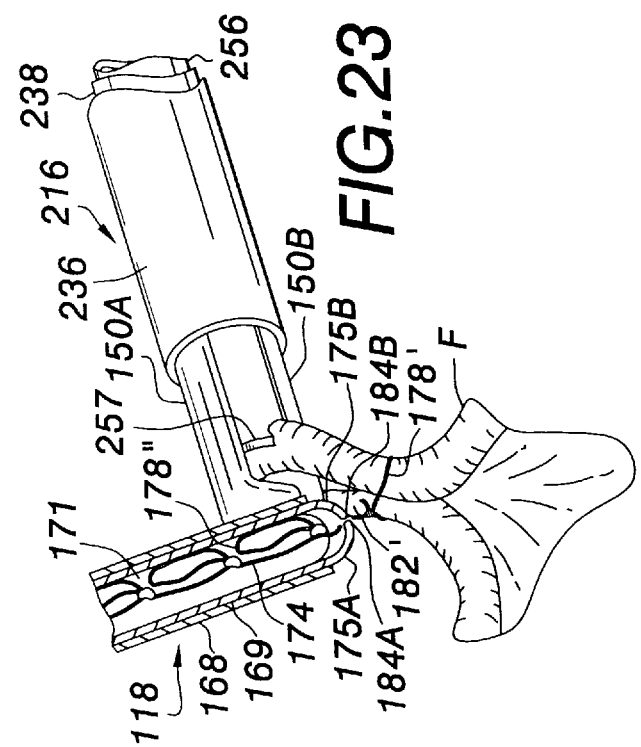

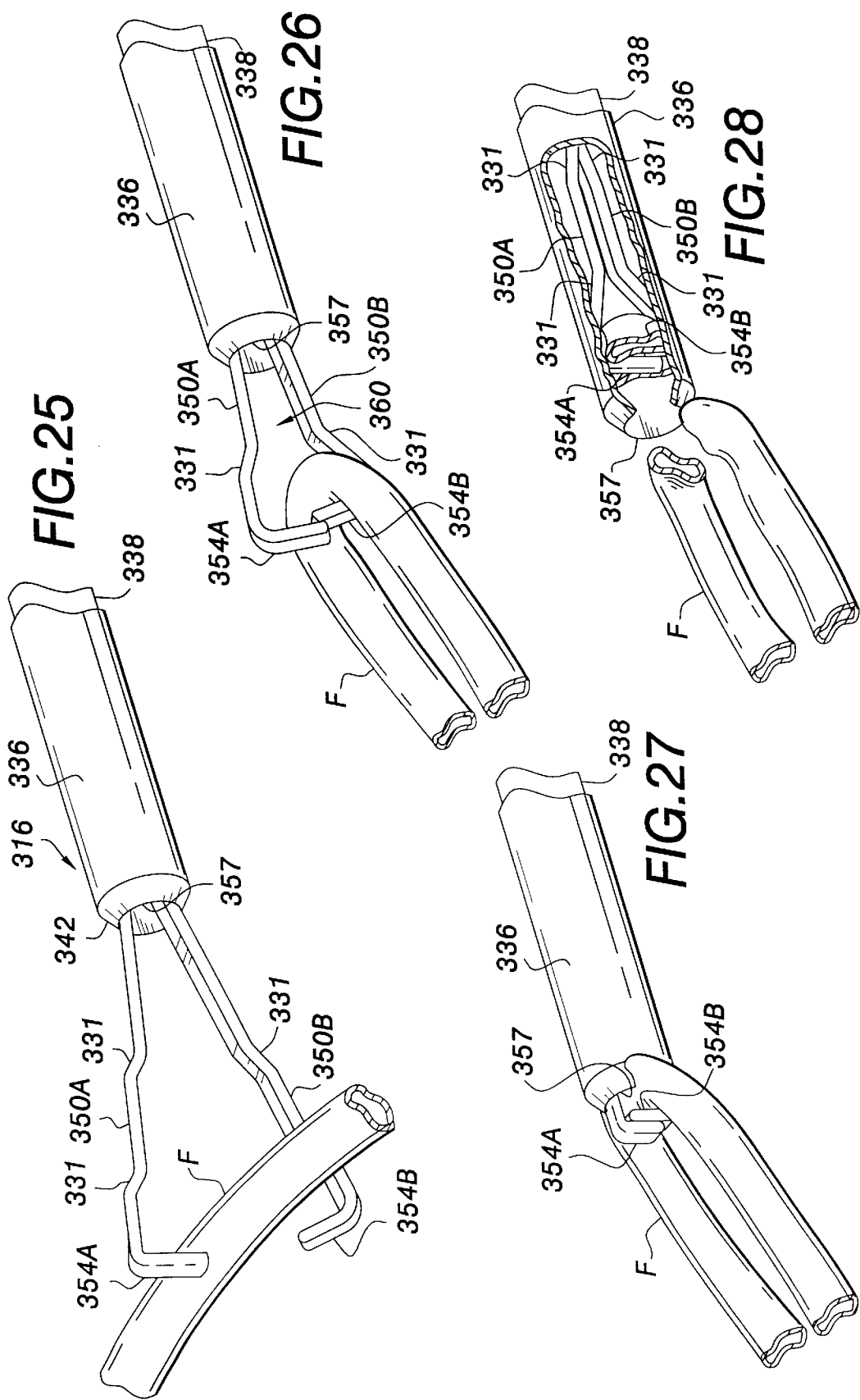

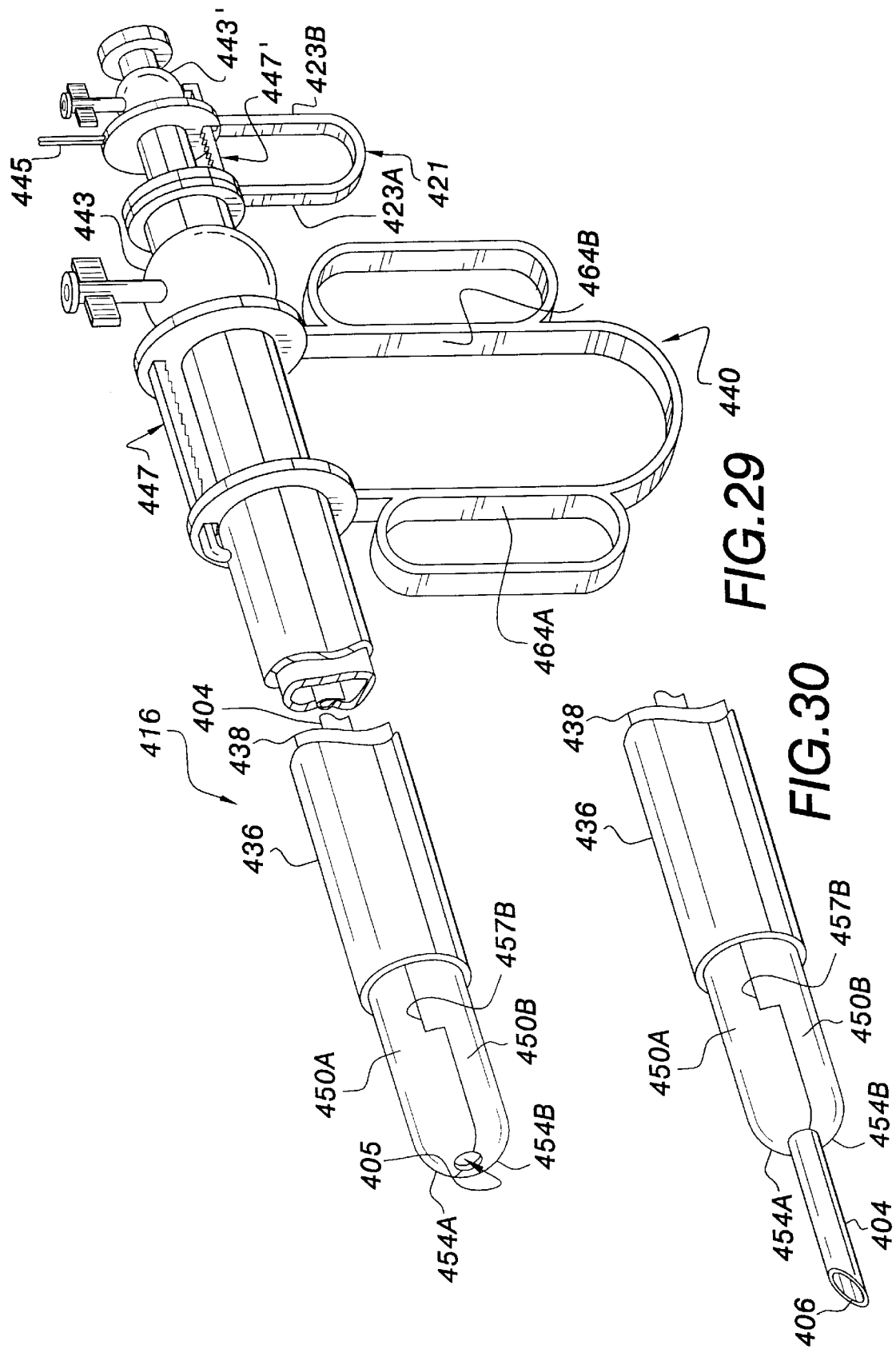

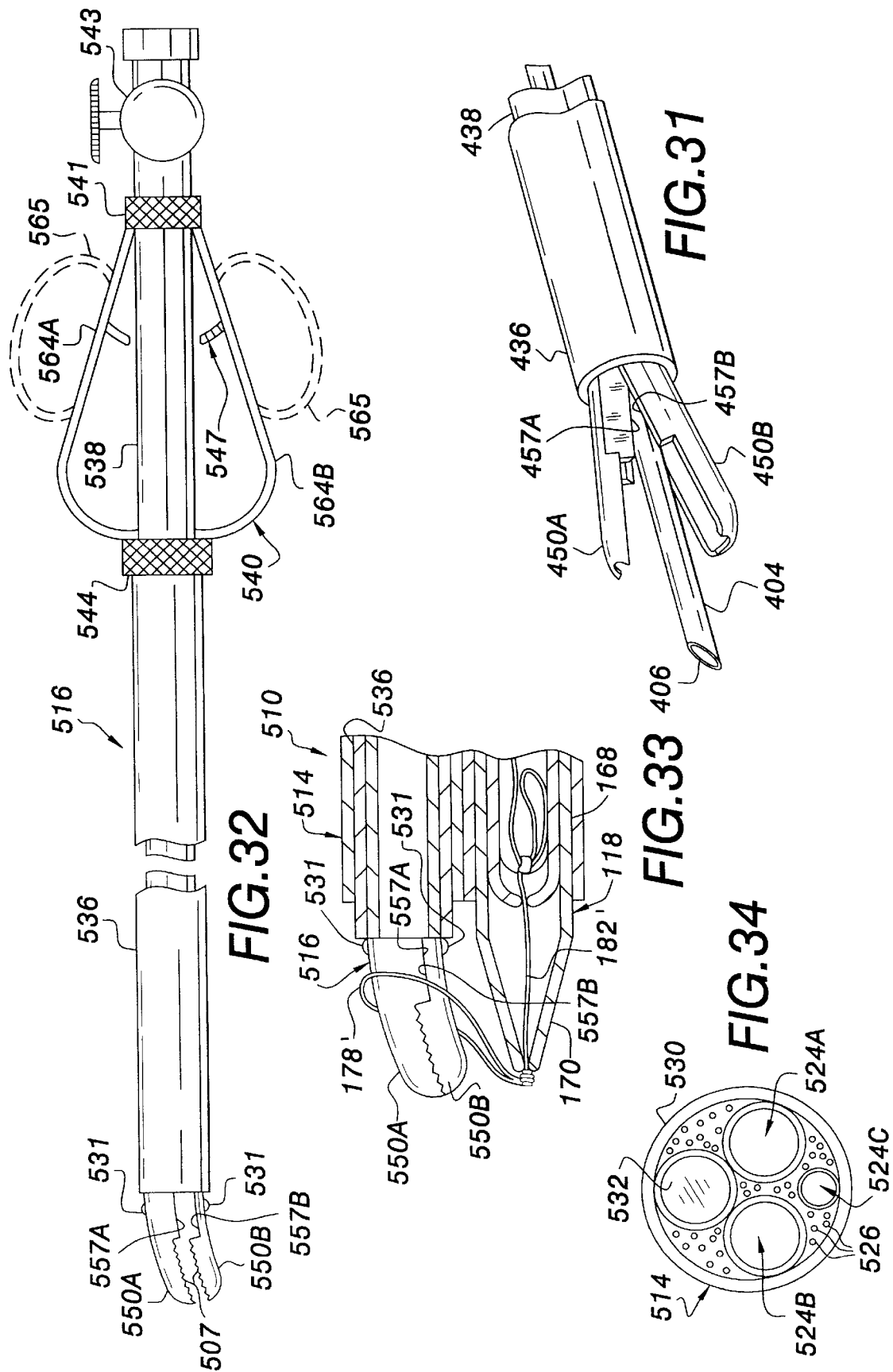

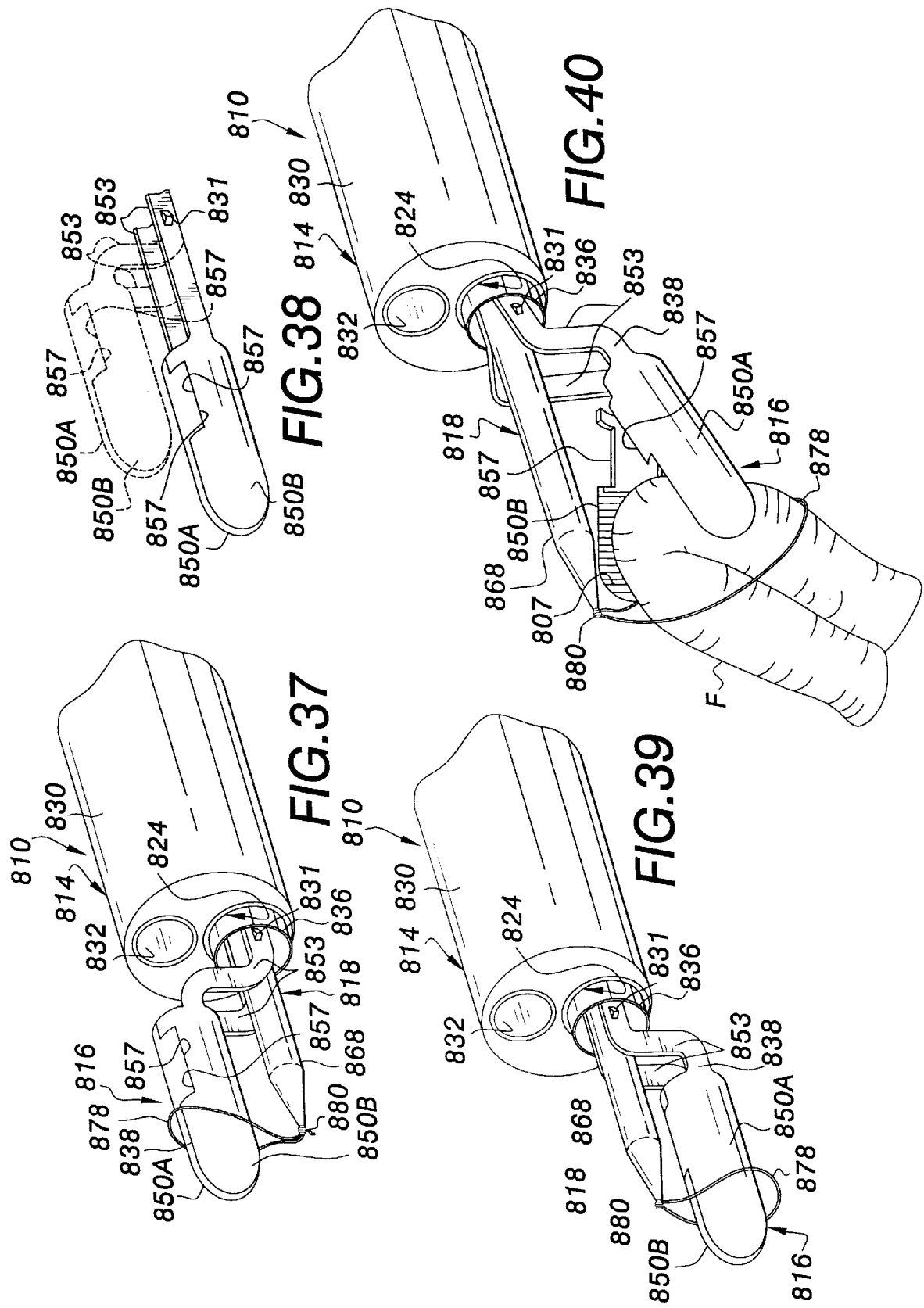

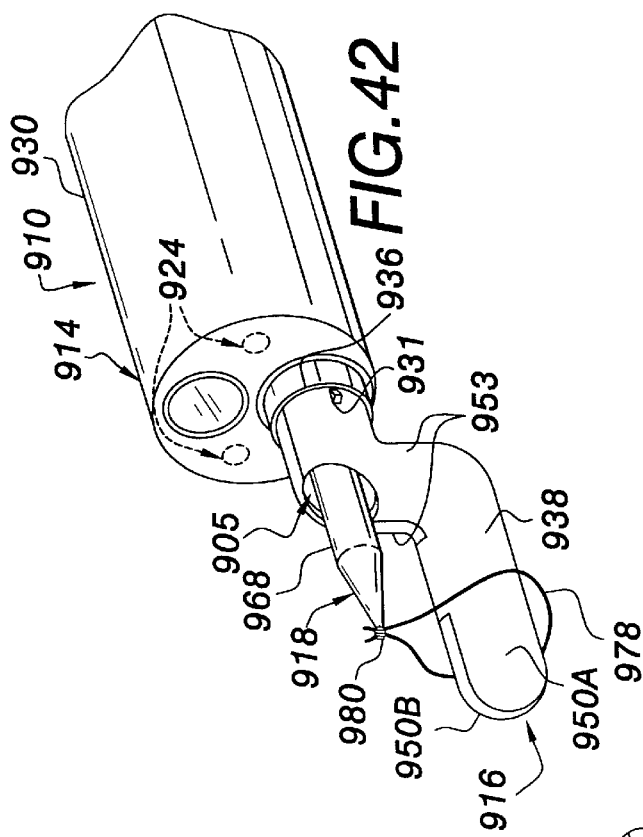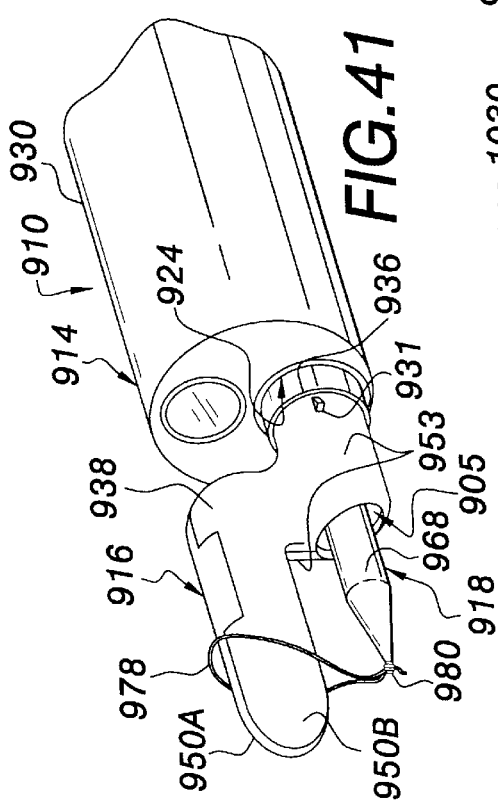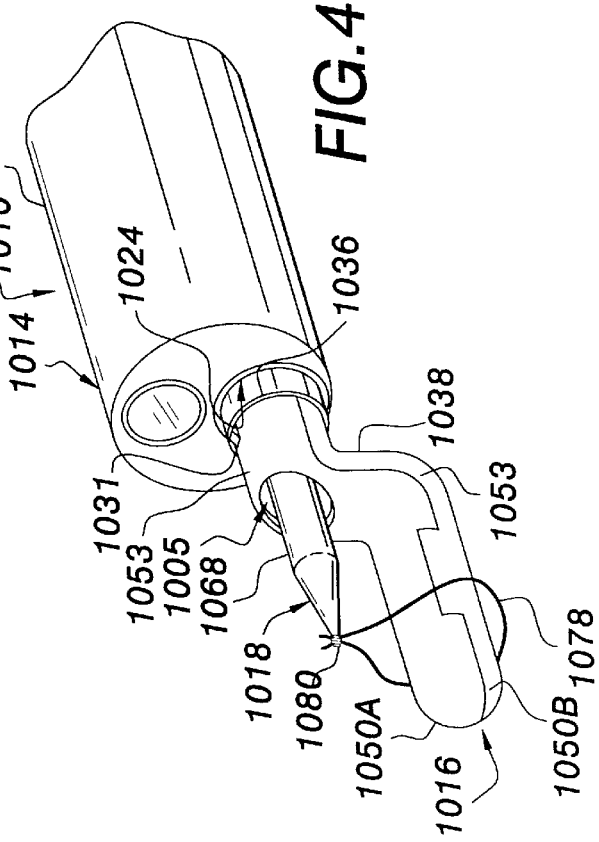

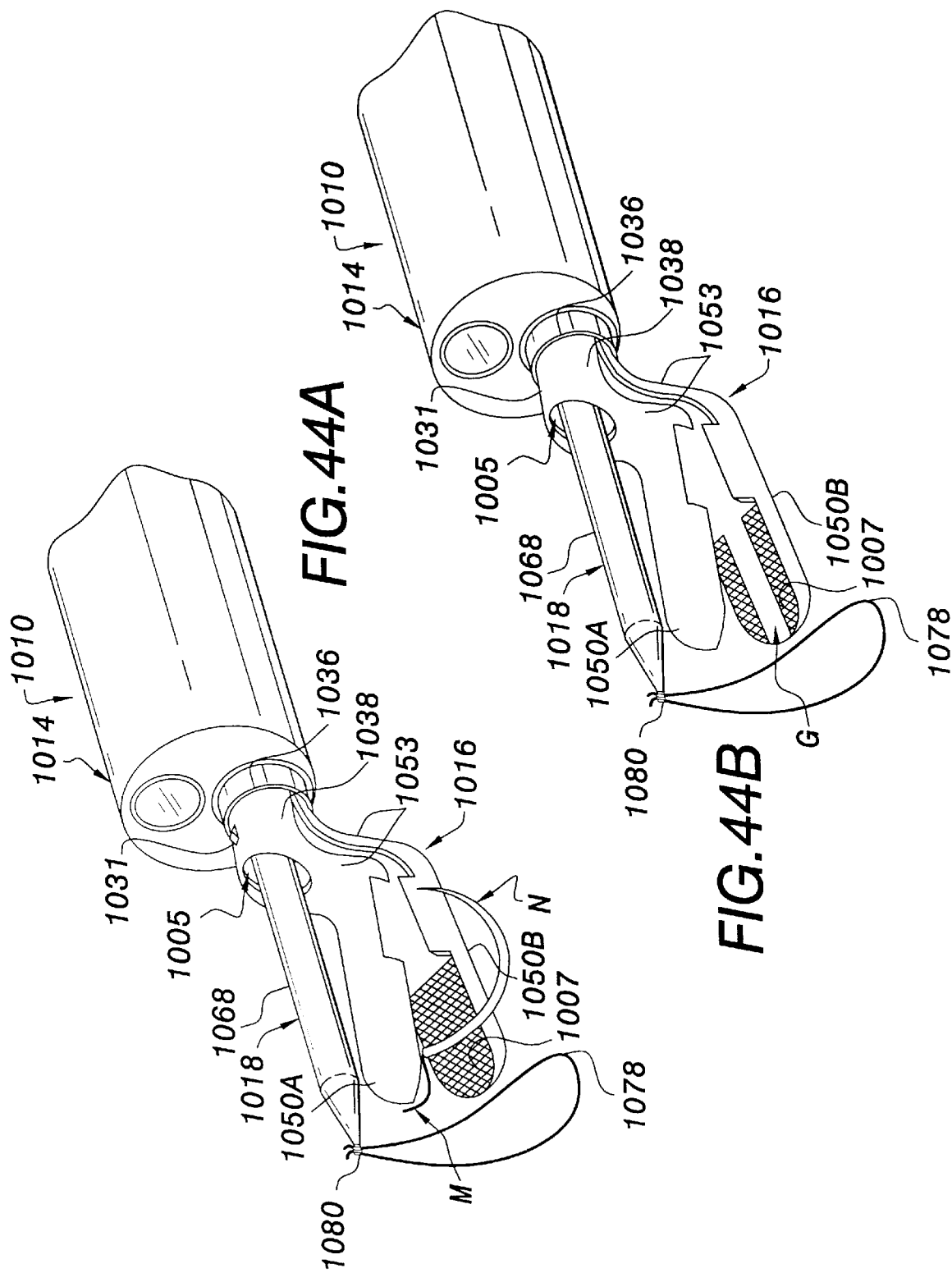

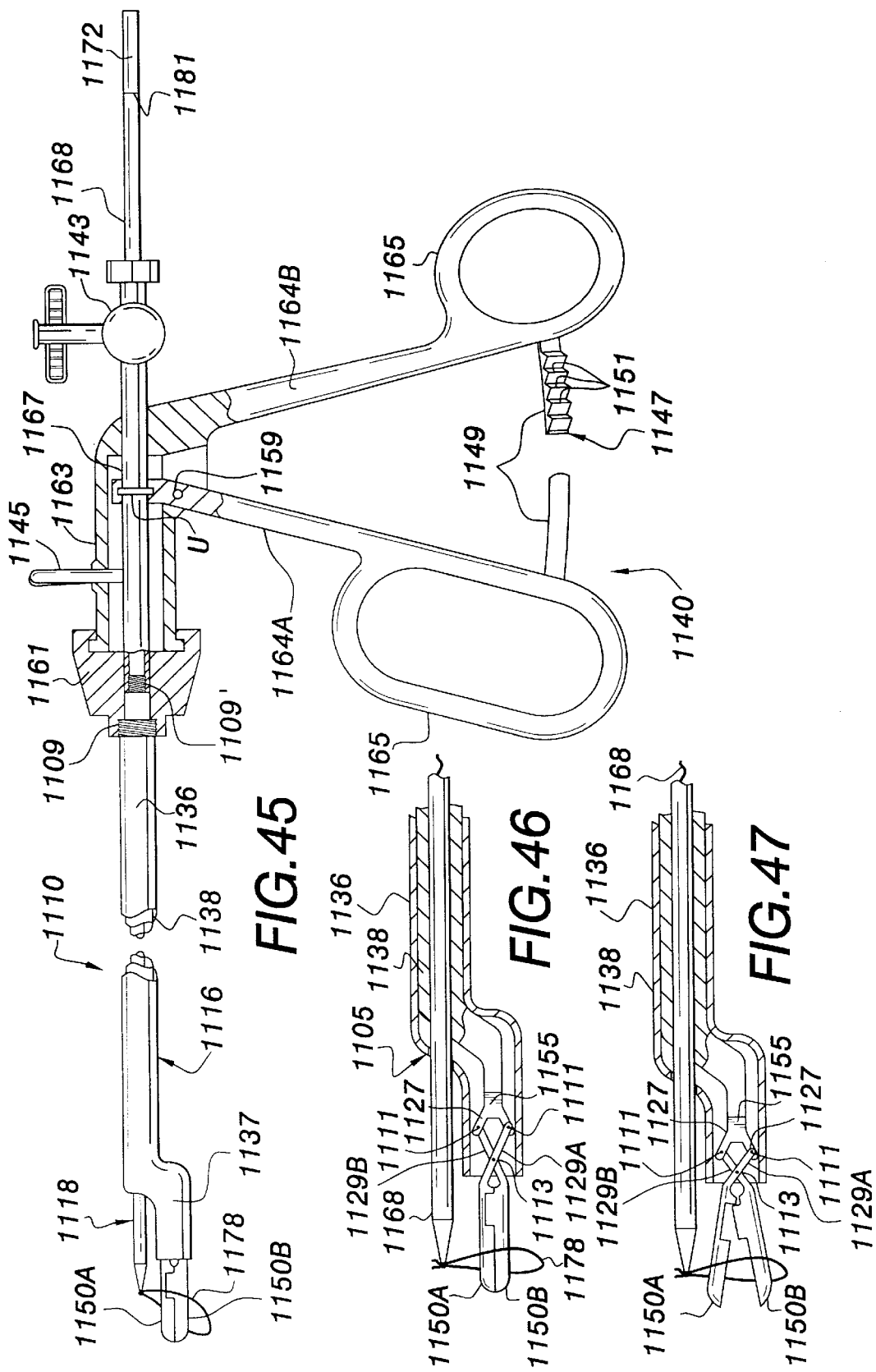

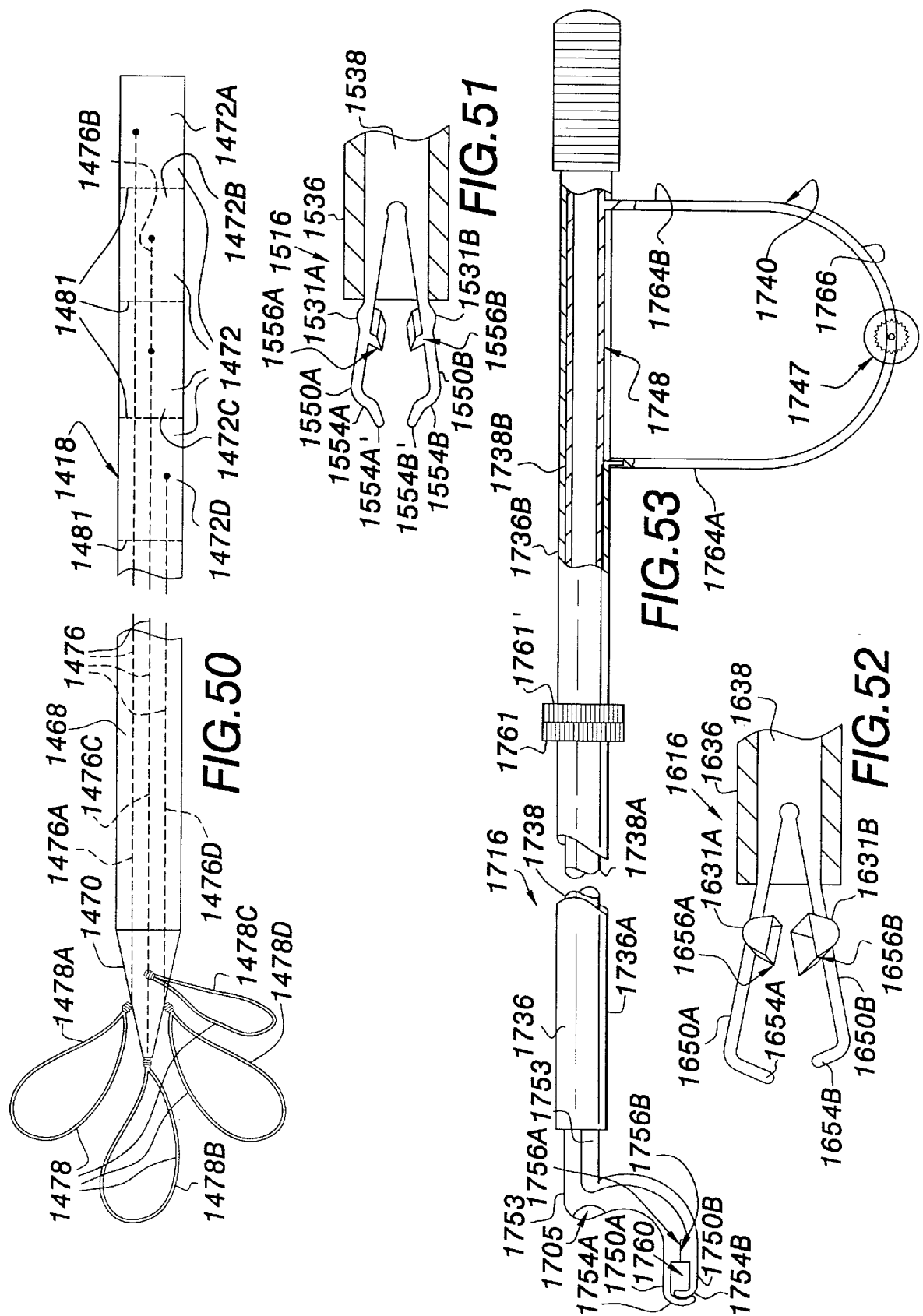

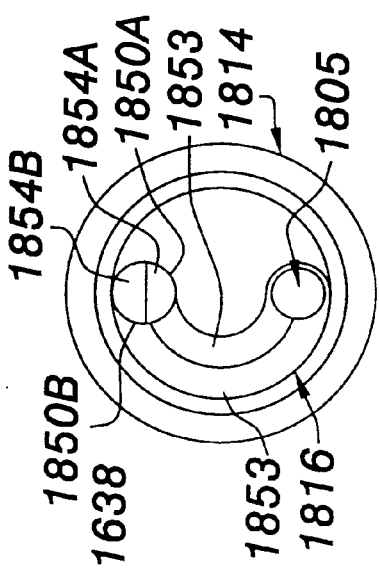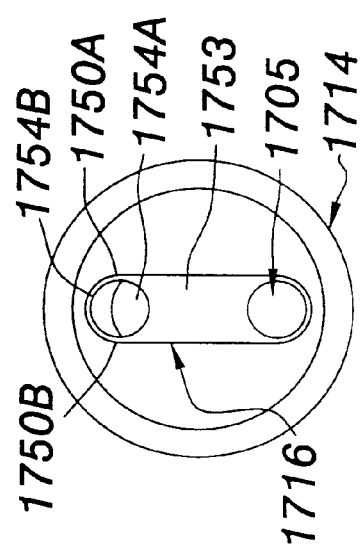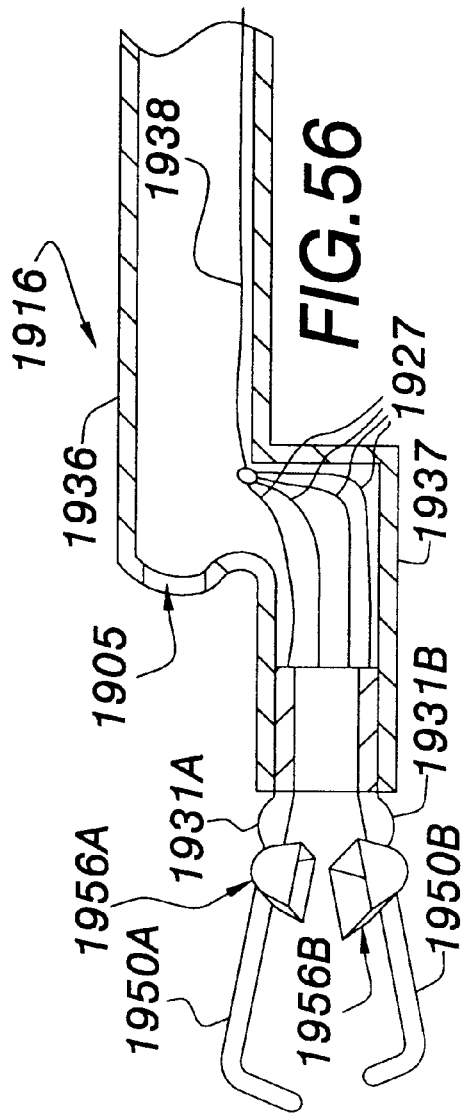

METHODS OF ENDOSCOPIC TUBAL LIGATION

BACKGROUND OF THE INVENTION

1. Field of the Invention

The present invention relates to methods of tubal ligation and, more particularly, to methods of endoscopic ligation of the Fallopian tubes.

2. Discussion of the Prior Art

Various operative procedures previously performed as open surgery requiring relatively large longitudinal incisions have come to be performed endoscopically. In endoscopic procedures, instruments are introduced at internal operative sites through relatively small, artificially created or natural openings providing communication with the internal operative sites from externally thereof. The instruments are manipulated remotely, from externally of the internal operative sites, to perform various operative procedures under visualization provided by an endoscope. Endoscopic procedures have many advantages over open surgical procedures including minimal invasiveness and trauma, shorter hospital stays and recovery times, minimal scarring and patient discomfort, fewer post-operative complications, lower cost and reduced risk for the patient.

Ligating anatomical tissue is a time consuming and tedious part of both endoscopic and open operative procedures due to the difficulty involved in applying an occluding ligature to anatomical tissue as is necessary and desirable in many various procedures. Ligating anatomical tissue is particularly difficult in endoscopic procedures due to the limited room for maneuverability at the internal operative site, the number of different instruments required and the complicated operative steps involved. In particular, separate instruments are required to grasp the anatomical tissue and to position and contract a ligature loop therearound to form a ligature. Furthermore, additional instruments are usually required to cut the ligated tissue as well as the material of the ligature loop. Accordingly, the advantages of endoscopic procedures are sometimes outweighed by the disadvantages caused by the length of time required to perform endoscopic procedures where such time is significantly extended due to the time required for tissue ligation.

Tubal ligation has become increasingly popular as an alternative to presently available contraceptives due to the various adverse complications, inconveniences and relatively high rates of failure associated with contraceptives. It is increasingly common for patients undergoing abdominal surgery for other reasons to request that a tubal ligation be performed at the same time. One technique of tubal ligation that is widely accepted due to its ease of execution, safety and reliability is the Pomeroy technique of tubal ligation. According to the Pomeroy technique, a Fallopian tube is grasped and drawn into a loop formation. The loop formation is ligated with a bioabsorbable ligature. A segment of the ligated loop formation is cut, creating ends extending from the ligature. During healing, the ends separate and occlude, thusly preventing recanalization. The procedure is repeated for the other Fallopian tube to prevent pregnancy. Since it is sometimes possible for another anatomical structure, such as the round ligament, to be mistaken for the Fallopian tube, the Pomeroy technique includes removing the cut segments of the loop formations from the patient's body for positive identification via biopsy. Where the cut segments are identified as being from the Fallopian tubes, proper tubal ligation is confirmed. Where one or both of the cut segments is identified as being from another anatomical structure, the patient can be so advised and, if feasible, surgical correction can be undertaken.

The use of endoscopic techniques for tubal ligation has been limited, however, by a lack of instrumentation and by procedural difficulties due to the limited room for access, maneuverability and visualization at the operative site and due to the need for various different instruments to be introduced at the operative site. The Pomeroy procedure, for example, has not been safely and efficiently performed as endoscopic or laparoscopic surgery. By increasing the safety and efficacy of endoscopic tubal ligation, endoscopic tubal ligation can be made available to patients undergoing other endoscopic operative procedures and can itself represent a viable, safe, cost-effective birth control option for patients not undergoing other endoscopic operative procedures.

SUMMARY OF THE INVENTION

Accordingly, it is a primary object of the present invention to overcome the disadvantages of prior art methods for endoscopic tubal ligation.

Another object of the present invention is to minimize the number and size of the ports needed to access an internal operative site in an endoscopic tubal ligation procedure.

A further object of the present invention is to perform endoscopic tubal ligation via a single port.

An additional object of the present invention is to minimize the size of a single port used to perform endoscopic tubal ligation.

It is also an object of the present invention to expand the types of tubal ligation procedures that can be performed endoscopically.

The present invention has as a further object to perform the Pomeroy procedure of tubal ligation of the Fallopian tubes endoscopically.

Some of the advantages of the present invention are that various operations or procedural steps of tubal ligation normally requiring separate instruments can be performed utilizing fewer instruments and/or instrument assemblies, the tubal ligation procedures according to the present invention can be performed with instrumentation operated with a single hand to perform various operations or functions, anatomical tubal structure can be ligated with a desired tension as tactilely sensed by the surgeon, the taking of a biopsy sample or specimen of the anatomical tubal structure is facilitated, the need for general anesthesia can be avoided with the use of small size ports made possible by the relatively small diametric or cross-sectional sizes of the instrument assemblies, endoscopic tubal ligation can be accomplished utilizing a single port or multiple ports, the Pomeroy technique of tubal ligation can be safely and effectively performed as a miniaturized laparoscopic procedure, and various procedures and functions including irrigation, aspiration, supply of medicaments and other fluids, electrical coagulation, cautery and laser, cryoenergy and ultrasound application can be carried out incidental to the tubal ligation procedures.

These and other objects, advantages and benefits are realized with the present invention as characterized in a method of endoscopic tubal ligation comprising the steps of introducing a distal end of an endoscope, a distal end of a grasper and a distal end of a ligator at an internal operative site through one or more endoscopic sized ports providing communication with the internal operative site from externally thereof, visualizing the internal operative site with the endoscope from externally thereof, grasping an anatomical tubular structure at the internal operative site with the distal end of the grasper and drawing the anatomical tubular structure into a loop formation through a contractible ligature loop of filamentous ligature material at the distal end of the ligator and contracting the ligature loop around the loop formation from externally of the internal operative site to form a ligature. A segment of the loop formation can be cut proximally of the ligature to sever the loop formation and/or for removal of the cut segment from the internal operative site.

Other objects and advantages of the present invention will become apparent from the following description of the preferred embodiments taken in conjunction with the accompanying drawings.

BRIEF DESCRIPTION OF THE DRAWINGS

FIG. 1 is a broken side view of an endoscopic tubal ligation instrument assembly for use in the methods according to the present invention.

FIG. 2 is a broken perspective view of a barrel or platform of the endoscopic tubal ligation instrument assembly.

FIG. 3 is a distal end view of the barrel.

FIG. 4 is a broken perspective view of an endoscope of the endoscopic tubal ligation instrument assembly.

FIG. 5 is a broken side view, partly in section, of a grasping instrument or grasper of the endoscopic tubal ligation instrument assembly.

FIG. 6 is a broken perspective view of a grasping member of the grasping instrument.

FIG. 7 is a broken side view of a distal portion of the grasping instrument showing the grasping members in a closed position.

FIG. 8A is a broken side view of a ligating instrument or ligator of the endoscopic tubal ligation instrument assembly.

FIG. 10 is a broken perspective view illustrating the Fallopian tube being drawn into a loop formation.

FIG. 11 is a broken perspective view illustrating a contractible ligature loop of filamentous ligature material of the ligating instrument positioned around the loop formation.

FIG. 12 is a broken perspective view illustrating the ligature loop contracted around the loop formation of the Fallopian tube to form a ligature.

FIG. 13 is a broken perspective view illustrating a segment of the Fallopian tube loop formation being cut proximally of the ligature with a cutting member of the endoscopic tubal ligation instrument assembly.

FIG. 14 is a broken perspective view of the ligated Fallopian tube after removal of the cut Fallopian tube segment from the patient's body and showing the ligature material being cut with the cutting member proximally of the ligature.

FIG. 15 is a broken side view of a modification of an endoscope for the endoscopic tubal ligation instrument assemblies according to the present invention.

FIG. 16 is a distal end view of the body of the endoscope of FIG. 15.

FIG. 17 is a broken side view of a modification of a grasping instrument for the endoscopic tubal ligation instrument assemblies and/or methods of endoscopic tubal ligation according to the present invention.

FIG. 18 is a broken perspective view of a distal portion of the grasping instrument of FIG. 17.

FIG. 21 is a broken perspective view, partly in section, of the grasping instrument of FIG. 20 drawing a Fallopian tube into a loop formation.

FIG. 22 is a broken perspective view, partly in section, of the ligating instrument of FIG. 19 contracting a ligature loop around the loop formation to form a ligature.

FIG. 23 is a broken perspective view, partly in section, of the grasping instrument of FIG. 20 cutting a segment of the loop formation proximally of the ligature and the ligating instrument of FIG. 19 thereafter cutting the ligature material proximally of the ligature.

FIG. 24 is a broken perspective view, partly in section, of the ligating instrument of FIG. 19 with another ligature loop in a deployed condition for use in forming another ligature.

FIG. 25 is a broken perspective view of another modification of a grasping instrument for the endoscopic tubal ligation instrument assemblies and/or methods of endoscopic tubal ligation according to the present invention.

FIG. 26 is a broken perspective view of the grasping instrument of FIG. 25 with the grasping members in a closed position.

FIG. 27 is a broken perspective view of the grasping instrument of FIG. 25 with the grasping members in a further closed position partly retracted within the outer member of the grasping instrument.

FIG. 28 is a broken perspective view of the grasping instrument of FIG. 25 with the grasping members fully retracted within the outer member.

FIG. 29 is a broken perspective view of an additional modification of a grasping instrument for the endoscopic tubal ligation instrument assemblies and/or methods of endoscopic tubal ligation according to the present invention.

FIG. 30 is a broken perspective view of a distal portion of the grasping instrument of FIG. 29 with a needle thereof in an extended position and the grasping members thereof in the closed position.

FIG. 31 is a broken perspective view of the distal portion of the grasping instrument of FIG. 29 with the needle in the extended position and the grasping members in the open position.

FIG. 32 is a broken side view of a further modification of a grasping instrument for the endoscopic tubal ligation instrument assemblies and/or methods of endoscopic tubal ligation according to the present invention.

FIG. 33 is a broken sectional view of a distal portion of an endoscopic tubal ligation instrument assembly incorporating the grasping instrument of FIG. 32 and the ligating instrument of FIG. 19.

FIG. 34 is a distal end view of the body of an endoscope of the endoscopic tubal ligation instrument assembly of FIG. 33.

FIG. 37 is a broken perspective view of a distal portion of an additional modification of an endoscopic tubal ligation instrument assembly showing the grasping members of the grasping instrument in a confined position and in the closed position.

FIG. 38 is a broken perspective view of a distal portion of the inner member of the grasping instrument of FIG. 37 showing the inner member in a straight configuration and in a bent configuration in dotted lines.

FIG. 39 is a broken perspective view of the distal portion of the endoscopic tubal ligation instrument assembly of FIG. 37 showing the grasping members in an offset or unconfined position and in the closed position.

FIG. 40 is a broken perspective view of the distal portion of the endoscopic tubal ligation instrument assembly of FIG. 37 illustrating the grasping members in the unconfined position and in the open position grasping a Fallopian tube.

FIG. 41 is a broken perspective view of a distal portion of a further modification of an endoscopic tubal ligation instrument assembly according to the present invention depicting the grasping members of the grasping instrument in the confined position and in the closed position.

FIG. 42 is a broken perspective view of the distal portion of the endoscopic tubal ligation instrument assembly of FIG. 41 showing the grasping members in the unconfined position and in the closed position.

FIG. 43 is a broken perspective view of a distal portion of a further modification of an endoscopic tubal ligation instrument assembly according to the present invention illustrating the grasping members of the grasping instrument in the closed position and in the unconfined position.

FIG. 44A is a broken perspective view of the distal portion of the endoscopic tubal ligation instrument assembly of FIG. 43 showing the grasping members in the open position and in the unconfined position.

FIG. 44B is a broken perspective view of the distal portion of the endoscopic tubal ligation instrument assembly of FIG. 43 showing modified grasping members.

FIG. 45 is a broken side view, partly in section, of an additional modification of an endoscopic tubal ligation instrument assembly.

FIG. 46 is a broken side view, partly in section, of a distal portion of the endoscopic tubal ligation instrument assembly of FIG. 45 showing the grasping members of the grasping instrument in the closed position.

FIG. 47 is a broken side view, partly in section, of the distal portion of the endoscopic tubal ligation instrument assembly of FIG. 45 illustrating the grasping members in the open position.

FIG. 50 is a broken side view of another embodiment of a ligating instrument for the endoscopic tubal ligation instrument assemblies and/or methods of endoscopic tubal ligation according to the present invention.

FIG. 51 is a broken side view, partly in section, of a distal portion of a modified grasping instrument.

FIG. 52 is a broken side view, partly in section, of a distal portion of another modified grasping instrument.

FIG. 53 is a broken side view, partly in section, of another modification of a grasping instrument.

FIG. 54 is a distal end view of the grasping members of the grasping instrument of FIG. 53 disposed in an endoscope in a confined position.

FIG. 55 is a distal end view of the grasping members of a modified grasping instrument disposed in an endoscope in a confined position.

FIG. 56 is a broken side view, partly in section, of a further modification of a grasping instrument.

DESCRIPTION OF THE PREFERRED EMBODIMENTS

Figure 8B:
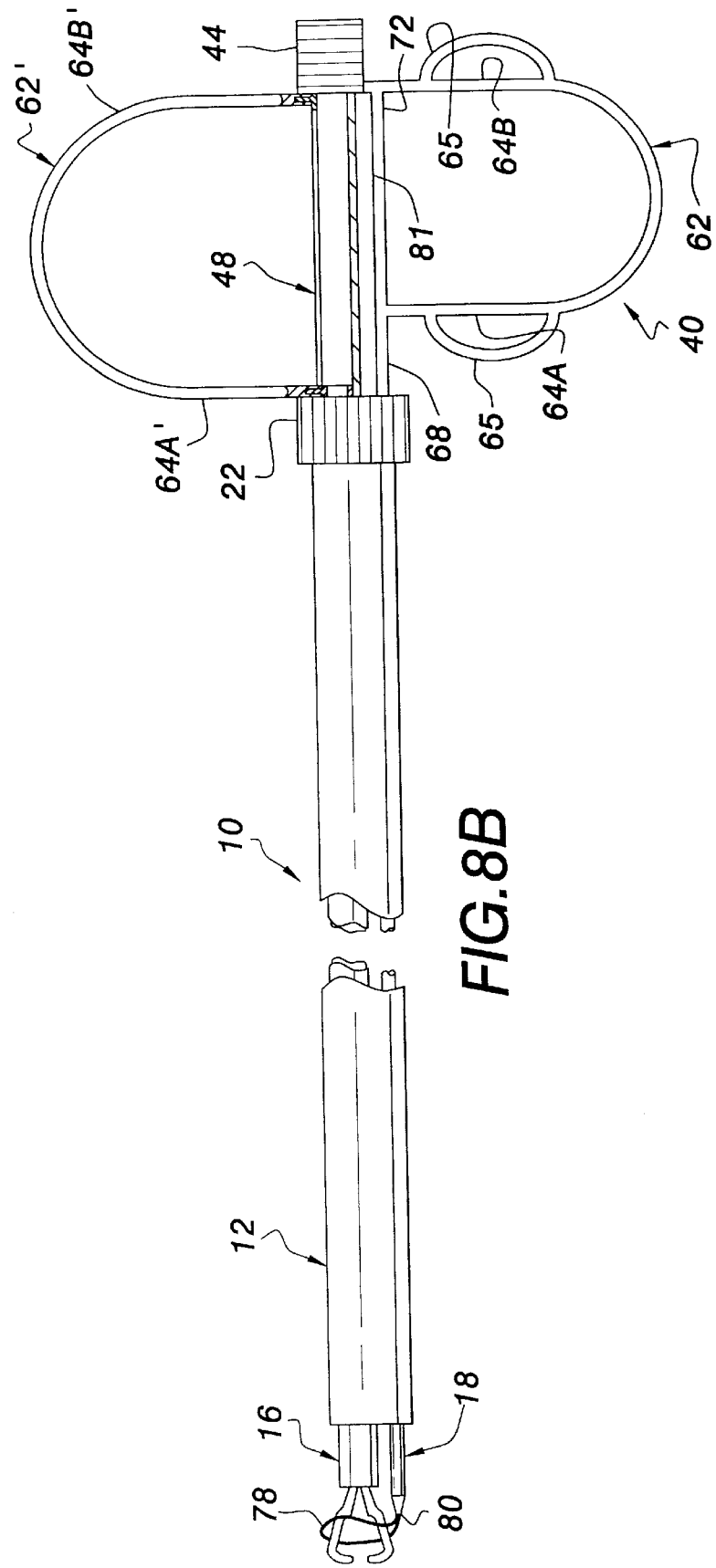
FIG. 8B is a broken side view, partly in section, of a modification of the endoscopic tubal ligation instrument assembly.

An endoscopic tubal ligation instrument assembly for use in the methods of endoscopic tubal ligation according to the present invention is illustrated at 10 in FIG. 1 and includes an elongate passage or channel defining member, platform or barrel 12 and an endoscope 14, a grasping instrument or grasper 16 and a ligating instrument, ligating device or ligator 18 disposed in barrel 12. As shown in FIG. 2, barrel 12 includes an elongate, hollow cylindrical or tubular member 19 terminating distally at a distal end 20 for being disposed at an internal operative site in the patient's body, typically within an anatomical cavity, and terminating proximally at a proximal end for being disposed externally of the internal operative site, such as externally of the anatomical cavity. A diametrically enlarged cylindrical collar 22 is disposed on the proximal end of the tubular member 19 and has longitudinally extending external grooves to facilitate grasping. As shown in FIGS. 2 and 3, barrel 12 includes a plurality of channels or passages 24 extending longitudinally through tubular member 19. Barrel 12 has three parallel channels 24A, 24B and 24C of different diametric or cross-sectional sizes corresponding to the external diametric or cross-sectional sizes of endoscope 14, grasping instrument 16 and ligating instrument 18, respectively. However, the barrel 12 can have one or more additional channels for receiving one or more additional instruments to be introduced at the internal operative site and/or for fluid flow therethrough. One or more light transmitting elements, such as a plurality of light transmitting fibers 26, extend longitudinally through the tubular member 19 and are disposed in the space between an inner surface of tubular member 19 and the channels 24A, 24B and 24C. In the case of barrel 12, the channels 24A, 24B and 24C are formed by thin wall, hollow cylindrical or tubular sleeves 28A, 28B and 28C, respectively, extending longitudinally through the tubular member 19 with the light transmitting fibers 26 being disposed externally of sleeves 28A, 28B and 28C in the space between the sleeves 28A, 28B and 28C and the inner surface of tubular member 19. The sleeves 28A, 28B and 28C are preferably arranged closely or compactly in tubular member 19 to minimize the external diametric or cross-sectional size of barrel 12. For example, one or more of the sleeves 28A, 28B and 28C can have its periphery in contact with or touching the inner surface of tubular member 19, as shown in FIG. 3 for sleeves 28A and 28B, and/or one or more of the sleeves 28A, 28B and 28C can have its periphery in contact with or touching the periphery of another sleeve, as shown in FIG. 3 for sleeves 28A and 28B. Channels 24 can be defined in tubular member 19 without sleeves to further reduce the external diametric or cross-sectional size of barrel 12. For instance, light transmitting fibers 26 can be arranged in tubular member 19 to define channels 24, and the inner surface of tubular member 19 can define peripheral or circumferential segments of one or more of the channels. Light transmitting fibers 26 are designed to transmit light from a light source (not shown) to the distal end 20 to provide illumination at the internal operative site, the barrel 12 having a light coupler 15 connectible with a light source.

Endoscope 14, which can be rigid or flexible or partly rigid and partly flexible, includes an elongate cylindrical body 30 having an image receiver or observation window 32 at a distal end thereof and an eyepiece 34 at a proximal end thereof as shown in FIG. 4. As shown by way of example in FIG. 4, the body 30 is divided into a first or distal segment and a second or proximal segment at a junction J, the second segment carrying eyepiece 34. The first segment can be flexible while the second segment is rigid or vice versa. The body 30 houses optics or a viewing system, such as various lenses and/or mirrors, optically coupling image receiver 32 with eyepiece 34 for transmitting an image from observation window 32 to eyepiece 34. The eyepiece 34 for endoscope 14 is axially aligned with body 30; however, it should be appreciated that the eyepiece 34 can be offset from the body 30 or not axially aligned therewith and can be angularly adjustable. Where the eyepiece 34 is offset from the body 30, the eyepiece 34 can be offset from the body 30 parallel or at various angles to the body 30. The first segment can be longer than the second segment, and the second segment can be pivotally mounted to the first segment for pivotal or angular movement relative to the first segment to adjust the position of eyepiece 34. The endoscope 14 can be designed to transmit an image from observation window 32 for viewing on a video monitor.

As shown in FIG. 5, grasping instrument or grasper 16 includes an elongate, hollow or tubular outer member 36, an elongate inner member 38 disposed within outer member 36 and a handle 40 mounting proximal ends of the outer and inner members. Outer member 36 has a distal end 42 and a proximal end mounted to a diametrically enlarged, cylindrical collar 44 disposed proximally of handle 40 and provided with circumferentially extending external grooves to facilitate grasping. A transverse ear or flange 46 is disposed on the outer member 36 distally of collar 44, and a slot 48 is formed in outer member 36 longitudinally or axially aligned with ear 46 and extending longitudinally, distally therefrom.

Inner member 38 has a distal end carrying or formed as at least one grasping, engaging or jaw member 50 and a proximal end provided with a transverse ear or flange 52 for being disposed in slot 48. Inner member 38 has opposed grasping members 50A and 50B including inwardly curving or angled distal tips, ends or fingers 54A and 54B, respectively, and inwardly protruding cutting members 56A and 56B, respectively, spaced proximally from tips 54A and 54B. Each cutting member includes one or more cutting edges or blades 57 for cutting anatomical tissue. Cutting members 56A and 56B are in the nature of tissue collection or biopsy boxes each having a pair of inwardly protruding longitudinal cutting edges 57 connected to one another by inwardly protruding transverse side walls 58 to form or define a box as shown in FIG. 6 for cutting member 56B. Cutting edges 57 extend lengthwise along opposed lateral sides of the grasping member and the side walls 58 extend perpendicularly between cutting edges 57. The cutting members 56A and 56B are proximally spaced from the tips 54A and 54B, respectively, to define recesses between the tips and the distal ends of the cutting edges 57. Accordingly, each grasping member has a recess and the recesses of the grasping members are aligned with one another when the grasping members are in a closed position as explained further below. One of the grasping members is longer than the other such that tips 54A and 54B overlap one another in the closed position. As shown in FIG. 7, grasping member 50B is longer than grasping member 50A; however, the grasping members can be the same length and the tips do not have to overlap one another in the closed position. The tips 54A and 54B can protrude inwardly the same distance as the cutting members, or the tips 54A and 54B can protrude inwardly a distance different than the distance that the cutting members protrude inwardly. The cutting edges of one grasping member can abut the cutting edges of the opposed grasping member in end to end fashion when the grasping members are in the closed position or the cutting edges can overlap one another in the closed position. For example, one of the boxes can be made smaller than the other to nest or fit within the larger size box as shown for cutting members 56A and 56B. Depending on procedural use, one or both of the side walls 58 can be sharpened along their edges to define additional cutting edges.

Grasping members 50A and 50B are normally disposed in an open position as shown in FIG. 5 wherein the grasping members extend angularly outwardly away from one another. Accordingly, tip 54A and cutting member 56A of grasping member 50A are spaced from the tip 54B and cutting member 56B of grasping member 50B to allow anatomical tubular structure such as a Fallopian tube to be received between the grasping members. Grasping members 50A and 50B are movable inwardly toward one another, i.e. in the direction of the longitudinal axis of the inner member 38, from the open position to a closed position as shown in FIG. 7 wherein tips 54A and 54B are disposed closer to one another than they are in the open position. The tips of grasping members 50A and 50B overlap one another in the closed position and the cutting edges of cutting member 56A move past the cutting edges of cutting member 56B. In the closed position for grasping members 50A and 50B, the recess of grasping member 50A is in alignment with the recess of grasping member 50B to form a grasping space 60 between the tips and the cutting members, the grasping space 60 being closed distally by tips 54A and 54B, being closed proximally by distal side walls 58 and being open along the lateral sides of the grasping members.

The grasping members can be designed in many various ways to be normally disposed in the open position and to be movable to the closed position and back to the open position. The grasping members can be biased toward the open position. For example, the grasping members can be made entirely or partly of resilient, flexible or spring materials, or materials having shape memory, to be resiliently biased toward the open position while being movable to the closed position and back to the open position. The grasping members can contact one another or not contact one another in the closed position. For example, the tips of the grasping members can abut one another in end to end fashion, can overlap one another or can be spaced from one another when the grasping members are in the closed position. Accordingly, it is not necessary for the grasping space to be closed distally in the closed position for the grasping members. However, it is desirable that the grasping space be closed distally for ligation of anatomical tubular structure. The cutting edges can be designed to abut one another in end to end fashion in the closed position, or the cutting edges can be designed to move past or overlap one another when the grasping members are moved to the closed position. Accordingly, anatomical tubular structure, such as a Fallopian tube, disposed in the grasping space 60 to extend transverse to the grasping members, i.e. transverse to the inner member longitudinal axis, will be grasped, held or captured between the grasping members in the closed position; and, when positioned between the cutting members 56A and 56B to extend transverse to the cutting edges 57, the anatomical tubular structure will be cut by the cutting edges when the grasping members are moved from the open position to the closed position. The distal tips of the grasping members can have various configurations including bent, hook-like and spoon-like shapes for picking up and lifting the anatomical tubular structure as well as "kissing" tips. The inner member 38 is preferably hollow or tubular as shown in FIG. 5 to allow fluid flow therethrough and/or to allow instruments to be introduced at and withdrawn from the internal operative site through the lumen of the inner member via the collar 44 and the proximal end of the outer member 36.

Handle 40 comprises a U-shaped hand grip 62 having a distal leg 64A connected to ear 52, a proximal leg 64B connected to ear 46 and a curved base 66 connecting the proximal and distal legs. As shown in FIG. 5, an upper end of proximal leg 64B is formed with a recess for receiving ear 46, and an upper end of distal leg 64A is formed with a recess for receiving ear 52 to connect the handle 40 to the outer and inner members. Handle 40 is made partly or entirely of resilient, flexible or spring materials, or materials having shape memory, to maintain grasping instrument 16 in a rest position as shown in FIG. 5 wherein outer member 36 is in a proximal longitudinal position relative to grasping members 50A and 50B with the grasping members 50A and 50B disposed in the open position beyond the outer member distal end 42. Handle 40 can be manually compressed or squeezed to move the outer member 36 and/or the inner member 38 relative to one another such that the outer member is in a distal longitudinal position relative to grasping members 50A and 50B causing the grasping members 50A and 50B to be moved inwardly toward one another to the closed position as shown in FIG. 7. The distal end of the outer member in the distal longitudinal position is closer to tips 54A and 54B than it is in the proximal longitudinal position such that the grasping members are moved to the closed position due to engagement and constraint by the outer member. Release of the manual compressive or squeezing force on handle 40 causes the grasping instrument to return to the rest position due to the resilient bias of handle 40. If desired, handle 40 can include bilateral hand grips as represented by additional U-shaped hand grip 62' shown in dotted lines in FIG. 1 and shown in FIG. 9. Handle 40 preferably includes a locking mechanism 47 for locking the handle 40 in various compressed positions and/or in a spread position, the locking mechanism 47 being of the type described in applicant's prior application Ser. No. 08/694,385, filed Aug. 8, 1996 and incorporated herein by reference.

One example of a ligating instrument, ligating device or ligator 18 for use in the instrument assemblies and/or methods of the present invention is illustrated in FIG. 8A and comprises a ligating device of the type called an Endoloop™ made by Ethicon EndoSurgery, Inc. The ligating instrument 18 includes an elongate tubular member or knot pusher 68 having a tapered distal end 70, a proximal end 72 and a ligature supply 74 carried by tubular member 68. Ligature supply 74 includes a length of filamentous ligature material 76, which is preferably bioabsorbable, extending through the lumen of tubular member 68 and having a distal end forming a variable size or contractible ligature loop 78 and a proximal end secured to the proximal end 72 of tubular member 68. Distal end 70 has a hole or aperture therein communicating with the lumen of tubular member 68, and the ligature material 76 slidably passes through the aperture such that the ligature loop 78 is disposed externally of the distal end 70. Ligature loop 78 includes a loop segment 79 of ligature material 76 and a knotting element in the form of a knot 80, such as a slip or hangman's knot or other such pretied slidable knot, formed in the ligature material 76 and through which the length of ligature material 76 slidably passes. The knot 80 is larger in size than the hole or aperture in distal end 70 and cannot pass therethrough. The proximal end 72 of the tubular member 68 is breakable or frangible such that it can be separated or broken off from the remainder of the tubular member 68 at a break point 81 as shown in dotted lines in FIG. 8A to permit the ligature material 76 and the tubular member 68 to be moved longitudinally relative to one another. Accordingly, the ligature material 76 can be pulled proximally through the lumen of tubular member 68 to contract or reduce the size of loop segment 79 as the knot 80 remains externally of distal end 70 and/or the tubular member 68 can be moved or pushed distally along the length of ligature material 76 as the proximal end 72 is held to move or push knot 80 therealong to contract the loop segment 79.

FIG. 8B illustrates a modification of instrument assembly 10 wherein the ligating instrument 18 and the grasping instrument 16 are operated by a single handle 40. Handle 40 illustrated in FIG. 8B includes bilateral U-shaped hand grips 62 and 62', the handgrip 62' having proximal and distal legs 64B' and 64A', respectively, connected to the outer member 36 and the inner member 38, respectively, of the grasping instrument 16 as described above for handgrip 62 of FIG. 5. The handgrip 62 of FIG. 8B is similar to the hand grip 62 of FIG. 5 and has a proximal leg 64B secured to collar 44 and a distal leg 64A secured to the tubular member 68 of the ligating instrument 18. The proximal end 72 of the tubular member 68 is secured to the proximal leg 64B. The hand grip 62 of FIG. 8B is made partly or entirely of resilient materials allowing legs 64A and 64B to be manually spread apart from one another from the rest position shown in FIG. 8B as facilitated by finger rings 65. Accordingly, when the proximal end 72 is separated from the remainder of the tubular member 68 at the break point 81, spreading operation of hand grip 62 causes the tubular member 68 to be moved distally and/or the length of ligature material to be moved proximally to contract the ligature loop 78. Release of the manual spreading force on hand grip 62 of FIG. 8B causes the hand grip 62 to return to the rest position. Either or both of the hand grips 62 and 62' can be provided with a locking mechanism for locking the hand grips in the compressed position and/or a spread position.

The endoscopic tubal ligation instrument assembly 10 of FIG. 1 is arranged with endoscope 14 disposed in channel 24A, grasping instrument 16 disposed in channel 24B and ligating instrument 18 disposed in channel 24C of barrel 12. Endoscope 14 is disposed in channel 24A with observation window 32 aligned with the distal end 20 of the barrel and with eyepiece 34 disposed proximally of handle 40. If desired, the endoscope can be provided with a stop or abutment to limit or control the forward distance that the endoscope can be inserted in the barrel. If desired, the endoscope can be introduced through the barrel to position the observation window distally of the distal end of the barrel and can be slidable relative to the barrel to adjust the position of the endoscope prior to or during use to facilitate visualization of the internal operative site. The endoscope and/or the barrel can be provided with a releasable locking mechanism to selectively fix or secure the position of the endoscope relative to the barrel. The eyepiece 34 should be spaced from the handle 40 a distance sufficient to prevent contamination between the eyepiece and the handle, such distance preferably being in the range of 5–10 cm.

Grasping instrument 16 is disposed in channel 24B with the distal leg 64A of handle 40 in abutment with the collar 22 of the barrel such that the grasping members 50A and 50B in the open position protrude distally beyond the distal end 20 of the barrel. To permit insertion of the grasping instrument 16 through channel 24B, the grasping members 50A and 50B are moved to the closed position via squeezing operation of handle 40; and, once the grasping members 50A and SOB are disposed externally of barrel 12, the handle 40 is released to return the grasping instrument to the rest position such that the grasping members are again in the open position.

The ligating instrument 18 is disposed in barrel 12 with the distal end 70 thereof disposed distally of the distal end 20 of barrel 12 with the ligature loop 78 disposed around the grasping members 50A and 50B such that the grasping members protrude distally through the ligature loop 78. The proximal end 72 of the tubular member 68 is attached to the remainder of tubular member 68 at break point 81, the proximal end 72 and break point 81 being disposed proximally of the collar 22 of barrel 12 and alongside handle 40.

In the case of instrument assembly 10, endoscope 14, grasping instrument 16 and ligating instrument 18 are each capable of longitudinal sliding movement relative to barrel 12; however, it should be appreciated that any or all of endoscope 14, grasping instrument 16 and ligating instrument 18 can be fixed or non-movable relative to barrel 12 except for that movement required for operation of the respective instruments. In the case of instrument assembly 10, the outer member 36 of grasping instrument 16 protrudes distally beyond the distal end 20 of barrel 12 when the grasping instrument 16 is fully inserted in the barrel with handle 40 in abutment with collar 22; however, it should be appreciated that the outer member 36 need not protrude beyond the barrel 12 when the grasping instrument is fully inserted therein. By sizing the channels 24A, 24B and 24C to closely correspond to the external peripheral or cross sectional sizes of the endoscope 14, the grasping instrument 16 and the ligating instrument 18, respectively, the endoscope, the grasping instrument and the ligating instrument can be frictionally held in the barrel to frictionally resist movement while being capable of movement relative to the barrel in response to a manual force sufficient to overcome the frictional resistance.

Figure 9:
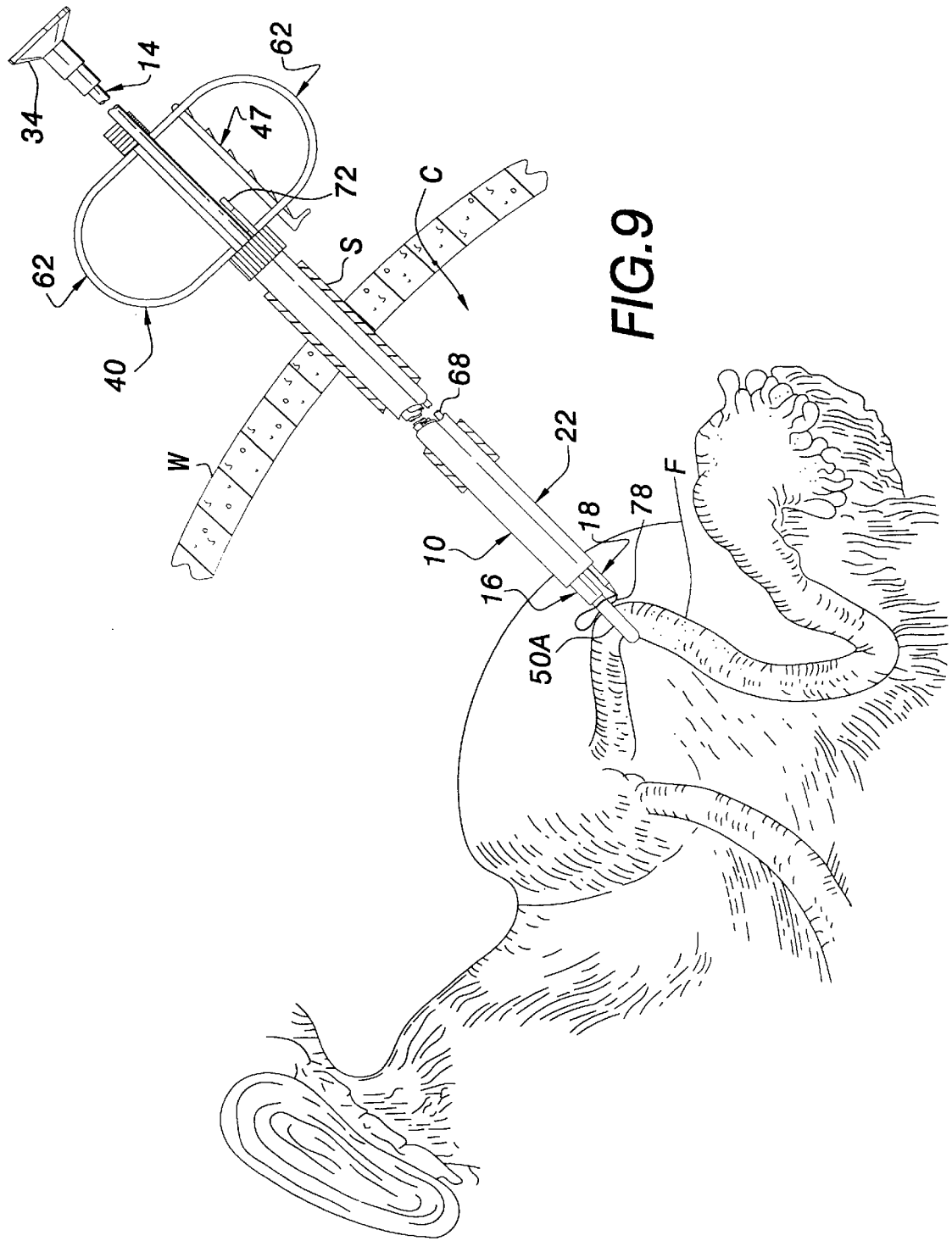
FIG. 9 is a broken perspective view, partly in section, of the endoscopic tubal ligation instrument assembly of FIG. 1 introduced through a port in the abdominal cavity wall to grasp a Fallopian tube with the grasping members in a single port endoscopic tubal ligation procedure according to the present invention.

In a single port procedure of endoscopic tubal ligation, a distal end of the endoscopic tubal ligation instrument assembly 10 is introduced at an internal operative site in the body, such as in the abdominal cavity C, through a relatively small size port or passage providing communication with the internal operative site from externally thereof. The port can be an artificially created opening or incision or a natural anatomical opening or passage. FIG. 9 illustrates instrument assembly 10 extending through an incision or opening in a wall W of the abdominal cavity C with a proximal end of the instrument assembly 10 disposed externally of the abdominal cavity C. The port through which the instrument assembly 10 is introduced can be established conventionally as a puncture-type incision with the use of a penetrating member of a penetrating instrument. The instrument assembly 10 is typically introduced through the cavity wall W via a portal sleeve or cannula S disposed in the port and extending through the cavity wall W to provide a passage through the cavity wall W after the penetrating member is withdrawn. As part of the penetrating procedure, the abdominal cavity is insufflated to form a pneumoperitoneum. Insufflation gas, such as nitrous oxide or carbon dioxide, is introduced in the abdomen to lift the cavity wall away from the contents of the cavity to form a pneumoperitoneum providing increased space for access and visualization as shown in FIG. 9. Since it is important to maintain the pneumoperitoneum, the portal sleeve or cannula is typically provided with a gaseous seal preventing the ingress and egress of fluid to and from the abdomen when no instrument passes therethrough. Various gaseous seals can be provided in communication with the portal sleeve or cannula including gaseous seals for sealingly engaging instruments of various sizes introduced through the portal sleeve.

As shown in FIG. 9, the port is preferably no larger than necessary to accommodate the portal sleeve S, and the portal sleeve S is preferably no larger than necessary to accommodate the instrument assembly 10 to minimize the size of the port needed to access the anatomical cavity C. By minimizing the size of the port, the need for general anesthesia can be avoided allowing the procedure to be performed under local anesthesia in non-hospital sites. Illumination of the abdominal cavity is provided by light transmitting fibers 26. The abdominal cavity and the tubal ligation procedure are visualized, from externally of the abdominal cavity, with endoscope 14 via eyepiece 34 and/or a video monitor.

Once a distal end of instrument assembly 10 has been introduced in the anatomical cavity C, the instrument assembly 10 is manipulated externally of the anatomical cavity to receive anatomical tubular structure, such as a portion of one of the Fallopian tubes F, between the grasping members 50A and 50B. In the illustrated procedure, the grasping members 50A and 50B are positioned on opposite sides of the ampullary or isthmic portion of Fallopian tube F such that the portion of tube F extends transversely to the grasping members 50A and 50B, i.e. transverse to the longitudinal axis of inner member 38, with the portion of tube F disposed forwardly of cutting members 56A and 56B in alignment with the recesses of the grasping members. Grasping member 50B can support the portion of tube F in its recess and can be used to pick up and hold tube F. Where the grasping instrument has only one grasping member, it is preferred that the one grasping member be provided on a lower or bottom portion of the grasping instrument to facilitate picking up and supporting anatomical tubular structure with the one grasping member. Handle 40 is compressed to move the grasping members 50A and 50B from the open position to the closed position as shown in FIG. 10 such that the portion of Fallopian tube F is captured or held in the grasping space 60 between the grasping members.

The entire instrument assembly 10 is moved proximally, or the grasping instrument 16 can be moved proximally relative to the barrel 12 or relative to the rest of the instrument assembly, to draw the Fallopian tube F into a loop formation as shown in FIG. 10. The ligating instrument 18 is moved distally relative to barrel 12 or relative to the rest of the instrument assembly as shown in FIG. 11 to position the ligature loop 78 around the anatomical tissue held by the grasping members. In the illustrated procedure, the ligature loop is removed from the grasping members and is positioned around the loop formation of the Fallopian tube F such that a bend or knuckle of the loop formation protrudes through the ligature loop 78. It is not necessary, however, for the ligature loop to be disposed around the grasping members prior to use. Rather, the ligature loop can be disposed over or laid upon the Fallopian tube, and the grasping members can be inserted within or through the ligature loop to grasp the Fallopian tube. The length of the bend or knuckle of the Fallopian tube that is drawn through the ligature loop can be adjusted, controlled or selected so that a desired length of bend or knuckle is drawn through the ligature loop as determined by the surgeon.

Once the ligature loop 78 has been properly positioned over or around the anatomical tubular structure, the proximal end 72 of the tubular member 68 is broken or separated from the remainder of the tubular member 68 at breakpoint 81. The tubular member 68 is moved longitudinally, distally along the length of ligature material 76 while the proximal end 72 is held externally of the anatomical cavity C to push or move knot 80 distally toward the loop formation of tube F to contract or reduce the size of loop segment 79 of the ligature loop 78 around the loop formation to form a ligature as shown in FIG. 12. Movement of tubular member 68 can be accomplished by moving the tubular member 68 distally relative to the barrel 12 and the rest of the instrument assembly. Alternatively and/or in addition to distal movement of tubular member 68, the freed or unattached proximal end 72, which is secured to the ligature material 76, can be pulled proximally relative to the tubular member 68 causing the ligature material 76 to be moved longitudinally, proximally relative to and through the tubular member 68 as the knot 80 remains held externally of the distal end 70 to contract the loop segment 79 around the loop formation to form a ligature. The ligature loop 78 is contracted or reduced in size around the loop formation of the Fallopian tube F until a desired tension has been obtained for the ligature as can be tactilely sensed or felt by the surgeon at the proximal end of the ligating instrument 18. It is desirable in some tubal ligation techniques, such as the Pomeroy technique, to avoid excessive crushing of the Fallopian tube F to prevent tubal fistula formation, and the ligating instrument 18 allows the Fallopian tube F to be controllably ligated to a desired tension.

Once the Fallopian tube F has been ligated to the desired tension, handle 40 is released for movement toward the rest position causing the grasping members 50A and 50B to move from the closed position toward the open position. The grasping instrument is manipulated to receive the bend of the Fallopian tube F between the grasping members 50A and 50B to extend transversely to the grasping members in alignment with the cutting edges 57. If necessary, the Fallopian tube can be manipulated via the ligature material to maneuver the ligature and facilitate positioning of the Fallopian tube between the cutting edges 57. The grasping members 50A and 50B are moved toward the closed position via compression of handle 40 causing a segment of the loop formation of Fallopian tube F to be cut or severed by cutting members 56A and 56B proximally of the ligature as shown in FIG. 13. The cut segment of Fallopian tube F will remain held by the cutting members 50A and 50B, the cut segment being contained within the biopsy boxes. The grasping instrument is withdrawn from the abdominal cavity C for removal and retrieval of the cut segment externally of the patients body. As shown in FIG. 14, two free ends E of Fallopian tube F will then extend proximally from the ligature. As the ligature material 76 is absorbed during healing, the ends E separate and occlude to prevent recanalization. The segment of Fallopian tube F is biopsied for positive identification as confirmation of proper ligation of the Fallopian tube F and not another anatomical structure.

The grasping instrument 16 is reintroduced in the abdominal cavity, and the ligating instrument 18 is moved proximally or backed away from the ligature to present a segment 82 of ligature material extending proximally from the ligature. Instrument assembly 10 is manipulated to receive the segment 82 of ligature material 76 between grasping members 50A and 50B, which are in the open position, with the segment 82 extending transverse to the grasping members in alignment with cutting edges 57. Handle 40 is compressed to move the grasping members 50A and 50B toward the closed position causing the cutting edges 57 to cut the segment 82 of ligature material 76 proximally of the ligature as shown in FIG. 14.

Ligating instrument 18 is withdrawn from barrel 12, and another ligating instrument 18 is inserted in barrel 12 for introduction in the abdominal cavity for use in forming another ligature. The ligating instrument can be withdrawn from the barrel while the barrel remains in the portal sleeve or the entire instrument assembly 10 can be withdrawn from the abdominal cavity and reintroduced therein with the ligature loop of another ligating instrument disposed around the grasping members. The instrument assembly 10 is utilized to ligate the other Fallopian tube in the same manner as previously described to prevent conception and, therefore, pregnancy. If desired, more than one ligature can be formed in one or both of the Fallopian tubes for redundant protection. Where multiple ligatures are formed in a Fallopian tube, the ligatures can be placed next to or on top of one another.

Where the grasping instrument 16 and ligating instrument 18 are removable from the barrel, the barrel can be left in place in the abdominal cavity allowing the grasping instrument and ligating instrument to be withdrawn from the barrel preparatory to forming another ligature. Depending on the structure of the grasping instrument and the ligating instrument, the grasping instrument and the ligating instrument can be withdrawn from the barrel separately or together as a unit. It should be appreciated that, although placement of the ligature loop around the loop formation of the Fallopian tube may be facilitated when the ligature loop is pre-loaded or arranged to be disposed around the grasping members, it is not necessary for the ligature loop to be pre-loaded or disposed around the grasping members when introduced in the abdominal cavity. For example, the ligature loop can be placed over the Fallopian tube F, and the grasping members can be used to pickup, engage or grasp the anatomical tissue through the ligature loop. It should be appreciated that the procedures described herein can be performed as mini-lap procedures as well as open procedures.

FIG. 15 illustrates at 114 a modification of an endoscope for use in the endoscopic tubal ligation instrument assemblies and/or methods of endoscopic tubal ligation according to the present invention. Endoscope 114 differs from endoscope 14 in that endoscope 114 itself comprises a passage or channel defining member defining the channels for receiving a grasping instrument and/or a ligating instrument, respectively, and the eyepiece 134 for endoscope 114 is offset from the elongate body 130. Endoscope 114 includes elongate body 130 having an observation window 132, shown in FIG. 16, at its distal end and having a proximal end mounted to a hub 133 coupled with eyepiece 134. Hub 133 is connected to eyepiece 134 by a connecting arm 135 having an arm segment 135A extending perpendicularly from hub 133, i.e. at a 90° or right angle to a longitudinal axis of elongate body 130, and an arm segment 135B extending perpendicularly from arm segment 135A in the proximal direction parallel with the longitudinal axis of elongate body 130. Accordingly, endoscope 114 is representative of an offset endoscope wherein the eyepiece is parallel to the endoscope body. Eyepiece 134 is disposed at a proximal end of arm segment 135B to be offset from and not aligned with the longitudinal axis of elongate body 130 and to be disposed proximally of a proximal end of elongate body 130. The eyepiece 134 is optically coupled to the observation window 132 for optically transmitting an image from observation window 132 for viewing at eyepiece 134. The hub 133 is provided with a light connector 115 for being connected or coupled with a light source. As shown in FIG. 16, sleeves 128B and 128C extend longitudinally through body 130 parallel with the longitudinal axis thereof to define channels 124B and 124C. A plurality of light transmitting fibers 126 are disposed within the elongate body 130 to transmit light from the light source to a distal end of the endoscope 114.

A grasping instrument and/or a ligating instrument can be disposed in the channels 124B and 124C for introduction in the abdominal cavity along with endoscope 114 to perform an endoscopic tubal ligation procedure as described above. Endoscope 114 provides the channels for receiving the grasping instrument and/or the ligating instrument and thusly eliminates the need for a separate barrel. Accordingly, the endoscope 114 forms an endoscopic tubal ligation instrument assembly with a ligating instrument and/or a grasping instrument disposed therein, and the external diametric or cross sectional size of the endoscope 114 defines the external size of the instrument assembly. The external diametric or cross-sectional size of the endoscope 114 can be minimized to minimize the size of the port through which the endoscopic tubal ligation instrument assembly is introduced into the abdominal cavity. Since the endoscope 114 can accommodate both a grasping instrument and a ligating instrument, the resulting endoscopic tubal ligation instrument assembly can be utilized in a single port procedure. Where either a grasping instrument or a ligating instrument is disposed in endoscope 114, the endoscope and such instrument forms an endoscopic tubal ligation instrument assembly for use in multiple port endoscopic tubal ligation procedures.

A modification of a grasping instrument for use in the endoscopic tubal ligation instrument assemblies and/or methods of endoscopic tubal ligation according to the present invention is illustrated at 116 in FIG. 17. Grasping instrument 116 differs from grasping instrument 16 in that one or both of the grasping members 150A and 150B for grasping instrument 116 is longitudinally movable to obtain the open and closed positions. Grasping instrument 116 includes outer member 136 carrying or forming grasping member 150B and connected proximally to a collar or retaining ring 144 connected in turn to a distal leg 164A of a unilateral U-shaped handle 140. Grasping member 150B has a distal tip 154B and a recess disposed proximally of distal tip 154B. The inner member 138 of grasping instrument 116 terminates distally at a grasping member or end 150A having a circumferential distal edge defining a transverse distal tip 154A. The inner member 138 is connected proximally to a collar or retaining ring 139 secured to a proximal leg 164B of handle 140. The inner member 138 is hollow or tubular and has a proximal end extending proximally of collar 139. The proximal end of the inner member 138 carries a knob 141 for rotating the inner member relative to the outer member, a valve, such as a stopcock 143, for controlling fluid flow through the inner member and a connector 145, which may be a unipolar or bipolar electrical connector, for supplying energy, such as electric, laser, ultrasound and cryogenic energy, through the inner member such as for coagulation and cautery, for example. The grasping instrument 116 can be provided with an additional connection for transmission or application of energy to treat or cut anatomical tissue, such a connection being represented by the connector 145' on inner member 138. Handle 140 is similar to handle 40 except that the distal and proximal legs 164A and 164B of handle 140 are each provided with a finger ring 165 to facilitate operation of the handle 140. The handle 140 can be provided with a releasable locking mechanism 147 for locking the handle 140 in a compressed or squeezed position, the locking mechanism 147 comprising a pair of curved locking arms or bars 149 extending from base 166. The locking arms 149 carry cooperatively engageable locking structure 151 for locking engagement when the handle 140 is moved to a compressed position.

Handle 140 in the rest position positions the distal tip 154A of grasping member 150A in contact with or close to the distal tip 154B of grasping member 150B such that the recess of grasping member 150B is closed or occupied by the grasping member 150A and cannot accommodate anatomical tubular structure therein as shown in FIG. 17. When it is desired to utilize grasping instrument 116 to pick up or grasp anatomical tubular structure, the handle 140 is gripped via finger rings 165 and is spread causing the tips 154A and 154B to be moved away from one another to open the recess. Accordingly, when the grasping members 150A and 150B are in the open position, a Fallopian tube F can be received in the grasping space 160 defined between the distal tips 154A and 154B with the Fallopian tube extending in a direction transverse to a longitudinal axis of the inner member 138 as shown in FIG. 18. The distal tips 154A and 154B can be formed or provided with cutting edges 157A and 157B, respectively, such that release of the spreading force on handle 140 causes the grasping members to move toward the closed position such that the Fallopian tube F received between the distal tips will be cut by the cutting edges. Accordingly, grasping instrument 116 is representative of a grasping instrument in which the grasping members also constitute the cutting members.

The handle 140 is also designed for squeezing operation allowing the grasping members 150A and 150B to be moved to a further, more tightly closed position wherein the distal tips 154A and 154B engage one another more tightly or with greater force. The grasping members 150A and 150B can be used to grasp a straight or a curved needle between tips 154A and 154B in the further closed position, and the needle can be manipulated by rotating the inner member 138 via knob 141. The grasping instrument 116 can be utilized to pick up and hold the Fallopian tube F and draw it into a loop formation as described for grasping instrument 16. If desired, the Fallopian tube or other anatomical tissue can be held in the grasping space 160 via a suction force applied through the inner member 138. It should be appreciated that the grasping instrument 116 can be utilized to apply a clip to the Fallopian tube in which case the distal tips 154A and 154B can be formed with clip engaging walls having grooves for receiving legs of a clip in the open position, the grasping members 150A and 150B serving to close the clip when moved toward the closed position as disclosed in applicant's U.S. Pat. No. 5,171,250, the disclosure of which is incorporated herein by reference. It should be appreciated that the handle 140 can be locked in a spread position by modifying locking mechanism 147 or by providing the handle 140 with a locking mechanism of the type disclosed in Ser. No. 08/694,385 incorporated herein by reference.

Figure 19:
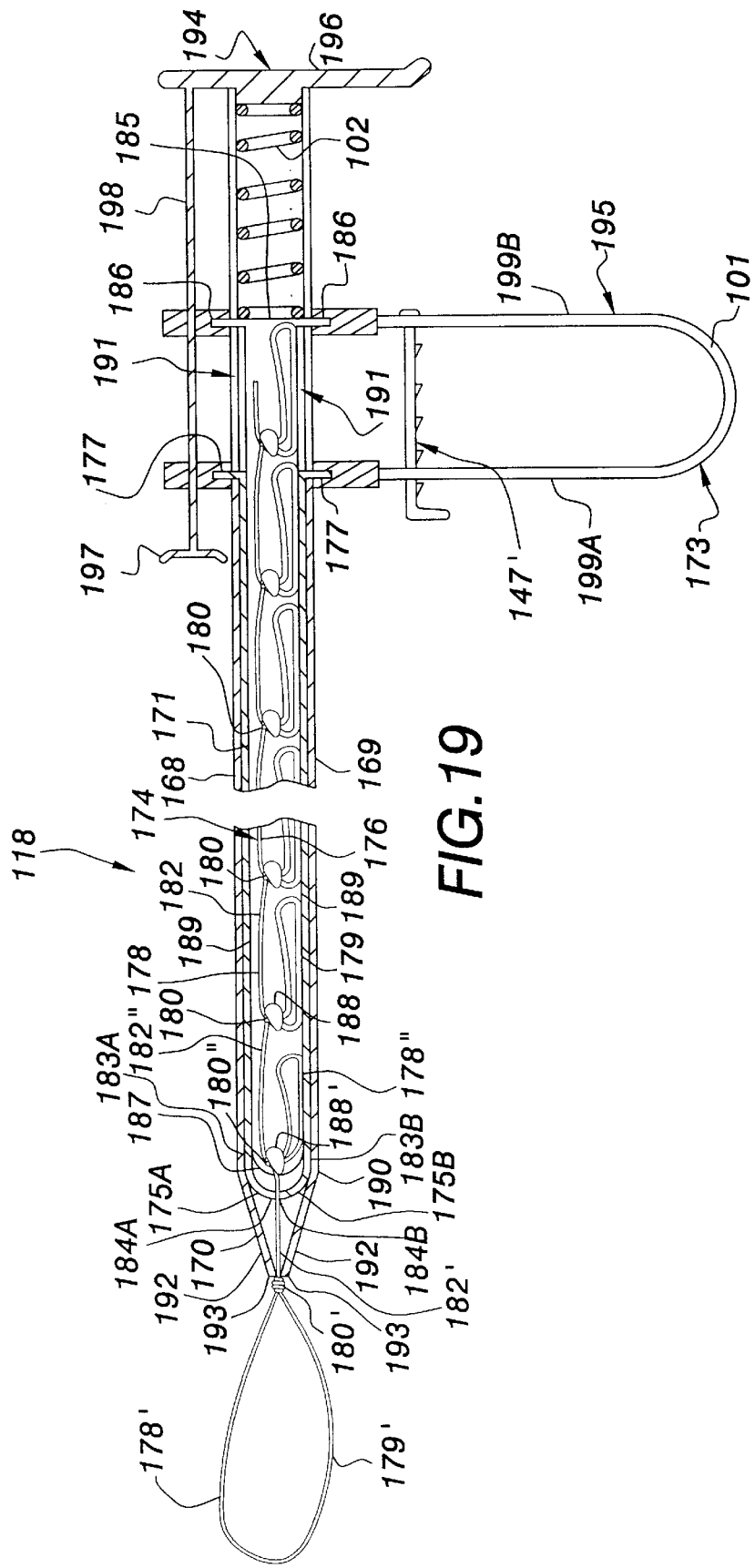
FIG. 19 is a broken side view, partly in section, of a modification of a ligating instrument for the endoscopic tubal ligation instrument assemblies and/or methods of endoscopic tubal ligation according to the present invention.

A modification of a ligating instrument for use in the endoscopic tubal ligation instrument assemblies and/or methods of endoscopic tubal ligation of the present invention is illustrated at 118 in FIG. 19 and comprises a ligating instrument of the type disclosed in applicant's prior patent application Ser. No. 08/694,385 incorporated herein by reference. Ligating instrument 118 includes an elongate tubular member or knot pusher 168, an engaging member or jaw member 169 disposed in tubular member 168, a deployer or actuator 171 slidably disposed in engaging member 169, a handle 173 coupled with engaging member 169, actuator 171 and tubular member 168 and a ligature supply 174 having multiple ligature loops 178 disposed within engaging member 169. The engaging member 169 comprises a tubular or hollow elongate cylindrical body and a pair of opposed jaws or flaps 175A and 175B at a forward or distal end of the engaging member body. The engaging member body terminates proximally at an open proximal end configured or provided with ears 177 coupled with handle 173. The jaws 175A and 175B include pivot, joint or hinge segments 183A and 183B, respectively, merging with and pivotally, resiliently or flexibly connecting the jaws to the engaging member body. Jaws 175A and 175B are disposed in a closed, grasping, holding or engaging position wherein a space, opening or passage is defined between forward edge segments 184A and 184B of jaws 175A and 175B, respectively, for receiving a length of filamentous ligature material 176 of ligature supply 174 while preventing ligature loops 178 of ligature supply 174 from passing therebetween. The forward edge segments 184A and 184B are sharpened to present cutting edges for cutting the length of ligature material 176 passing between the jaws when the ligating instrument is pivoted, angled or tilted as explained further below. Jaws 175A and 175B are movable outwardly away from one another from the grasping position to an open, non-engaging, non-holding or non-grasping position by engagement of a distal end of actuator 171 with the jaws when the actuator is moved longitudinally relative to the engaging member. When moved to the open position, the jaws rotate or pivot about hinge segments 183A and 183B, respectively, in a direction away from the longitudinal axis of the engaging member. Accordingly, in the open position, the jaws 175A and 175B are disposed further away from one another and, therefore, are disposed further away from the engaging member longitudinal axis, than they are in the grasping position. The distance between the jaws in the open position is greater than the distance between the jaws in the grasping position and is large enough to permit passage therebetween of the ligature loops 178. The jaws can be designed in many various ways to be maintained in or biased toward the grasping position and to be movable to the open position. For example, jaws 175A and 175B can be made partly or entirely of resilient, flexible or spring materials, such as materials having shape memory, to flexibly, resiliently and/or spring bias the jaws toward the grasping position, to allow the jaws to pivot, rotate or deform from the grasping position to the open position in response to engagement with actuator 171 and to automatically return, move or restore the jaws to the grasping position in response to disengagement with actuator 171.

The actuator 171 comprises an elongate actuator plate terminating proximally at a transverse or perpendicular end wall or flange 185 bent or angled from the plane of the actuator plate and configured or provided with protruding ears 186. The actuator plate terminates distally at a distal end defined by an arcuate or convex edge 187. The actuator 171 is disposed in the lumen or hollow interior of the engaging member 169 such that a plane containing the actuator plate is offset from and not aligned with the longitudinal axis of the engaging member such that the actuator plate is disposed in the engaging member lumen off-center or slightly to one side of the engaging member. The actuator and the engaging member are movable longitudinally relative to one another. The ears 186 are spaced 180° from one another and are laterally offset from the plane of the actuator plate to be longitudinally aligned with ears 177, respectively, when the actuator is disposed in the engaging member. A plurality of retention members or fingers 188 are disposed on an inner face of the actuator plate. The retention members 188 are longitudinally aligned with one another along the actuator plate and are centrally disposed between lateral edges 189 of the actuator plate. Each retention member 188 defines a distally facing mouth communicating with a pocket or recess defined between the retention member and the inner face of the actuator plate. The pockets or recesses are of a size to receive knots 180 of the ligature loops of ligature supply 174.

Tubular member or pusher 168 comprises a tubular or hollow, elongate, cylindrical body terminating distally at tapered distal end 170, the tapered distal end 170 being joined to the cylindrical body at a circumferential or peripheral junction 190. The pusher body terminates proximally at an open proximal end mounted to a finger grip of handle 173 as explained further below. A pair of longitudinally extending slots 191 are formed in the pusher body at 180° spaced locations, the slots 191 extending distally from the proximal end of the pusher body. The slots 191 have a length to permit longitudinal movement of the pusher 168 distally and proximally relative to the engaging member 169 and to permit longitudinal movement of the actuator 171 relative to the engaging member 169 during use. A distal portion of the pusher 168 is slit or cut at spaced locations about a longitudinal axis of the pusher, the slits or cuts extending longitudinally along the pusher to form a plurality of push fingers 192 having distal tips 193. The distal portion of the pusher 168 is disposed in a normal, contracted or closed position wherein the distal tips 193 of the push fingers 192 are disposed close to one another and close to the pusher longitudinal axis while being separated slightly from one another by a distance allowing passage of the length of ligature material 176 between the distal tips 193 while preventing passage of the knots 180 therebetween. The distal portion of the pusher is movable from the contracted position to an expanded or open position wherein the push fingers 192 are spread outwardly away from one another in a direction away from the longitudinal axis of the pusher. In the expanded position, the distal tips 193 of the push fingers are disposed further away from one another and further away from the pusher longitudinal axis than they are in the contracted position; and, accordingly, the ligature loops 178 of the ligature supply 174 can pass therebetween. The distal portion of the pusher can be designed in many ways, such as being made of resilient, flexible or spring materials including materials having shape memory, to be normally disposed in the contracted position and to be movable to the expanded position and back to the contracted position.

Handle 173 includes a finger grip 194 and a U-shaped hand grip 195. The finger grip 194 includes a proximal or rearward push button or knob 196 mounted to the proximal end of the pusher body and a distal or forward push button or knob 197 coupled with the proximal push button by an arm 198. The pusher 168 is attached to the finger grip 194 for movement therewith. Arm 198 extends between proximal push button 196 and distal push button 197, the arm 198 being spaced laterally from the pusher body on a side thereof opposite the hand grip 195.

The hand grip 195 includes a forward leg 199A and a rearward leg 199B connected to one another by a curved base 101. A free end of leg 199A is connected to a retention ring or collar having recesses therein receiving ears 177 of the engaging member 169. A free end of leg 199B is similarly connected to a retention ring or collar having recesses therein receiving ears 186 of the actuator 171. The curved base 101 maintains the hand grip 195 and, therefore, the ligating instrument 118, in a rest position wherein the actuator 171 is in a neutral longitudinal position with the jaws 175A and 175B in the closed position. The hand grip 195 is made entirely or partly of resilient, flexible or spring materials, such as materials having shape memory, allowing the hand grip 195 to be manually squeezed or compressed via the legs 199A and 199B for movement from the rest position to a compressed or squeezed position and allowing the hand grip to return automatically to the rest position when the manual squeezing or compressive force is removed. The hand grip 195 includes a locking mechanism 147' for locking the hand grip 195 in a compressed or squeezed position, the locking mechanism 147' being of the type described in the prior application Ser. No. 08/694,385 incorporated herein by reference.

The knotting element pusher 168 slidably passes through the retention rings, respectively, with the ears 177 of the engaging member and the ears 186 of the actuator slidably disposed in the slots 191 of the pusher body and the arm 198 slidably passing through apertures in the retention rings, respectively. A helical coil spring 102 is disposed in the pusher body and is mounted between the end wall 185 of the actuator and a protrusion of proximal push button 196 to bias the pusher 168 longitudinally to an initial longitudinal position as shown in FIG. 19 wherein the distal tips 193 are disposed distally of jaws 175A and 175B with the distal portion of the pusher 168 in the contracted position and the actuator 171 in the neutral position.

The ligature supply 174 comprises the length of ligature material 176 having a plurality of pre-formed, interconnected, variable size or contractible ligature loops 178. Each ligature loop 178 includes a loop segment 179 of the ligature material and a knot 180 movable along the ligature material in a direction to contract or reduce the size of the loop segment 179 around anatomical structure to form a ligature. The ligature loops 178 are disposed at spaced locations along the length of ligature material 176 such that connecting segments 182 of the length of ligature material extend between adjacent ligature loops. The knots 180 are of a size preventing passage of the knots and, therefore, the ligature loops, between the forward edge segments 184A and 184B of the jaws when the jaws are in the grasping position and permitting passage of the ligature loops, including the knots thereof, between the forward edge segments when the jaws are in the open position. The knots 180 are of a size preventing passage of the knots and, therefore, the ligature loops, between the distal tips 193 when the distal portion of the pusher 168 is in the contracted position and permitting passage of the ligature loops 178, including the knots thereof, between the distal tips 193 when the distal portion of the pusher is in the expanded position. The length of ligature material 176 comprises a bioabsorbable filament having an external diameter or cross-sectional size permitting passage of the filament between the forward edge segments 184A and 184B when the jaws are in the grasping position and permitting passage of the filament between the distal tips 193 when the distal portion of the pusher is in the contracted position. The ligature supply 174 is disposed in the lumen of the engaging member 169 with the knots 180 releasably retained, held, captured or engaged by retention members 188, respectively. The ligature supply 174 is carried or advanced distally relative to the engaging member 169 when the actuator 171 is moved longitudinally, distally from the neutral position.

Prior to use, the ligating instrument 118 will be in the condition shown in FIG. 19 with the pusher 168 disposed in the initial longitudinal position and the actuator 171 disposed in the neutral longitudinal position. Accordingly, the jaws 175A and 175B will be disposed in the grasping position and the distal portion of the pusher 168 will be disposed in the contracted position with the distal tips 193 thereof disposed distally of the jaws. The finger grip 194 is biased relative to the hand grip 195 by spring 102 to position the pusher 168 in the initial position with the proximal push button 196 spaced proximally from leg 199B and the distal push button 197 spaced distally from leg 199A. The hand grip 195 will be disposed in the rest position to maintain the neutral position for the actuator 171.

In order to form a ligature in anatomical tubular structure such as the Fallopian tube with ligating instrument 118, the first ligature loop 178' disposed externally of the pusher 168 is contracted around of the Fallopian tube by depressing the proximal push button 196 distally causing the pusher 168 to be moved longitudinally, distally relative to the engaging member 169 from the initial longitudinal position to an extended longitudinal position as permitted by slots 191 in the pusher body. The hand grip 195 remains in the rest position such that the engaging member 169 and the actuator 171 do not move relative to one another. Distal movement of the pusher 168 from the initial position causes the distal tips 193 of the push fingers 192 to move the knot 180' of the ligature loop 178' distally to contract the loop segment 179' around the Fallopian tube to form a ligature. The manual force applied by the surgeon to the proximal push button 196 can be controlled to obtain a desired tension or tightness for the contracted loop segment, and the surgeon can tactilely sense or feel contraction of the loop segment for controlled tensioning. Once the ligature has been formed with desired tension around the Fallopian tube, the proximal push button 196 is released causing the pusher 168 to return to the initial position due to the bias of spring 102. The Fallopian tube is then cut or severed proximally of the ligature and the cut segment is removed from the patient's body for biopsy.

Once the bend or knuckle of the Fallopian tube has been cut and a specimen collected for biopsy, the distal push button 197 is manually depressed in the proximal direction causing the pusher 168 to move longitudinally, proximally relative to the engaging member 169 and the actuator 171 from the initial longitudinal position to a retracted longitudinal position. Movement of the pusher 168 to the retracted position causes the distal portion of the pusher to flex or deform due to engagement of the push fingers 192 with the jaws 175A and 175B. Accordingly, the distal portion of the pusher 168 is moved from the contracted position to the expanded position, and the jaws 175A and 175B will protrude distally beyond the distal tips 193 of the push fingers. Accordingly, the sharpened edge segments 184A and 184B of the jaws will be exposed at the distal end of the instrument 118, and the instrument 118 is pivoted, angled or tilted laterally via manipulation of the handle 173 causing the connecting segment 182' between the ligature loop 178' and the next proximal ligature loop to be cut or severed to separate the ligature from the remainder of the ligature supply.

In order to deploy the next ligature loop externally of the instrument body, the pusher 168 is maintained in the retracted position, and the hand grip 195 is squeezed or compressed to move the actuator 171 longitudinally, distally relative to the engaging member 169 from the neutral longitudinal position to an extended or deployed longitudinal position. Distal movement of the actuator 171 causes the lateral edges 189 of the actuator to engage inner surfaces of the jaws 175A and 175B such that the jaws are moved from the grasping position to the open position. The actuator 171 is moved far enough distally to pass through the jaws 175A and 175B, and the ligature supply 174 is carried or advanced distally with the actuator. Accordingly, the distalmost retention member 188' and the ligature loop 178" held thereby are positioned externally of the jaws 175A and 175B.

When the hand grip 195 is released, the actuator 171 automatically returns to the neutral position while the ligature supply 174 remains in the advanced position such that the actuator 171 moves proximally relative to the ligature supply 174. Accordingly, each knot 180 is released, disengaged or freed from the retention member 188 that previously held it. Movement of the actuator 171 from the extended position to the neutral position causes the jaws 175A and 175B to return automatically to the grasping position, and the next ligature loop 178" will be disposed externally of the jaws with its connecting segment 182" held thereby. Once the actuator 171 has returned to the neutral position, the proximal force on distal push button 197 is removed causing the pusher 168 to automatically return to the initial position with the distal portion thereof in the contracted position and the distal tips 193 of the push fingers 192 disposed proximally of the knot 180" of the now externally deployed ligature loop for use in forming another ligature.

Figure 20:
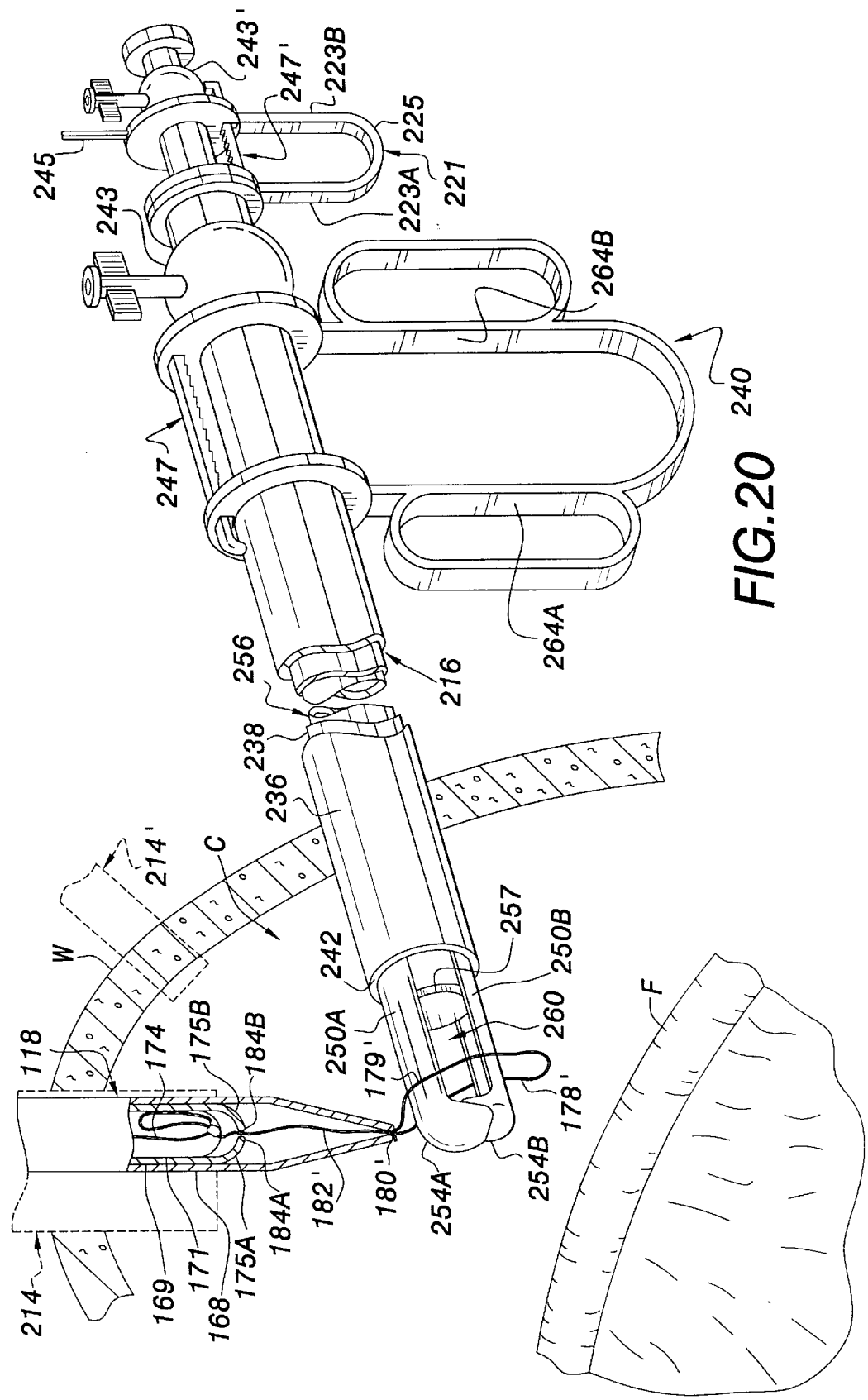
FIG. 20 is a broken perspective view, partly in section, illustrating use of the ligating instrument of FIG. 19 and another modification of a grasping instrument in a multiple port endoscopic tubal ligation procedure according to the present invention.

FIG. 20 illustrates at 216 another modification of a grasping instrument for use in the endoscopic tubal ligation instrument assemblies and/or methods of endoscopic tubal ligation according to the present invention. Grasping instrument 216 is similar to grasping instrument 16 except that grasping instrument 216 includes a cutting member 256 disposed in inner member 238, handle 240 for grasping instrument 216 is different than that for grasping instrument 16, and the grasping members 250A and 250B for grasping instrument 216 are maintained in the closed position in the rest position for handle 240. Grasping instrument 216 includes outer member 236 having a distal end 242 and a proximal end connected to a distal leg 264A of handle 240. Inner member 238 is disposed in outer member 236 and includes grasping members 250A and 250B and a proximal end coupled with a proximal leg 264B of handle 240. Handle 240 is similar to handle 140 and serves to maintain the grasping instrument 216 in a rest position wherein the grasping members 250A and 250B, which are biased to an open position, are constrained by the outer member 236 to be maintained in the closed position as shown in FIG. 20. Accordingly, when the handle 240 is compressed or squeezed, the grasping members 250A and 250B will be released for movement to the open position.

Grasping instrument 216 includes cutting member 256 disposed within the inner member 238. The cutting member 256 comprises an elongate tubular member having a distal circumferential cutting edge or blade 257 and having a proximal end mounted to a hand grip 221. Hand grip 221 is a U-shaped hand grip 221 having a distal leg 223A and a proximal leg 223B connected to one another by a curved base 225. The proximal leg 223B is connected to the cutting member 256, and the distal leg 223A is connected to the inner member 238. The hand grip 221 is made partly or entirely of resilient, flexible or spring materials, such as materials having shape memory, to resiliently or flexibly bias the cutting member to a longitudinally retracted or non-cutting position as shown in FIG. 20. In the non-cutting position, the cutting edge 257 is disposed proximally of the tips 254A and 254B of the grasping members to define a grasping space 260 between the tips and the cutting edge. The proximal leg 223B of hand grip 221 can be depressed or moved distally in the direction of handle 240 to move the cutting member 256 distally relative to the inner member 238 to cut a Fallopian tube F within the grasping space 260 as explained further below. The handle 240 can be provided with a releasable locking mechanism 247, similar to the locking mechanism 47, for locking the handle 240 in a compressed or squeezed position and/or a spread position and the hand grip 221 of cutting member 256 can be provided with a similar releasable locking mechanism 247'. The cutting member 256 can have an electrical connection 245 for supplying electric current via cutting member 256. The inner member 238 can communicate with a valve 243 for supplying fluid to the anatomical cavity between the inner member 238 and cutting member 256, and the cutting member 256 can be provided with a valve 243' for irrigation and/or aspiration and/or the introduction of instruments therethrough. Suction can be applied through the cutting member 256 for aspiration and a cut segment of the Fallopian tube or other tissue can be removed from the body via such suction. In addition, instruments, such as a needle for delivering anesthetics, can be introduced in the anatomical cavity through the cutting member 256 and its valve 243'.

FIG. 20 illustrates use of the grasping instrument 216 and the ligating instrument 118 in a multiple port procedure of endoscopic tubal ligation. A distal end of the grasping instrument 216 is introduced in the abdominal cavity C through a first port in cavity wall W, and a distal end of ligating instrument 118 is introduced in the abdominal cavity C through a second port or opening in cavity wall W. The grasping instrument 216 and the ligating instrument 118 can be introduced in the abdominal cavity through portal sleeves or cannulas (not shown), respectively, extending through the cavity wall W. Either the grasping instrument 216 or the ligating instrument 118 can be assembled with an endoscope to form an endoscopic tubal ligation instrument assembly for a two port procedure. For example, the endoscope and the grasping instrument or the endoscope and the ligating instrument can be assembled in a barrel as discussed for instrument assembly 10, the grasping instrument or the ligating instrument can be arranged in a channel of the endoscope, or the endoscope can be arranged within the grasping instrument or the ligating instrument. In a three or more port procedure, the grasping instrument and the ligating instrument are introduced through the first and second ports, respectively, and the endoscope is introduced through a third port. FIG. 20 illustrates in dotted lines an endoscopic 214 forming an instrument assembly with ligating instrument 118, the ligating instrument 118 being disposed in a channel of the endoscope 214 for a two port procedure. FIG. 20 also illustrates in dotted lines an endoscope 214' introduced through a third port with the grasping instrument 216 introduced through the first port and the ligating instrument 118 introduced through the second port for a three port procedure, in which case the ligating instrument is introduced in the second port without the endoscope 214.

Once the endoscope, grasping instrument 216 and ligating instrument 118 have been introduced in the abdominal cavity C, the handle 240 is manually compressed or squeezed, externally of the abdominal cavity, to move the grasping members 250A and 250B to the open position. The grasping member 250B is utilized to pick up and lift the Fallopian tube F. The grasping members 250A and 250B are returned to the closed position by releasing handle 240 such that the Fallopian tube F is held therebetween. The grasping instrument 216 is manipulated to draw the Fallopian tube F into a loop formation through the ligature loop 178' as shown in FIG. 21.

Once the ligature loop 178' is properly positioned around the loop formation of Fallopian tube F, the proximal push button of ligating instrument 118 is depressed causing the pusher 168 to be moved distally. The pusher 168 moves the knot 180' of the ligature loop 178' in a direction to contract or reduce the size of the loop segment 179' around the loop formation of the Fallopian tube as shown in FIG. 22. The proximal push button is depressed far enough distally to contract the loop segment to form a ligature of desired tension. The proximal push button of the ligating instrument 118 is released once the ligature has been formed to the desired tension.

With the bend of the Fallopian tube F held between the grasping members, the proximal leg 223B of the hand grip 221 of the cutting member 256 is depressed causing the cutting member 256 to be moved distally, longitudinally relative to the outer member 236 and inner member 238 causing the cutting edge 257 at the distal end of the cutting member 256 to be moved through the segment of Fallopian tube F disposed between the grasping members 250A and 250B. Accordingly, the Fallopian tube F will be cut as shown in FIG. 23 for removal of the Fallopian tube segment from the patient's body for identification via biopsy, the cut segment being contained in cutting member 256.

Once the Fallopian tube has been cut, the distal push button of the ligating instrument 118 is depressed to move the pusher 168 proximally relative to the engaging member 169 such that the distal portion of the pusher 168 is moved to the expanded position to expose the cutting edges 184A and 184B of the jaws 175A and 175B. The ligating instrument 118 is angled or tilted to cut the connecting segment 182' extending proximally from the ligature loop 178' to the next ligature loop 178" as shown in FIG. 23.

The hand grip of the ligating instrument 118 is squeezed while the distal push button remains in the depressed position to advance the ligature supply 174 distally to position the next ligature loop 178" externally of the pusher 168. Once the next ligature loop 178" is externally deployed by the actuator 171, the distal push button and the hand grip of the ligating instrument are released causing the pusher 168 to return to the initial position with the knot 180" of the now externally deployed ligature loop 178" disposed distally thereof with the ligating instrument ready to be used to form another ligature as shown in FIG. 24.

FIG. 25 illustrates at 316 a modification of a grasping instrument for use in the endoscopic tubal ligation instrument assemblies and/or methods of endoscopic tubal ligation according to the present invention. Grasping instrument 316 is similar to grasping instrument 216 except that the outer member 336 of grasping instrument 316 functions as the cutting member for the grasping instrument 316. The grasping instrument 316 includes outer member 336 and inner member 338 slidably disposed in outer member 336 and carrying or formed with grasping members 350A and 350B. The grasping instrument 316 can be provided with any suitable handle for moving the outer member 336 and/or the inner member 338 longitudinally relative to one another.

The distal end 342 of the outer member 336 tapers to a circumferential cutting edge 357. The grasping members 350A and 350B are biased to be normally disposed in an open position as shown in FIG. 25 and are movable to a closed position in response to longitudinal movement of the outer and/or inner members. In the open position, the distal tips 354A and 354B of the grasping members are separated from one another to allow a Fallopian tube F or other anatomical tissue to be received between the grasping members 350A and 350B as shown in FIG. 25; and, in the closed position, the tips 354A and 354B overlap one another to capture the Fallopian tube F or other anatomical tissue in the grasping space 360 as shown in FIG. 26. The tip 354B of the lower grasping member 350B can have a round or spoon shape. It is preferred that the tip 354B be disposed within or inside of the tip 354A of the upper grasping member 350A when the tips 354A and 354B overlap one another in the closed position.

Movement of the grasping members 350A and 350B to the closed position is accomplished via distal longitudinal movement of the outer member 336 and/or proximal longitudinal movement of the inner member 338 such that the grasping members are disposed partly within the outer member 336. Continued relative longitudinal movement of the outer and/or inner members causes the grasping members 350A and 350B to be disposed further within the outer member 336, and the cutting edge 357 will contact the Fallopian tube F and cut the segment of Fallopian tube F disposed in the grasping space as shown in FIG. 27. Further relative longitudinal movement of the outer and/or inner members causes the grasping members 350A and 350B to be completely retracted within the outer member 336 as shown in FIG. 28, and the cut segment of the Fallopian tube F will be disposed within the outer member for removal externally of the patient's body. The grasping members 350A and 350B are provided with bumps or protrusions 331 to facilitate movement of the grasping members to the closed and further closed positions due to engagement with outer member 336.

Another modification of a grasping instrument for use in the instrument assemblies according to the present invention is illustrated at 416 in FIG. 29, the grasping instrument 416 including a selectively extendable needle 404. Grasping members 450A and 450B are similar to grasping members 250A and 250B except that grasping members 450A and 450B have a semi-circular configuration in cross-section cooperating to form a circular cross-sectional configuration in the closed position. The distal tips 454A and 454B of the grasping members 450A and 450B, respectively, are defined by partial spherical walls to form a semi-spherical nose at the distal end of the grasping members in the closed position. A semi-circular recess is formed in the distal tip of each grasping member and the recesses cooperate to form a circular hole or aperture 405 through the tips of the grasping members in the closed position. Grasping member 450B includes cutting edges 457B extending parallel to one another along opposed lateral sides, respectively, of grasping member 450B. Grasping member 450A includes cutting edges 457A parallel to one another and inwardly spaced from cutting edges 457B as shown in FIG. 31. Accordingly, when the grasping members 450A and 450B are in the closed position shown in FIG. 29, the cutting edges 457B overlap the cutting edges 457A, such that the grasping members are also the cutting members for the grasping instrument 416.

Handle 440 for grasping instrument 416 is the same as handle 240 and includes a distal leg 464A connected to the outer member 436 and a proximal leg 464B connected to the inner member 438 for moving the outer member 436 proximally and/or the inner member 438 distally. The handle 440 in the rest position maintains the grasping members 450A and 450B in the closed position constrained by the outer member 436 as shown in FIG. 29. Handle 440 is squeezable or compressible to move the grasping members 450A and 450B to the open position and is provided with a releasable locking mechanism 447 for locking the handle in a desired compressed or squeezed position. The inner member 438 can communicate with a valve 443 for controlled fluid flow through the inner member and/or for sealing engagement with other instruments introduced through the inner member when the needle is withdrawn.

Needle 404 is hollow or cannulated and has an angled or beveled distal end 406 and a proximal end coupled with a proximal leg 423B of a hand grip 421. Hand grip 421 is the same as hand grip 221 and includes proximal leg 423B and a distal leg 423A connected to the inner member 438. The needle is disposed within the inner member 438 in axial alignment with the hole 405. The hand grip 421 maintains the needle 404 in a retracted position wherein the distal end 406 is disposed proximally of and does not protrude through the hole 405 as shown in FIG. 29. Hand grip 421 is squeezable or compressible to move the needle 404 distally relative to the inner member 438 for movement from the retracted position to an extended position as shown in FIG. 30. In the extended position, the distal end 406 of needle 404 is disposed distally of the distal tips 454A and 454B of the grasping members with the needle protruding through the hole 405. The extent to which the hand grip 421 is compressed or squeezed controls the distance that the needle 404 protrudes from the grasping members, and the hand grip 421 is provided with a releasable locking mechanism 447' for locking the handgrip 421 in a compressed or squeezed position, the locking mechanism 447' being similar to locking mechanism 447. The needle 404 can communicate with a valve 443' for controlling fluid flow through the needle. The needle 404 can be provided with a connection 445 for transmitting electrical, laser or ultrasound energy through the needle for treating anatomical tissue. Since the needle 404 can be extended distally beyond the grasping members in the closed position as shown in FIG. 30, the needle 404 can be utilized to introduce fluids, such as anesthetics and other medicaments, into the anatomical cavity and/or into the Fallopian tubes, and/or the needle can be utilized to aspirate fluids from the anatomical cavity. As shown in FIG. 31, the grasping members 450A and 450B can be moved to the open position with the needle 404 in either the retracted or extended position. Where the grasping members 450A and 450B are moved to the open position to receive anatomical tubular structure therebetween with the needle 404 in the retracted position, the needle can thereafter be moved to the extended position to penetrate the anatomical tubular structure disposed between the grasping members, and the needle can be utilized to inject anesthetic into the anatomical tubular structure. The handle 421 can be removably connected to inner member 438 allowing the needle to be withdrawn from the inner member.

The endoscopic tubal ligation instrument assemblies can be utilized to perform various diverse functions and procedures in addition to grasping, ligating and cutting. The grasping instruments can serve as clip appliers as well as needle holders, for example. The instrument assemblies can have a needle for treating various pathology, such as ovarian cysts, lysis of adhesion and inflamed gall bladder incidental to an endoscopic tubal ligation procedure. For example, an ovarian cyst or the gall bladder can be punctured or opened with needle 404, and fluids can be aspirated or sucked out of the cyst or gall bladder through needle 404. The ligating instrument of the instrument assembly can be used to tie off or seal the cyst or gall bladder prior to puncturing by contracting a ligature loop therearound. Various pathologies, including lysis of adhesion, can be treated by fluid injection, electrical coagulation and cautery performed with the instrument assemblies; for example, fluid injection, electrical coagulation and cautery can be performed with the grasping instrument. Where the pathologies are discovered during an endoscopic tubal ligation procedure, the instrument assemblies can be used to treat the pathologies incidental to the tubal ligation procedure without the need for additional instruments.

FIG. 32 illustrates at 516 another modification of a grasping instrument for use in the endoscopic tubal ligation instrument assemblies. Grasping instrument 516 is similar to grasping instrument 416 except that grasping members 550A and 550B for grasping instrument 516 curve in a direction away from a longitudinal axis of the inner member 538, and the handle 540 for grasping instrument 516 differs from that of grasping instrument 416. Grasping members 550A and 550B include teeth or serrations 507 along inner grasping edges thereof disposed distally of cutting edges 557A and 557B, respectively. Cutting edge 557A for grasping member 550A protrudes inwardly beyond the grasping edge thereof. The grasping edge for grasping member 550B protrudes inwardly beyond the cutting edge 557B thereof. When the grasping members are moved from the open position shown in FIG. 32 to the closed position shown in FIG. 33, the cutting edges 557A and 557B contact one another to cut anatomical tubular structure disposed between the cutting edges. The grasping members 550A and 550B are normally disposed in the open position and are moved to the closed position in response to longitudinal movement of the outer member 536 distally and/or longitudinal movement of the inner member 538 proximally, with movement of the grasping members to the closed position being facilitated by bumps 531 on the grasping members. The bumps 531 are contacted or engaged by the outer member 536 forcing the grasping members to be moved to the closed position.

Handle 540 includes a leg 564A disposed on one side of inner member 538 and a leg 564B disposed on an opposite side of inner member 538. Distal ends of legs 564A and 564B are connected to a collar 544 at a proximal end of outer member 536, and proximal ends of legs 564A and 564B are connected to a collar 541 secured to inner member 538. The inner member 538 extends proximally from the outer member 536 such that the collar 541 is spaced proximally from the collar 544. The legs 564A and 564B protrude outwardly from the longitudinal axis of the inner member 538 in a normal, relaxed or non-compressed position corresponding to the rest position. Handle 540 is made partly or entirely of resilient, flexible, or spring materials, such as materials having shape memory, to maintain the handle 540 in the rest position with the grasping members 550A and 550B disposed in the open position with bumps 531 disposed distally of a distal end of outer member 536. The legs 564A and 564B are movable inwardly toward one another, i.e. in the direction of the inner member longitudinal axis, via squeezing or compressive operation of handle 540 to move the outer member 536 and/or the inner member 538 longitudinally relative to the other causing the grasping members 550A and 550B to be moved from the open position to the closed position. The handle 540 can include finger rings 565 protruding outwardly from legs 564A and 564B, respectively, as shown in dotted lines in FIG. 32. The inner member 538 can be coupled with a valve 543 for controlled fluid flow through the inner member and/or for sealing engagement with instruments introduced through the inner member. The handle 540 can be provided with a releasable locking mechanism 547, similar to locking mechanism 147, for locking handle 540 in a compressed position, the locking mechanism 547 being laterally offset from and along side the inner member.

FIG. 33 illustrates an instrument assembly 510 comprising grasping instrument 516, ligating instrument 118 and an endoscope 514 receiving grasping instrument 516 and ligating instrument 118. Endoscope 514 is illustrated in FIG. 34 and includes an elongate body 530 having an observation window 532 at a distal end thereof and provided or formed with three channels 524A, 524B and 524C extending longitudinally therethrough. A plurality of light transmitting fibers 526 are disposed within the lumen of endoscope body 530 to provide illumination at the distal end of the endoscope. The grasping instrument 516 is disposed in channel 524A of endoscope 514 and the ligating instrument 118 is disposed in channel 524B of endoscope 514. The channel 524C of endoscope 514 can be utilized to introduce additional instruments through the endoscope 514 and/or for aspiration and/or irrigation as needed. Ligating instrument 118 is disposed within the channel 524B with the distal end 170 of the knot pusher 168 protruding distally beyond the distal end of the endoscope 514. The grasping instrument 516 is disposed in channel 524A with the grasping members 550A and 550B protruding distally beyond the distal end of the endoscope 514 and curving inwardly toward the ligating instrument 118. The grasping members 550A and 550B are initially disposed in the closed position due to engagement of a distal end of outer member 536 with bumps 531, the closed position being maintained by locking the handle 540 in a compressed or squeezed position with locking mechanism 547. The grasping members 550A and 550B protrude through the externally deployed ligature loop 178' of ligating instrument 118. The grasping instrument 516 and/or the ligating instrument 518 are movable longitudinally relative to endoscope 514, and the grasping instrument 516 and the ligating instrument 518 can move longitudinally relative to one another.

Use of the instrument assembly of FIG. 33 to ligate anatomical tubular structure is similar to that described above in that, after introduction of a distal end of the instrument assembly at an internal operative site, the handle 540 is unlocked and released for movement to the rest position corresponding to the open position for the grasping members 550A and 550B. The grasping members 550A and 550B are positioned to receive anatomical tubular structure such as a Fallopian tube between the grasping edges thereof and are utilized to draw the anatomical tubular structure into a loop formation through ligature loop 178'. It should be appreciated that the anatomical tubular structure can be picked up and drawn through the loop 178' without moving the grasping members to the closed position and that the anatomical tubular structure can be grasped and drawn through the loop 178' with the grasping members 550A and 550B in either the closed or open positions. The amount of pressure or force that the grasping members exert on the anatomical tubular structure in the closed position can be controlled by controlling the extent to which the handle 540 is compressed or squeezed. The anatomical tubular structure is drawn through the ligature loop 178', and the finger grip of the ligating instrument 118 is operated to move the knot pusher 168 distally to contract the ligature loop 178' around the anatomical tubular structure to form a ligature. Where cutting of the anatomical tubular structure is necessary to obtain a tissue sample or to sever the anatomical tubular structure proximally of the ligature, the anatomical tubular structure is received between the cutting edges 557A and 557B of grasping members 550A and 550B. The grasping members 550A and 550B are moved to the closed position to cut the anatomical tubular structure between the cutting edges. The ligating instrument 118 is utilized to cut the connecting segment 182' of ligature material extending from the ligature loop 178' to the next ligature loop and to advance the next ligature loop externally of the pusher 168 as described above.

Figures 35, 36:
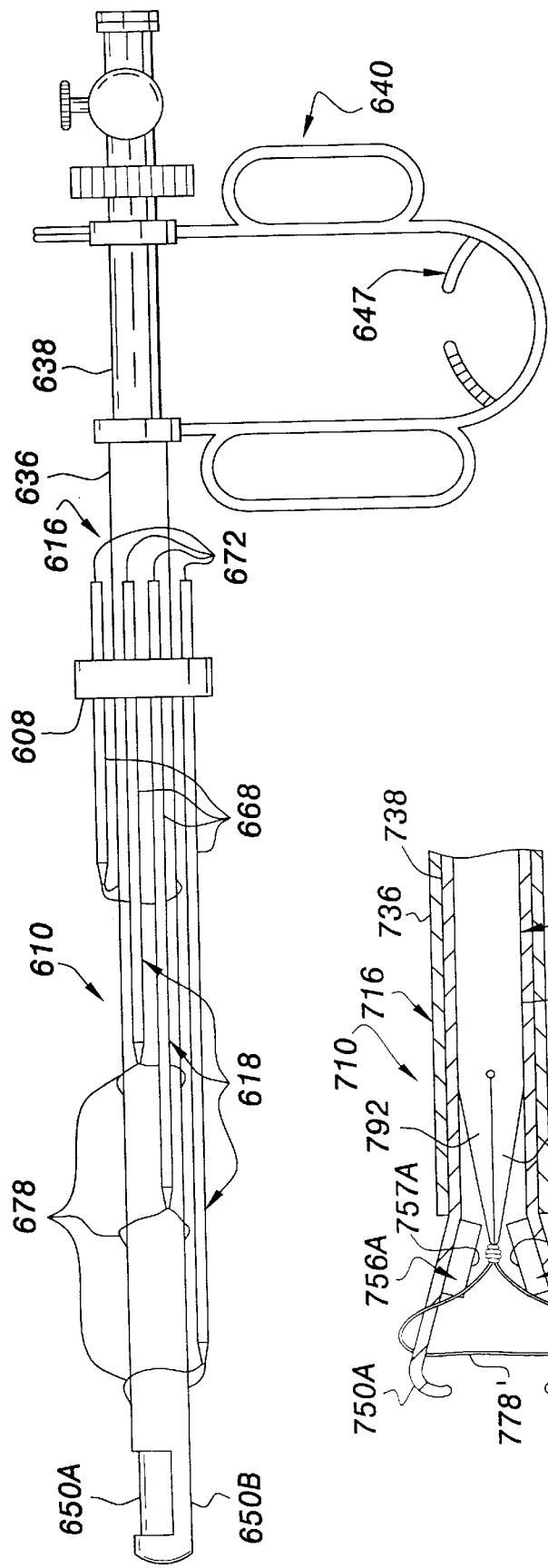
FIG. 35 is a side view of a modification of an endoscopic tubal ligation instrument assembly including a grasping instrument and a ligating instrument.
FIG. 36 is a broken side view, partly in section, of a distal portion of another modification of an endoscopic tubal ligation instrument assembly including a grasping instrument and a ligating instrument.

FIG. 35 illustrates at 610 an endoscopic tubal ligation instrument assembly including grasping instrument 616 and a plurality of ligating instruments 618. Grasping instrument 616 is the same as grasping instrument 116 and includes outer member 636, inner member 638, grasping members 650A and 650B and handle 640 for moving the outer member 636 and/or the inner member 638 longitudinally relative to one another to move the grasping members 650A and 650B between open and closed positions. Outer member 636 carries a flange 608 capable of being moved longitudinally, proximally and distally, along the outer member 636. Flange 608 carries and secures a plurality of ligating instruments 618, the ligating instruments 618 being the same as the Endoloop™ device 18. The tubular members 668 of each ligating instrument 618 are slidably and releasably or removably disposed in holes in flange 608, respectively, with the proximal ends 672 of the ligating instruments disposed proximally of flange 608 allowing the proximal ends 672 to be broken off or separated as discussed for proximal end 72. The tubular members 668 of the ligating instruments 618 are of different lengths, and the ligating instruments 618 are arranged around the outer member 636 in sequence from longest to shortest with the ligature loops 678 of the ligating instruments disposed around the outer member 636. Four ligature loops 678 are disposed around outer member 636 allowing multiple ligatures to be formed without withdrawing the instrument assembly from the anatomical cavity.

During use, the flange 608 can be moved distally along the outer member 636 to advance the longest tubular member 668 to position the ligature loop 678 thereof around anatomical tubular structure held by grasping member 650B. In order to tighten the ligature loop of the longest tubular member around the anatomical tubular structure, the proximal end 672 thereof is broken or separated from the remainder of the tubular member, and the longest tubular member is moved distally to contract the ligature loop around the anatomical tubular structure, to form a ligature, the tubular member sliding through the hole in flange 608. Upon formation of the ligature, the longest tubular member is removed from the flange 608 for withdrawal from the anatomical cavity and the next longest ligating instrument 618 is utilized to form the next ligature. The instrument assembly 610 of FIG. 35 can be introduced through the same port as an endoscope or through a different port than an endoscope.

FIG. 36 illustrates at 710 another instrument assembly comprising a grasping instrument 716, similar to grasping instrument 16, and a ligating instrument 718, which is the same as ligating instrument 118, disposed within the inner member 738 of the grasping instrument 716. Inner member 738 is disposed within outer member 736 and includes grasping members 750A and 750B having cutting members 756A and 756B, respectively, designed as biopsy or tissue collecting boxes. The ligating instrument 718 is disposed in the inner member 738 with the push fingers 792 of the knot pusher 768 in the closed position and the external ligature loop 778' disposed around the grasping members 750A and 750B. The instrument assembly 710 formed by grasping instrument 716 and ligating instrument 718 is provided with a single handle or multiple handles at a proximal end thereof for operating the grasping instrument 716 and the ligating instrument 718. The handle is operable to move the grasping members 750A and 750B from the open position shown in FIG. 36 to a closed position to grasp and draw anatomical tubular structure through the ligature loop 778'. It should be appreciated that the grasping instrument 716 can be moved longitudinally relative to the ligating instrument 718 and/or the ligating instrument 718 can be moved longitudinally relative to the grasping instrument 716 to facilitate the endoscopic tubal ligation procedure. Once the anatomical tubular structure has been drawn through the ligature loop 778', the ligating instrument 718 is operated to contract the ligature loop 778' around the anatomical tubular structure to form a ligature, to cut the connecting segment (not shown) of the ligature loop 778' to sever the ligature from the remainder of the ligature supply and to deploy the next ligature loop externally of the pusher 768. In order to cut the anatomical tubular structure, the grasping members 750A and 750B are positioned to receive the anatomical tubular structure between the cutting edges 757A and 757B of the cutting members and are movable to the closed position to cut the anatomical tubular structure between the cutting edges such that the cut segment of the anatomical tubular structure is captured in the biopsy boxes. When used in endoscopic procedures, the instrument assembly 710 can be introduced through the same port as an endoscope or through a different port than the endoscope.

Another modification of an instrument assembly according to the present invention is illustrated at 810 in FIG. 37, the instrument assembly 810 being particularly useful in endoscopic procedures. Instrument assembly 810 includes an endoscope 814 with a body 830 having an observation window 832 at a distal end thereof and a channel 824 for receiving both a grasping instrument 816 and a ligating instrument 818. Grasping instrument 816 includes an outer member 836 and an inner member 838 disposed within the outer member 836. The inner member 838 is bifurcated to form spaced prongs 853 defining a passage therebetween for receiving the ligating instrument 818. Grasping members 850A and 850B are disposed at distal ends of prongs 853, respectively. Prongs 853 are each made partly or entirely of resilient, flexible or spring materials, or materials having shape memory, to have bendable transverse segments normally disposed in a bent, angled or perpendicular configuration as shown in FIG. 37 and in dotted lines in FIG. 38 such that the grasping members 850A and 850B are laterally offset from a main body of the prongs 853. In the bent configuration for inner member 838, the prongs 853 each bend such that the bendable transverse segments extend angularly, transversely or perpendicularly between the main body of the prong and its associated grasping member. Accordingly, a central longitudinal axis of the main body of a prong is disposed parallel to a central longitudinal axis of its associated grasping member in the bent configuration. The inner member 838 is movable from the bent configuration to a straight or unbent configuration as shown in FIG. 38 wherein the bendable segments and, therefore, the grasping members 850A and 850B, are axially or longitudinally aligned with the main bodies of prongs 853, respectively, to permit introduction of the grasping instrument 816 through the channel 824. Once the bendable segments have passed through the channel 824 and are disposed externally of the distal end of endoscope 814, the inner member 838 automatically returns to the bent configuration. The inner member 838 is rotatable in channel 824 relative to endoscope 814, the inner member 838 being rotatable about the main body central longitudinal axis. The outer member 836 and/or the tubular member 868 of ligating instrument 818 can rotate with the inner member 838, or the outer member 836 and/or the tubular member 868 can be fixed against rotation with inner member 838.

Grasping members 850A and 850B each have an arcuate or partial circular configuration in cross section, and the grasping members carry or form cutting edges or blades 857. Prongs 853 are resiliently or otherwise biased outwardly away from one another such that the grasping members 850A and 850B are normally disposed in an open position. The grasping members 850A and 850B are maintained or constrained in a closed position by outer member 836 with lateral edges of the grasping members in contact with one another to define a closed interior and a semi-spherical nose at a distal end of the grasping members. The grasping members are maintained in the closed position due to engagement of the outer member 836 with bumps 831 on prongs 853 when a handle (not shown) of the grasping instrument 816 is in the rest position. The handle of the grasping instrument 816 can have any suitable configuration and structure to maintain the grasping members in the closed position when the handle is in the rest position, to be operable to move the outer member and/or the inner member longitudinally relative to the other to release the grasping members for movement to the open position and to permit rotation of the inner member 838 relative to endoscope 814. The grasping members can be disposed in the open position when the handle is in the rest position in which case the grasping members are moved to the closed position via operation of the handle. Ligating instrument 818 can be similar to any of the ligating instruments disclosed herein and includes tubular member or knot pusher 868 passing between the prongs 853 and a ligature loop 878 having a knot 880 disposed externally of tubular member 868. The endoscope 814, the grasping instrument 816 and the ligating instrument 818 are independently, longitudinally movable relative to one another.

Preparatory to introduction of instrument assembly 810 at an internal operative site through an endoscopic sized port for an endoscopic tubal ligation procedure, the grasping instrument 816 is in a confined position with inner member 838 arranged as shown in FIG. 37 in a first rotational position with grasping members 850A and 850B disposed within the confines or bounds of the external circumferential, diametric or peripheral cross-sectional dimension of body 830 of endoscope 814 such that the grasping members are circumscribed by the external circumference or cross-sectional periphery of the body 830. The ligating instrument 818 passes between the prongs 853 and through channel 824 such that it also is disposed within or circumscribed by the external circumference or cross-sectional periphery of the body 830 of endoscope 814 with the grasping members 850A and 850B laterally offset from and disposed along side the tubular member 868. Accordingly, the external circumference or cross-sectional periphery of the body 830 of endoscope 814 defines the maximum cross-sectional profile or size of the instrument assembly 810 introduced through the port, thusly minimizing the size of the port through which body 830 can be introduced. As pointed out above, introduction of the grasping instrument 816 through channel 824 is facilitated by unbending or straightening of the inner member 838 when the grasping instrument is manually moved into and through the channel 824. It should be appreciated that the grasping instrument 816 and the ligating instrument 818 can be introduced in channel 824 simultaneously or separately and that the ligature loop 878 can be disposed around the grasping members 850A and 850B.

Once a distal end of the instrument assembly 810 has been introduced at the internal operative site, such as in an anatomical cavity, the inner member 838 is rotated 180° about its central longitudinal axis and relative to the endoscope 814 to a second rotational position. The handle of the grasping instrument can be provided with a mechanism for rotating the inner member independently or together with the outer member and/or the ligating instrument, and the handle itself can be rotated to rotate the grasping instrument relative to the endoscope. The grasping members 850A and 850B will then be in an offset or unconfined position wherein the grasping members 850A and 850B are disposed beyond or outside of the external circumferential, diametric or peripheral cross-sectional dimension of body 830 to be positioned outside of the external circumference or periphery of the body 830. The grasping members 850A and 850B will still be laterally offset from and parallel to tubular member 868 but will be disposed along an opposite side of the tubular member 868. It should be appreciated that the handle of the grasping instrument 816 can be designed to permit rotation of the inner member 838 while the handle remains fixed or stationary, or the handle of the grasping instrument can be designed to rotate with the inner member. The instrument assembly 810 will then be arranged as shown in FIG. 39 and is ready to be utilized to form a ligature.

In order to form a ligature in anatomical tubular structure, such as the Fallopian tube, with instrument assembly 810, the handle of the grasping instrument 816 is operated to move the inner member 838 distally and/or the outer member 836 proximally to release bumps 831 from engagement by outer member 836 such that the prongs 853 move outwardly away from one another to move the grasping members 850A and 850B to the open position as shown in FIG. 40. FIG. 40 illustrates the grasping members 450A and 450B moved distally relative to the endoscope 814. The grasping members in the open position are utilized to grasp the Fallopian tube F and to draw the Fallopian tube F into a loop formation through the ligature loop 878. Grasping surfaces of the grasping members 850A and 850B can be provided with serrations, bosses, irregularities or roughness to facilitate grasping as shown at 807 in FIG. 40. The ligating instrument 818 can be moved distally and/or proximally and/or the grasping instrument 816 can be moved distally and/or proximally relative to the endoscope 814 to facilitate positioning of the ligature loop 878 around the loop formation of the Fallopian tube F. FIG. 40 illustrates the ligating instrument moved distally relative to endoscope 814 and grasping instrument 816. The tubular member 868 is moved distally and/or the length of ligature material is moved proximally to contract the ligature loop 878 around the loop formation of the Fallopian tube F to form a ligature. The bend or knuckle of the Fallopian tube F is cut utilizing the cutting blades 857 of the grasping instrument 816, and the ligature material is cut proximally of the ligature with the cutting blades 857 or with a separate cutting instrument. The procedure is visualized externally of the abdominal cavity via the endoscope 814, and such visualization is enhanced due to the offset position of the grasping members. The grasping members are rotated or moved from the offset position to the confined position when it is desired to withdraw the grasping instrument from the abdominal cavity and/or from the endoscope 814.

FIG. 41 illustrates at 910 another modification of an endoscopic tubal ligation instrument assembly for use in the methods according to the present invention. Instrument assembly 910 is similar to instrument assembly 810 except that the prongs 953 of grasping instrument 916 of instrument assembly 910 are formed by halves, respectively, of a longitudinally split inner tubular member 938. Prongs 953 each have a bent, angled, offset, transverse or perpendicular segment extending perpendicularly or angularly to the main body of the prong and a grasping member extending distally from the transverse segment parallel to the main body. Lateral edges of prongs 953 contact one another in the closed position, the main bodies of the prongs cooperating to define an enclosed interior passage for receiving ligating instrument 918. Each prong 953 has a semi or partial circular opening at the junction of the transverse segment with the main body, the openings cooperating to define an aperture 905 in the closed position axially aligned with the interior passage and through which the ligating instrument 918 may pass. Grasping members 950A and 950B of grasping instrument 916 are carried by the transverse segments of prongs 953, respectively, and are similar to grasping members 850A and 850B. Grasping members 950A and 950B are biased to an open position and are maintained in the closed position by engagement of outer member 936 with bumps 931 on prongs 953. In order to permit introduction of grasping instrument 916 through channel 924, the transverse segments of prongs 953 can be made capable of unbending or straightening as described for grasping instrument 816. Alternatively, the prongs 953 can be formed with a rigid or permanent bend or angle in which case the grasping instrument 916 is pre-assembled with endoscope 914 by introducing a rear or proximal end of the inner member 938 through a distal end of channel 924. Where the inner member 938 is introduced from the distal end of channel 924, the handle of the grasping instrument 916 is designed for removable or releasable engagement and re-engagement with the inner member 938. The outer member 936 can be introduced in endoscope 914 from a proximal end of channel 924; however, by designing the outer member 936 to be selectively engageable and disengageable with the handle, the outer member 936 can also be introduced from the distal end of the channel 924. Ligating instrument 918 is similar to ligating instrument 818 and includes a ligature loop 978 having a knot 980 disposed externally of tubular member or knot pusher 968. The endoscope 914 has an operating channel 924 for receiving the grasping instrument 916 and the ligating instrument 918 and can have one or more additional operating channels 924 as shown in dotted lines in FIG. 42.

During introduction of the instrument assembly 910 through a small-size port in endoscopic procedures, the grasping members 950A and 950B are in the confined position with inner member 938 arranged as shown in FIG. 41 with the grasping members 950A and 950B disposed within the confines of the external circumference or cross-sectional periphery of body 930 of endoscope 914. Upon introduction of a distal end of the instrument assembly 910 at an internal operative site, the inner member 938 is rotated 180° about its longitudinal axis and relative to the endoscope 914 to move the grasping members 950A and 950B to the offset or unconfined position to position the grasping members 950A and 950B outside the confines of the external circumference or cross-sectional periphery of the body 930 of endoscope 914 and along an opposite side of tubular member 968 as shown in FIG. 42. Grasping instrument 916 is operated in a manner similar to grasping instrument 816 in that one or both of the outer and inner members 936 and 938, respectively, are moved longitudinally relative to the other to release the bumps 931 from engagement by outer member 936 causing movement of the grasping members 950A and 950B to the open position.

An additional embodiment of an endoscopic tubal ligation instrument assembly for use in the methods according to the present invention is illustrated in FIG. 43 at 1010. The instrument assembly 1010 is similar to instrument assembly 910 except that the opening and closing movements for grasping members 1050A and 1050B of grasping instrument 1016 of instrument assembly 1010 occur in a plane perpendicular to the plane of the opening and closing movements of grasping members 950A and 950B. The opening and closing movements for grasping members 1050A and 1050B occur in an up and down or vertical direction whereas the opening and closing movements for grasping members 950A and 950B occur in a side to side or lateral direction with respect to a handle of the grasping instrument. As shown in FIG. 43, which illustrates the grasping members 1050A and 1050B in the off-set or unconfined position, prongs 1053 of the inner member 1038 are constrained via engagement of outer member 1036 with bumps 1031 to maintain grasping members 1050A and 1050B in the closed position. The ligating instrument 1018 of instrument assembly 1010 passes through an aperture 1005 of prongs 1053 to position ligature loop 1078 externally of endoscope 1014. The aperture 1005 is preferably oval or oblong in configuration to permit the grasping member 1050A to move upwardly in the direction of tubular member 1068 of ligating instrument 1018 when the grasping members are released for movement to the open position as shown in FIG. 44A. As shown in FIG. 44A, grasping member 1050A moves upwardly while grasping member 1050B moves downwardly. However, both grasping members do not have to move when the grasping members are released to the open position, it being noted that one of the grasping members can be movable while the other grasping member remains fixed. As shown in FIG. 44A, planar grasping surfaces of grasping members 1050A and 1050B are provided with serrations 1007 to facilitate grasping of anatomical tissue as well as for grasping a needle between the grasping surfaces when the grasping members 1050A and 1050B are moved to the closed position thusly serving as a needle holder.

As shown in FIG. 44A, a curved suture needle N carrying a length of filamentous suture material M can be grasped and held between grasping members 1050A and 1050B. The grasping instrument 1016 can be used to drive the needle N; for example, rotation of inner member 1038 counterclockwise from the unconfined position shown in FIG. 45 toward the confined position can cause needle N to penetrate anatomical tissue including anatomical tubular structure such as the Fallopian tube for suturing with material M. It should be appreciated that where the grasping instrument is used with a suture needle, a ligating instrument need not be provided where the functions to be performed with the ligating instrument can be accomplished with the needle and suture material.

FIG. 44B illustrates the instrument assembly 1010 with grooves G provided in the planar grasping surfaces of grasping members 1050A and 1050B, respectively, only the groove G of the grasping member 1050B being visible in FIG. 44B. The grooves G are in alignment with one another in the closed position for the grasping members to form a cavity or channel for receiving a suture needle, such as a straight or curved suture needle. The grasping instrument 1016 can be manipulated, such as by rotation and/or longitudinal movement of the grasping members 1050A and 1050B relative to endoscope 1014, to drive the needle held in grooves G.

An additional modification of an instrument assembly for use in the methods according to the present invention is illustrated at 1110 in FIG. 45. The instrument assembly 1110 includes a grasping instrument 1116 and a ligating instrument 1118 disposed within a passage of the grasping instrument 1116. Grasping instrument 1116 includes an outer member 1136, an inner member 1138 disposed in outer member 1136, grasping members 1150A and 1150B carried by inner member 1138 and a handle 1140 releasably engageable and re-engageable with proximal ends of outer member 1136 and inner member 1138. Outer member 1136 has a rigid bent, angled, transverse or perpendicular segment disposed transversely, perpendicularly or angularly to a main body of the outer member and an offset distal segment 1137 extending distally from the transverse segment to be disposed parallel to the main body of the outer member 1136. A lumen or passage extends entirely through the outer member 1136 including the transverse segment and the offset distal segment 1137.

Inner member 1138 is best shown in FIGS. 46 and 47 and includes a main body disposed in the main body of outer member 1136, a bent, perpendicular, transverse or angled segment disposed in the transverse segment of outer member 1136 and a Y-shaped operating segment 1155 disposed in the offset distal segment 1137 of outer member 1136. A lumen or passage extends entirely through the main body of inner member 1138 in axial or longitudinal alignment with an aperture 1105 in the transverse segment of the outer member 1136 such that the tubular member 1168 of the ligating instrument 1118 passes through the passage of the inner member 1138 and the aperture 1105 to position ligature loop 1178 externally of the outer member 1136 of the grasping instrument as shown in FIGS. 45–47. The Y-shaped operating segment 1155 has outwardly extending arms or branches 1127 pivotally connected to legs 1129A and 1129B extending from grasping members 1150A and 1150B, respectively. As illustrated in FIGS. 46 and 47, the legs 1129A and 1129B are angled inwardly from their respective grasping members to overlap one another in cross-wise fashion. Proximal ends of legs 1129A and 1129B are pivotally connected to arms 1127, respectively, at pivots, joints or hinges, such as pivot pins 1111. The legs 1129A and 1129B are pivotally connected to one another, where they overlap, by a pivot, joint or hinge such as pivot pin 1113. The pivot pin 1113 has opposing ends fixedly secured to the outer member 1136. The inner member 1138 is slidably disposed in the outer member 1136 for longitudinal movement relative thereto, and the pivot pins 1111 move with the inner member. As shown in FIG. 46, there is a gap or space between the transverse segment of the inner member 1138 and an inner surface of the transverse segment of the outer member 1136 to permit the inner member 1138 to be moved longitudinally, distally relative to the outer member.

As shown in FIG. 45, handle 1140 includes pivotally connected legs 1164A and 1164B. Proximal leg 1164B is connected with a cylindrical, hollow extension 1163 of handle 1140 having a forward end upon which a fitting or knob 1161 is rotatably mounted. A tubular member 1167 extends entirely through the extension 1163 and terminates distally within an internal passage of knob 1161. Tubular member 1167 extends proximally of extension 1163 and is provided with a valve 1143 disposed proximally of handle 1140. Distal leg 1164A is pivotally connected to extension 1163 at pivot pin 1159, an upper end of leg 1164A extending through a slot or opening in extension 1163 to be fixedly connected to tubular member 1167. The legs 1164A and 1164B are provided with finger rings 1165, respectively, to facilitate grasping and operation of handle 1140. The handle 1140 is provided with a locking mechanism 1147 including locking arms 1149 extending from legs 1164A and 1164B, respectively, and carrying cooperating locking structure 1151 for locking the handle 1140 in a compressed or squeezed position. The handle 1140 is normally disposed in a rest position as shown in FIG. 45, and the handle 1140 can include various springs or other bias members, such as a torsion spring at pivot 1159, for biasing the handle 1140 to the rest position. The handle 1140 is movable to a compressed or squeezed position via manual compressive or squeezing operation of legs 1164A and 1164B causing the tubular member 1167, which is slidably disposed in the extension 1163, to be moved longitudinally, distally relative to the extension 1163. The handle 1140 can include an electrical connector 1145 for supplying electrical current to tubular member 1167 and the inner member 1138.

The outer and inner members 1136 and 1138 are releasably connected to handle 1140 via external threads 1109 on a proximal end of outer member 1136 releasably engaging internal threads at a distal end of knob 1161 and via external threads 1109' on a proximal end of inner member 1138 releasably engaging internal threads on a distal end of tubular member 1167, the knob 1161 forming a mechanism for rotating the outer and inner members. Since the outer and inner members 1136 and 1138 are disengageable from handle 1140, the bent or angled segment of outer member 1136 can be rigid. The outer and inner members 1136 and 1138 can be inserted in a channel of an endoscope through a distal end of the channel; and, after being inserted through the channel from a distal end thereof, the proximal ends of the outer and inner members can be secured to the handle 1140. The threads on the outer and inner members can be designed such that threading of the outer member onto knob 1161 simultaneously causes the threads of the inner member 1138 to engage the threads of tubular member 1167. With the outer and inner members secured to handle 1140, the outer and inner members can be rotated about a longitudinal axis of the outer member main body via manual rotation of knob 1161, the inner member 1138 rotating with the outer member 1136 due to the connection provided by pin 1113. The tubular member 1167 can remain stationary when the inner member 1138 is rotated or the tubular member 1167 can rotate with the inner member. For example, the tubular member 1167 can be provided with a flange rotatably disposed in a recess of leg 1164A to form a universal joint U allowing the tubular member 1167 to rotate. It should be appreciated that the outer and inner members can be releasably coupled to handle 1140 in many various ways while allowing the inner member and/or the grasping members to rotate and that various universal joints can be used to releasably secure the outer and inner members to the handle and to permit rotation of the outer and inner members relative to the handle.

As shown in FIG. 45, the tubular member 1168 of the ligating instrument 1118 passes through the valve 1143, the tubular member 1167, the main body of inner member 1138 and the aperture 1105 in outer member 1136 such that ligature loop 1178 is disposed externally of the outer member 1136 and the proximal end 1172 of the ligating instrument is disposed proximally of valve 1143. Valve 1143 includes a rotatable knob allowing the valve 1143 to be manually opened and closed, the valve 1143 in the closed position engaging the tubular member 1168 extending therethrough and thusly fixedly securing the tubular member 1168 in the tubular member 1167 of handle 1140. Accordingly, when the proximal end 1172 is broken at breakpoint 1181, the proximal end 1172 can be pulled proximally to draw the ligature material through the tubular member 1168 to contract the ligature loop 1178 while the tubular member 1168 is fixedly held by valve 1143.

In an endoscopic tubal ligation procedure, the grasping instrument 1116 is disposed in an endoscope or barrel and is introduced at an internal operative site through a small size port with the grasping members 1150A and 1150B in the confined position relative to the endoscope or barrel. Once the grasping members are disposed at the internal operative site, the knob 1161 is rotated to move the outer and inner members 1136 and 1138 from the first rotational position to the second rotational position to move the grasping members from the confined position to the unconfined or offset position. The grasping members 1150A and 1150B are moved from the closed position to the open position shown in FIG. 47 via squeezing operation of handle 1140 causing the tubular member 1167 to move distally causing corresponding longitudinal distal movement of inner member 1138 relative to outer member 1136. Movement of the inner member 1138 longitudinally, distally relative to the outer member 1136 causes the legs 1129A and 1129B to be pivoted by operating segment 1155 about pivot pin 1113 causing pivotal movement of the grasping members 1150A and 1150B to the open position as shown in FIG. 47.

Figure 48:
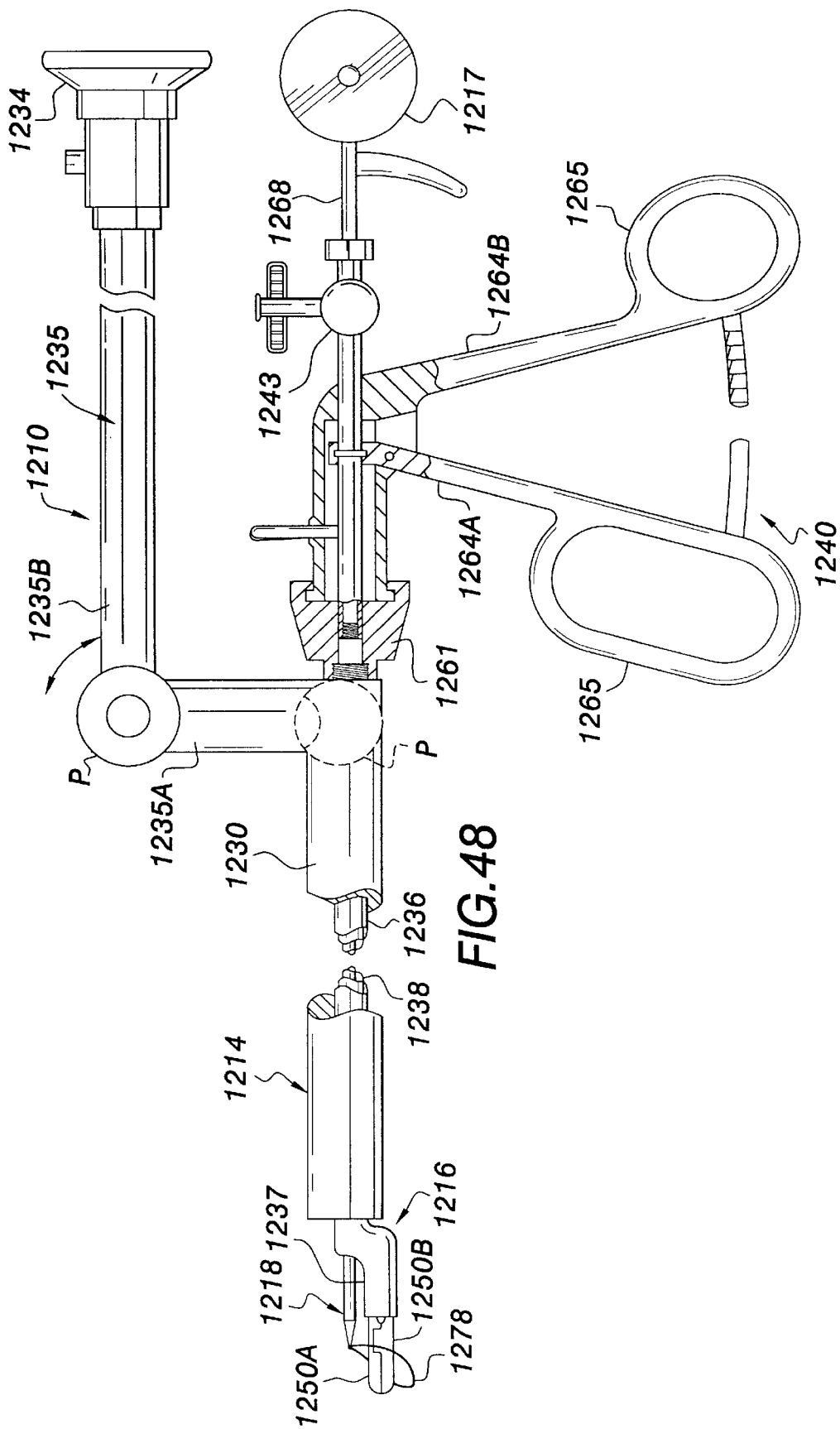
FIG. 48 is a broken side view, partly in section, of an additional modification of an endoscopic tubal ligation instrument assembly.

Another modification of an instrument assembly for use in the methods according to the present invention is illustrated in FIG. 48 at 1210. The instrument assembly 1210 is similar to instrument assembly 1110 except that the instrument assembly 1210 is shown with an endoscope 1214 having a channel receiving the grasping instrument 1216 and the ligating instrument 1218 and except that the ligating instrument 1218, which is similar to the Endoloop™ ligating device 18, includes a spool or wheel 1217 for winding the ligature material of the ligating instrument thereon to contract the ligature loop 1278 while the tubular member 1268 is secured by valve 1243. When the proximal end of the ligating instrument is separated from the remainder of the tubular member 1268 at the break point, the ligature material can be wound around or connected to the spool 1217. The spool 1217 can be manually rotated by a finger of the hand grasping the handle 1240 to contract the ligature loop 1278. It should be appreciated that the ligating instrument 1218 can be designed without a separable proximal end since the ligature material need only pass proximally through the tubular member 1268 for connection with spool 1217.

The grasping instrument 1216 is similar to grasping instrument 1116, the grasping members 1250A and 1250B of the grasping instrument being shown in the offset or unconfined position in FIG. 48. In order to move the grasping members 1250A and 1250B to the confined position, the knob 1261 is rotated to rotate the outer member 1236 and the inner member 1238, which is connected to the outer member 1236 via the pivot pin connecting the overlapping legs of the grasping members 1250A and 1250B. The outer and inner members 1236 and 1238 are rotated 180° from the position shown in FIG. 48 such that the offset distal segment 1237 and the grasping members 1250A and 1250B will be disposed within the confines of the external circumference or cross-sectional periphery of body 1230 of endoscope 1214. The grasping members 1250A and 1250B are moved between the open and closed positions in the same manner as described for grasping members 1150A and 1150B in that handle 1240 is compressed or squeezed via squeezing operation with finger rings 1265. The grasping instrument 1216 is slidably disposed in the channel of endoscope 1214 and, therefore, is movable longitudinally relative to endoscope 1214 in both the distal and proximal directions to facilitate use.

Endoscope 1214 is similar to endoscope 114 and has a connecting segment or arm 1235 connecting eyepiece 1234 to the endoscope body 1230 with the arm 1235 having an arm segment 1235A extending perpendicularly or angularly from body 1230 and an arm segment 1235B extending proximally from arm segment 1235A parallel with the body 1230. The lengths of arm segments 1235A and 1235B are preferably selected to insure that the eyepiece 1234 is spaced sufficiently from the handle 1240, the valve 1243, the tubular member 1268 and the wheel 1217 to avoid contamination. Endoscope 1214 is different than endoscope 114 in that endoscope 1214 has a joint, hinge or pivot P pivotally or rotatably connecting the arm segment 1235B to the arm segment 1235A. The arm segment 1235B is rotatable or pivotal around pivot P in the direction of the arrow shown in FIG. 48 to adjust the angular position of arm segment 1235B and, therefore, eyepiece 1234. The joint P can include a push button or another type of activator for releasing arm segment 1235B for angular movement and for locking the arm segment 1235B in a desired position. FIG. 48 illustrates in dotted lines an alternative location for joint P between arm segment 1235A and body 1230. The arm segment 1235B can include a connector for connection of endoscope 1214 to a TV monitor. Endoscope 1214 is representative of an endoscope that is both offset and angularly adjustable.

Figure 49:
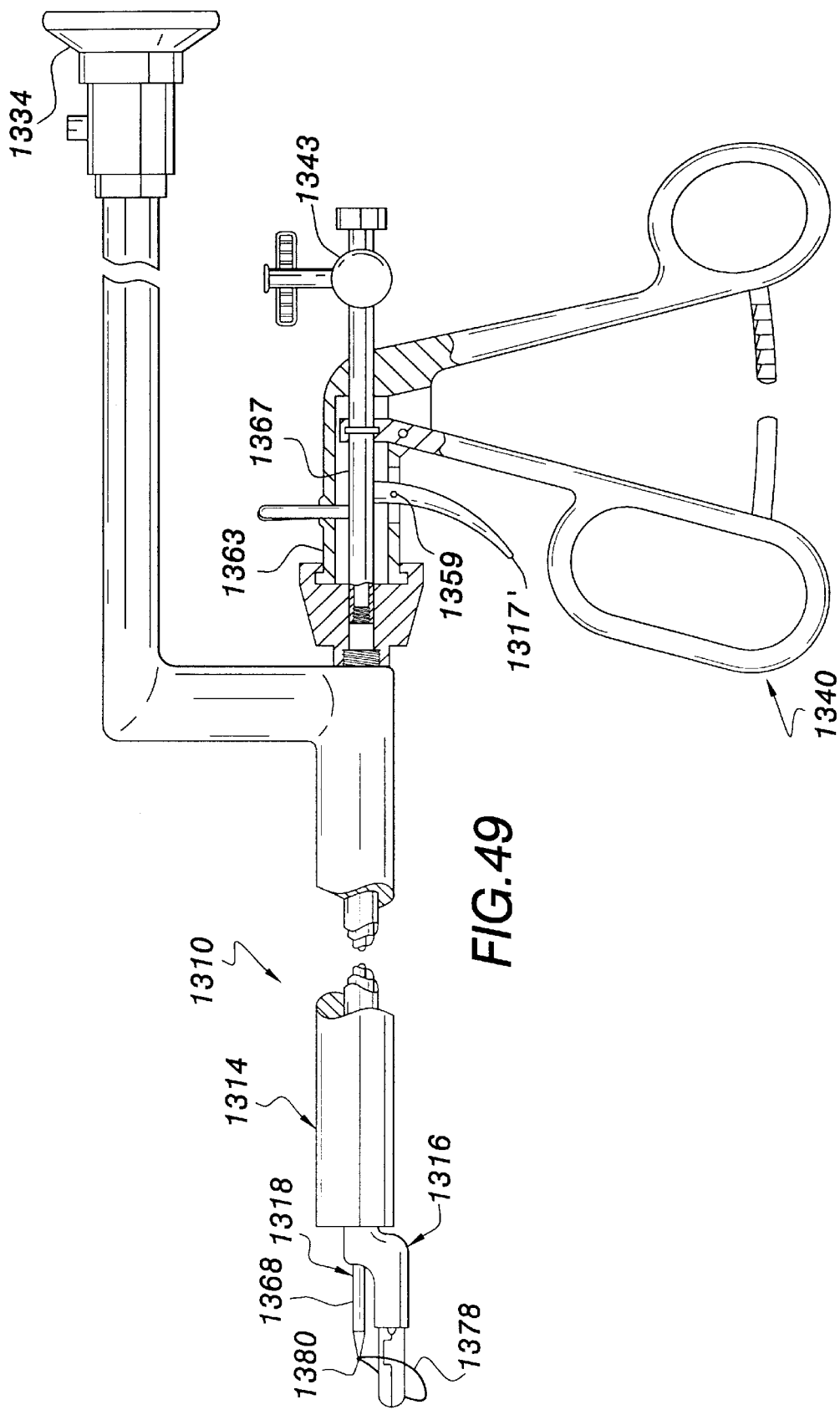
FIG. 49 is a broken side view, partly in section, of a further modification of an endoscopic tubal ligation instrument assembly.

Another modification of an instrument assembly for use in the methods of the present invention is illustrated at 1310 in FIG. 49. The instrument assembly 1310 is substantially the same as the instrument assembly 1210 except that the ligating instrument 1318 for instrument assembly 1310 includes a manually operable lever 1317' connected with the tubular member 1368 of the ligating instrument 1318 for moving the tubular member 1368 distally to contract the ligature loop 1378. The endoscope 1314 and the grasping instrument 1316 for endoscopic tubal ligation instrument assembly 1310 are substantially the same as the endoscope 1214 and the grasping instrument 1216 except that the tubular member 1367 of handle 1340 has a slot therein through which the lever 1317' passes. The lever 1317' is pivotally mounted to the cylindrical extension 1363 of handle 1340 by a pivot, joint or hinge such as pivot pin 1359', and the lever 1317' passes through an opening in the cylindrical extension 1363. The lever 1317' is connected to the tubular member 1368 of ligating instrument 1318, and the proximal end of the tubular member 1368 is broken away from the remainder thereof and is fixedly secured by valve 1343. With the broken off proximal end secured by valve 1343, pivotal operation of lever 1317', as permitted by the slot in the tubular member 1367, causes the remainder of tubular member 1368 to be moved longitudinally, distally to push knot 1380 distally to contract ligature loop 1378. The lever 1317' can be spaced from handle 1340 and eyepiece 1334 a distance sufficient to avoid contamination.

FIG. 50 illustrates at 1418 a modification of a ligating instrument for use in the methods of the present invention. Ligating instrument 1418 is in the nature of a multiple loop Endoloop™-type ligating device including a tubular member 1468 having a tapered distal end 1470 and a plurality of lengths of ligature material 1476 disposed in tubular member 1468, each length of ligature material 1476 terminating distally in a ligature loop 1478 and terminating proximally at an end secured to a frangible or separable proximal segment 1472 of the tubular member 1468. In the case of ligating instrument 1418, four lengths of ligature material 1476A, 1476B, 1476C and 1476D are disposed in tubular member 1468, and each length of ligature material is connected to a frangible proximal segment 1472A, 1472B, 1472C and 1472D, respectively. The proximal segments 1472 are connected to one another in series at break points 1481 such that the proximal segment 1472A is the first one to be broken off from the remainder of tubular member 1468 at its break point 1481. Once the proximal segment 1472A has been broken away from the remainder of tubular member 1468, the proximal segment 1472A can be pulled proximally and/or the remainder of tubular member 1468 can be moved distally to contract the ligature loop 1478A that is connected to the proximal segment 1472A. The next proximal segment 1478B is then separated from the remainder of the tubular member 1468 to contract the ligature loop 1478B to which it is connected and so on until a desired number of the ligature loops 1478 have been utilized during a procedure. The lengths of ligature material 1476 pass through holes or apertures in the distal end 1470 of tubular member 1468, and the knots of the ligature loops 1478 are sufficiently large to prevent passage of the ligature loops through the holes.

A distal portion of a modification of a grasping instrument for use in the methods according to the present invention is illustrated in FIG. 51 at 1516. Grasping instrument 1516 includes outer tubular member 1536 receiving inner tubular member 1538 which carries or is formed with grasping members 1550A and 1550B. Inner tubular member 1538 is bifurcated, split or slit at a distal end thereof to resiliently bias the grasping members 1550A and 1550B to the open position. The grasping members have distal ends or tips comprising inwardly curved or angled tip segments 1554A and 1554B, respectively, and longitudinally extending tip segments 1554A' and 1554B' extending distally from tip segments 1554A and 1554B, respectively. Inner surfaces of the tip segments 1554A' and 1554B' contact one another when the grasping members are in the closed position, the grasping members 1550A and 1550B being representative of grasping members having "kissing" tips. Grasping members 1550A and 1550B have tissue collection boxes 1556A and 1556B, respectively, the tissue collection box 1556B fitting or nesting within the tissue collection box 1556A when the grasping members are moved to the closed position. The tissue collection boxes have rounded outer surfaces forming bumps or protrusions 1531A and 1531B on the grasping members 1550A and 1550B, respectively.

The grasping members 1550A and 1550B are resiliently biased to the open position shown in FIG. 51 and are in the open position when a handle (not shown) of the grasping instrument 1516 is in the rest position. Accordingly, the grasping members 1550A and 1550B are normally in the open position and are moved to the closed position via manual operation of the handle. For example, the handle of the grasping instrument 1516 can be designed to move the outer member 1536 distally and/or the inner member 1538 proximally causing the distal end of the outer member 1536 to engage the bumps 1531A and 1531B causing movement of the grasping members 1550A and 1550B to the closed position.

A distal portion of another modification of a grasping instrument for use in the methods according to the present invention is illustrated in FIG. 52 at 1616. Grasping instrument 1616 is similar to grasping instrument 1516 except that the grasping members 1650A and 1650B of grasping instrument 1616 have inwardly angled distal tips 1654A and 1654B, respectively, that overlap one another when the grasping members are in the closed position. Accordingly, the grasping member 1650A is slightly longer than the grasping member 1650B such that the tip 1654A overlaps the tip 1654B in the closed position. The tissue collection boxes 1656A and 1656B of grasping members 1650A and 1650B, respectively, are similar to tissue collection boxes 1556A and 1556B except that the tissue collection box 1656A is designed to fit or nest within the tissue collection box 1656B when the grasping members are in the closed position. The tissue collection boxes 1656A and 1656B have protruding outer surfaces defining bumps 1631A and 1631B, respectively, for being engaged by the outer member 1636 when the outer member and/or the inner member 1638 are moved longitudinally relative to one another to move the grasping members 1650A and 1650B from the open position to the closed position.

Another modification of a grasping instrument for use in the methods according to the present invention is illustrated at 1716 in FIG. 53. The grasping instrument 1716 is similar to the grasping instrument 916 except that the prongs 1753 of grasping instrument 1716 each have a curved segment extending from the main body of the prong. The curved segments are curved in the distal direction, and the grasping members 1750A and 1750B extend distally from the curved segments, respectively. Grasping members 1750A and 1750B each have a recess therein between tips 1754A and 1754B and tissue collection boxes 1756A and 1756B defining a grasping space 1760. Each prong 1753 has a semi or partial circular or partial oval or elliptical opening at the junction of the curved segment with the main body of the prong, the openings cooperating to define an aperture 1705 in the closed position axially aligned with the interior passage of the inner member 1738 and through which a ligating instrument may pass. The outer member 1736 has a distal part 1736A removably, releasably or detachably secured to a proximal part 1736B which in turn is secured to the distal leg 1764A of handle 1740. The inner member 1738 has a distal part 1738A releasably, removably or detachably secured to a proximal part 1738B which in turn is connected to the proximal leg 1764B of handle 1740, the proximal leg 1764B passing through a longitudinal slot 1748 in the outer member proximal part 1736B. The distal parts of the outer and inner members are releasably or disengageably attached to the proximal parts thereof at knobs or fittings 1761 and 1761'. The distal parts of the outer and inner members can be connected to the corresponding proximal parts in many various ways such as threaded connections, for example. Handle 1740 includes a locking mechanism 1747 in the nature of a ratchet lock mechanism centrally disposed along base 1766 for locking the handle 1740 in a compressed position.

The prongs 1753 are resiliently biased away from one another to position the grasping members 1750A and 1750B in the open position; however, the grasping members 1750A and 1750B are disposed in the closed position when the handle 1740 is in the rest position due to constraint of prongs 1753 by outer member 1736. The prongs 1753 can be provided with bumps or protrusions for being engaged by the outer member 1736 to facilitate constraint of prongs 1753 to close the grasping members. When the handle 1740 is manually squeezed or compressed, the outer member 1736 is moved proximally and/or the inner member 1738 is moved distally, as permitted by slot 1748, to release the prongs 1753 from constraint by the outer member 1736 causing the grasping members 1750A and 1750B to move to the open position.

FIG. 54 illustrates the grasping instrument 1716 arranged within an operating channel of an endoscope 1714. The distal parts of the outer and inner members 1736 and 1738 can be inserted in the operating channel of the endoscope via a distal or front end of the operating channel and, after being introduced through the operating channel from the distal end thereof, the distal parts of the outer and inner members can be secured to the proximal parts thereof. FIG. 54 shows the grasping members in the confined position disposed within the external circumferential, diametric or cross-sectional peripheral dimension of the endoscope 1714. In order to move the grasping members 1750A and 1750B to the unconfined or offset position, the inner member 1738 is rotated 180° about its central longitudinal axis to position the grasping members outside of or beyond the external circumferential, diametric or cross-sectional peripheral dimension of the endoscope 1714.

FIG. 55 illustrates a modified grasping instrument 1816 disposed in the operating channel of an endoscope 1814 with the grasping members 1850A and 1850B of grasping instrument 1816 disposed in the confined position. Grasping members 1850A and 1850B are similar to grasping members 1750A and 1750B except that the grasping members 1850A and 1850B are curved to correspond substantially with the curvature of the circumferential outer surface of endoscope 1814. In addition, the grasping members 1850A and 1850B open in a lateral direction or motion whereas the grasping members 1750A and 1750B open in an up and down direction or motion. The grasping members 1850A and 1850B have openings therein cooperating in the closed position to form or define an aperture 1805 for receiving a ligating instrument therethrough. The grasping members 1850A and 1850B are moved to the unconfined or offset position in the same manner as that described for grasping members 1750A and 1750B in that the prongs 1853 are rotated to position the grasping members 1850A and 1850B outside of or beyond the circumferential or diametric dimension of endoscope 1814.

It should be appreciated that, although the confined position for the grasping members has been primarily described herein in relation to an endoscope, the grasping members can be confined and unconfined with respect to a barrel or platform through which the grasping instruments are introduced. Accordingly, when the grasping instruments are introduced through a barrel or platform, the grasping members will be disposed within the external circumferential, diametric or peripheral cross-sectional dimension of the barrel; and, in the unconfined position, the grasping members will be disposed beyond or outside of the external circumferential, diametric or peripheral cross-sectional dimension of the barrel. It should also be appreciated that the grasping members can be rotated various amounts between the confined and unconfined position and that the grasping members do not have to be rotated 1800 between the confined position and the unconfined position. The amount of rotation imparted to the grasping members to move the grasping members from the confined position to the unconfined position will depend upon the position desired for the grasping members beyond or outside of the external circumferential, diametric or peripheral cross-sectional dimension of the barrel or endoscope. It should also be appreciated that where the grasping instrument is provided with offset grasping members, both grasping members do not have to be movable in that one of the grasping members can be fixed while the other grasping member is movable.

The grasping instruments can include various offset grasping members, and the offset grasping members can be pivotal, longitudinally movable or rotatable between the open and closed positions.

Various grasping members, instruments or graspers suitable for use in the methods according to the present invention are disclosed in concurrently filed patent applications entitled Surgical Instrument with Rotatably Mounted Offset End Effector and Method of Using the Same, Surgical Instrument with Multiple Rotatably Mounted Offset End Effectors and Method of Using the Same, Suturing Instrument with Rotatably Mounted Offset Needle Holder and Method of Using the Same, and Suturing Instrument with Multiple Rotatably Mounted Offset Needle Holders and Method of Using the Same, the disclosures of all of the latter applications being incorporated herein by reference.

Another modification of a grasping instrument for use in the methods according to the present invention is illustrated in FIG. 56 at 1916. Grasping instrument 1916 is similar to grasping instrument 1116 except that the inner member 1938 of grasping instrument 1916 is in the nature of an actuating wire, cable or rod connected to grasping members 1950A and 1950B. The actuating wire 1938 has a plurality of branches 1927 extending through the bent segment of outer member 1936 and into the offset distal segment 1937 of outer member 1936. The branches 1927 terminate distally at ends connected to a tubular neck carrying grasping members 1950A and 1950B, the neck being slidably disposed in the offset distal segment 1937 of outer member 1936. The grasping members 1950A and 1950B carry biopsy boxes 1956A and 1956B, respectively, forming protrusions 1931A and 1931B, respectively, disposed distally of the offset distal segment 1937. The actuating wire 1938 is disposed in the lumen of the main body of the outer member 1936 adjacent the wall thereof such that the actuating wire 1938 is disposed to one side of the lumen. An aperture 1905 in the angled segment of the outer member 1936 is aligned with the lumen of the main body to form a passage for receiving a ligating instrument. The grasping members 1950A and 1950B are disposed in the open position when a handle (not shown) of the grasping instrument 1916 is in a rest position. In order to operate the grasping members 1950A and 1950B, the actuating wire 1938 is moved proximally and/or the outer member 1936 is moved distally via the handle causing the bumps 1931A and 1931B to be engaged by the distal end of the distal offset segment 1937 thusly moving the grasping members from the open position to the closed position. Movement of the actuating wire 1938 and the branches 1927 distally from the closed position and/or movement of the outer member 1936 proximally from the closed position causes the grasping members to be returned to the open position.

The endoscopes can be movably or slidably disposed in the barrels to permit optimal positioning during the procedure; however, the endoscopes can be non-separable from the barrels and can be formed as non-removable and/or non-movable parts of the barrels, such as being formed integrally, unitarily with the barrels. The endoscope itself can be designed to define one or more channels for receiving the grasping instrument and/or the ligating instrument as well as other instruments. The endoscopes can be rigid or flexible or bendable, and the endoscopes can be partly rigid and partly flexible or bendable. The endoscopes can be designed or provided with various accessories or adjustment features including focus, zoom and magnification adjustments or features and a CCD (charge coupled device). The endoscopes can be branched or bifurcated. The endoscopes can be designed in many various ways and can include fiber optic rod lens systems, various multiple lens systems or digital endoscope systems.

The grasping instruments can be designed in many various ways with one or more diverse grasping members. The grasping instruments can include a single grasping member or multiple grasping members. The grasping members can be pivotal, rotatable or longitudinally movable for movement between open and closed positions; and, where multiple grasping members are provided, some of the grasping members can be fixed or immovable. The grasping members can be designed to be disposed in the open position when the grasping instrument or handle therefor is in the rest position, or the grasping members can be designed to be disposed in the closed position when the grasping instrument or handle therefor is in the rest position. For example, the grasping members can be biased to the open position and be unconstrained to remain in the open position in the rest position, or the grasping members can be constrained in the rest position to be disposed in the closed position. The grasping members do not have to be biased to the open position. For example, the grasping members can be mechanically moved to the open and closed positions, and the grasping members can be biased to the closed position. The inner and outer members of the grasping instrument can both move relative to one another to move the grasping members between the open and closed positions, or one of the inner and outer members can move relative to the other of the inner and outer members to move the grasping members between the open and closed positions. The grasping members can be movable from a confined position to an unconfined or offset position relative to a port, passage or structure through which the grasping members are introduced at an internal operative site as accomplished via rotation of the outer member, the inner member, both the outer and inner members, the grasping members or the entire grasping instrument, for example. The grasping surfaces of the grasping members can be provided with serrations or teeth or other structure to facilitate gripping the anatomical tissue and for other functions such as holding a needle. The grasping instrument can function as a clip applier as well as a needle holder. The grasping instrument can include various handle structure including pivotable members, a pistol grip and triggered members of spring or flexible materials as well as rigid materials. The inner member of the grasping instrument can have various structural configurations including tubes, plates and wires, for example. The grasping instrument can be made integrally, unitarily with the ligating instrument, and a single handle can be provided to operate the grasping instrument and the ligating instrument.

The cutting members can be designed in many various ways to cut anatomical tissue and to include structure for enclosing or capturing the cut segment of anatomical tissue. The cutting members can be used to cut or sever the ligature material and/or the anatomical tissue. However, cutting members for cutting the ligature material and/or the anatomical tissue as well as for capturing the anatomical tissue can be provided as one or more separate cutting instruments. The ligating instrument can be designed with cutting blades to function as the cutting member for cutting the ligature material and/or the anatomical tissue as well as for collecting or capturing the cut tissue for removal from the patient's body.

The ligating instrument, ligating device or ligator can include an Endoloop™-type ligating device which can be provided with a handle operable to contract the ligature loop. The ligating instrument can include the various devices, adapters and instruments disclosed in prior applications Ser. No. 930,320, filed Aug. 17, 1992 and now U.S. Pat. No. 5,334,199, Ser. No. 195,491, filed Feb. 14, 1994 and now U.S. Pat. No. 5,486,186, Ser. No. 452,756, filed May 30,1995 and now U.S. Pat. No. 5,571,120, Ser. No. 531,153, filed Sep. 15, 1995, Ser. No. 08/533,504 filed Sep. 25, 1995 and Ser. No. 08/694,385, filed Aug. 8, 1996, all incorporated herein by reference. The ligature supply can include a single ligature loop or a plurality of ligature loops. The ligature supply can include ligature loops sufficient in number to complete a ligation procedure without withdrawing the ligating instrument or the instrument assembly from the patient's body. Where the ligating instrument, ligating device or ligator has a single ligature loop, a plurality of ligating instruments, ligating devices or ligators can be introduced at the internal operative site for completion of the tubal ligation procedure without withdrawing the instrument assembly from the patient's body. The ligating instrument can have a handle operable with one hand to contract the one or more ligature loops and to perform other functions depending upon the design of the ligating instrument, such as the function of deploying ligature loops of the ligating instrument in sequence and cutting the ligature material proximally of ligatures formed with the ligature loops. Various handle structures for the ligating instruments are disclosed in the prior patents and applications incorporated herein by reference. The ligature material can be absorbable, non-absorbable and/or stretchable in accordance with the procedure to be performed. The ligature loops can include various knotting elements including knots formed by tying the ligature material as well as other knotting elements such as those described in the patents and applications incorporated herein by reference.

The grasping instrument and the ligating instrument can be arranged in many various ways within the passage defining member, such as side by side and concentrically. The instrument assemblies can be utilized in single port and multiple port endoscopic procedures as well as non-endoscopic and mini-lap procedures. For example, the endoscope and grasping instrument can be introduced through a first port and the ligating instrument can be introduced through a second port; the endoscope can be introduced through a first port and the grasping instrument and ligating instrument can be introduced through a second port; the endoscope and ligating instrument can be introduced through a first port and the grasping instrument can be introduced through a second port; and the endoscope, the grasping instrument and the ligating instrument can be introduced through first, second and third ports, respectively. In addition, separate instruments, such as a separate cutting instrument for cutting the anatomical tissue and/or the ligature material, can be introduced through their own ports or through the same port as the endoscope, the grasping instrument and/or the ligating instrument. The endoscope, grasping instrument and ligating instrument can be introduced at the internal operative site through one or more sleeves or cannulas providing communication with the internal operative site from externally thereof. The endoscope, the grasping instrument and/or the ligating instrument can be designed to allow fluid flow therethrough and/or to allow instruments to be introduced therethrough, such as a needle for administering anesthetic agents. The barrel and/or the endoscope can be provided with additional channels for supplying medicaments and/or irrigating fluids, for aspirating fluids and/or for introducing additional instruments.

The endoscope, the grasping instrument and/or the ligating instrument can be withdrawn from the body separately, individually or simultaneously and together as one or more units. The endoscope, the grasping instrument and the ligating instrument can all be longitudinally movable relative to the barrel. The grasping instrument and/or the ligating instrument can be longitudinally movable relative to the endoscope and/or relative to one another. The instruments can be utilized to transmit electrical energy for coagulation or cautery and to transmit laser, cryoenergy and ultrasound. Instrument assemblies for use in the methods of the present invention are disclosed in co-pending patent application entitled "Instrument Assemblies For Performing Anatomical Tissue Ligation" and incorporated herein by reference.

The methods of tubal ligation utilizing the instrument assemblies can be performed endoscopically, non-endoscopically or as mini-lap procedures. In endoscopic procedures, the number of ports utilized will depend on whether instruments used in the procedure are to be introduced through a single port or multiple ports. The instruments used in endoscopic procedures will typically have their distal ends disposed at the operative site and their proximal ends disposed externally of the operative site.

Inasmuch as the present invention is subject to various modifications and changes in detail, the above description of the preferred embodiments is intended to be exemplary only and not limiting.

What is claimed is:

1. A method of endoscopic tubal ligation comprising the steps of introducing a distal end of an instrument assembly at an internal operative site in a patient's body through a small size port providing communication with the internal operative site from externally thereof with a proximal end of the instrument assembly disposed externally of the operative site;

visualizing the internal operative site with an endoscope from externally of the internal operative site;

grasping an anatomical tubular structure at the internal operative site with a grasping member of the instrument assembly disposed at the distal end;

manipulating the grasping member from externally of the internal operative site to draw the anatomical tubular structure into a loop formation through a contractible ligature loop of filamentous ligature material of the instrument assembly disposed externally of the distal end;

contracting the ligature loop around the loop formation of the anatomical tubular structure, from externally of the internal operative sites to form a ligature while the anatomical tubular structure remains grasped by the grasping member;

cutting a segment of the loop formation proximally of the ligature with a cutting member carried by the grasping member;

capturing the cut segment within the cutting member; and withdrawing the grasping member from the patient's body to retrieve the cut segment externally of the patient's body.

2. A method of endoscopic tubal ligation comprising the steps of introducing a distal end of an instrument assembly at an internal operative site in a patient's body through a small size port providing communication with the internal operative site from externally thereof with a proximal end of the instrument assembly disposed externally of the operative site, said step of introducing including introducing a distal end of an endoscope at the internal operative site through the same port as the instrument assembly;

visualizing the internal operative site with the endoscope from externally of the internal operative site;

grasping an anatomical tubular structure at the internal operative site with a grasping member of the instrument assembly disposed at the distal end;

manipulating the grasping member from externally of the internal operative site to draw the anatomical tubular structure into a loop formation through a contractible ligature loop of filamentous ligature material of the instrument assembly disposed externally of the distal end; and contracting the ligature loop around the loop formation of the anatomical tubular structure, from externally of the internal operative site, to form a ligature without withdrawing the instrument assembly from the internal operative site.

3. A method of endoscopic tubal ligation comprising the steps of introducing a distal end of an instrument assembly at an internal operative site in a patient's body through a small size port providing communication with the internal operative site from externally thereof with a proximal end of the instrument assembly disposed externally of the operative site;

visualizing the internal operative site with an endoscope from externally of the internal operative site;

grasping an anatomical tubular structure at the internal operative site with a grasping member of the instrument assembly disposed at the distal end, said step of grasping including grasping the anatomical tubular structure between a pair of grasping members disposed at the distal end of the instrument assembly;

manipulating the grasping members from externally of the internal operative site to draw the anatomical tubular structure into a loop formation through a contractible ligature loop of filamentous ligature material of the instrument assembly disposed externally of the distal end; and contracting the ligature loop around the loop formation of the anatomical tubular structure, from externally of the internal operative site, to form a ligature without withdrawing the instrument assembly from the internal operative site.

4. A method of endoscopic tubal ligation as recited in claim 3 wherein said step of grasping includes moving the grasping members between an open position to receive the anatomical tubular structure between the grasping members and a closed position to capture the anatomical tubular structure between the grasping members.

5. A method of endoscopic tubal ligation as recited in claim 4 wherein said step of grasping includes receiving the anatomical tubular structure between the grasping members to extend transverse to a longitudinal axis of the instrument assembly.

6. A method of endoscopic tubal ligation as recited in claim 5 wherein said step of manipulating includes moving the grasping members longitudinally, proximally relative to the ligature loop.

7. A method of endoscopic tubal ligation as recited in claim 5 wherein said step of manipulating includes moving the ligature loop longitudinally, distally relative to the grasping members.

8. A method of endoscopic tubal ligation as recited in claim 5 wherein said step of manipulating includes moving the grasping members and the ligature loop longitudinally relative to one another.

9. A method of endoscopic tubal ligation comprising the steps of introducing a distal end of an endoscope, a distal end of a grasping instrument and a distal end of a ligating instrument at an internal operative site in a patient's body through a single, small size port providing communication with the internal operative site from externally thereof with a proximal end of the endoscope, a proximal end of the grasping instrument and a proximal end of the ligating instrument disposed externally of the internal operative site;

visualizing the internal operative site, from externally thereof, with the endoscope;

grasping an anatomical tubular structure at the internal operative site with a grasping member at the distal end of the grasping instrument;

drawing the anatomical tubular structure into a loop formation;

positioning a contractible ligature loop of filamentous ligature material carried by the ligating instrument and disposed externally of the distal end of the ligating instrument around the loop formation; and contracting the ligature loop, from the proximal end of the ligating instrument, around the loop formation to form a ligature.

10. A method of endoscopic tubal ligation as recited in claim 9 wherein the ligature loop includes a length of filamentous ligature material, a loop segment of the length of filamentous ligature material and a knotting element slidable along the length of filamentous ligature material and said step of contracting includes moving the knotting element along the length of filamentous ligature material in the direction of the loop segment to contract the loop segment around the loop formation of the anatomical tubular structure to form the ligature.

11. A method of endoscopic tubal ligation as recited in claim 10 and further including, subsequent to said step of contracting, the step of cutting the length of filamentous ligature material proximally of the ligature with a cutting blade of the ligating instrument.

12. A method of endoscopic tubal ligation as recited in claim 11 and further including, subsequent to said step of cutting, the step of deploying another ligature loop of filamentous ligature material of the ligating instrument externally of the distal end of the ligating instrument for use in forming another ligature without withdrawing the ligating instrument from the internal operative site.

13. A method of endoscopic tubal ligation as recited in claim 9 wherein the ligature loop includes a length of filamentous ligature material, a loop segment of the length of filamentous ligature material and a knotting element carried by the length of filamentous ligature material and said step of contracting includes the step of pulling the length of filamentous ligature material proximally relative to the knotting element.

14. A method of endoscopic tubal ligation as recited in claim 9 and further including, subsequent to said step of contracting, the step of cutting the loop formation proximally of the ligature.

15. A method of endoscopic tubal ligation as recited in claim 14 wherein said step of cutting includes cutting the loop formation with a cutting member of the grasping instrument.

16. A method of endoscopic tubal ligation as recited in claim 15 wherein said step of cutting includes severing the loop formation.

17. A method of endoscopic tubal ligation as recited in claim 15 wherein said step of cutting includes collecting a sample of the loop formation for removal from the body.

18. A method of endoscopic tubal ligation comprising the steps of introducing an endoscope through a small size port in the abdominal cavity wall to position a distal end of the endoscope in the abdominal cavity and a proximal end of the endoscope externally of the abdominal cavity to provide visualization of the abdominal cavity from externally thereof;

introducing a ligating instrument in the abdominal cavity through a small size port in the abdominal cavity wall to position a contractible ligature loop of filamentous ligature material of the ligating instrument in the abdominal cavity and a proximal end of the ligating instrument externally of the abdominal cavity;

introducing a grasping instrument in the abdominal cavity through a small size port in the abdominal cavity wall to position a distal end of the grasping instrument to grasp a Fallopian tube in the abdominal cavity and a proximal end of the grasping instrument externally of the abdominal cavity;

drawing the Fallopian tube into a loop formation through the ligature loop with the grasping instrument from externally of the abdominal cavity;

contracting the ligature loop around the loop formation with the ligating instrument from externally of the abdominal cavity to form a ligature;

cutting a segment of the loop formation proximally of the ligature with a cutting member of the grasping instrument:

retrieving the cut segment externally of the patient's body;

repeating said drawing, said contracting, said cutting and said retrieving steps on the other Fallopian tube; and performing an examination on the cut segments to confirm that the cut segments were taken from the Fallopian tubes.

19. A method of endoscopic tubal ligation comprising the steps of introducing an endoscope through a small size port in the abdominal cavity wall to position a distal end of the endoscope in the abdominal cavity and a proximal end of the endoscope externally of the abdominal cavity to provide visualization of the abdominal cavity from externally thereof;

introducing a ligating instrument in the abdominal cavity through a small size port in the abdominal cavity wall to position a contractible ligature loop of filamentous ligature material of the ligating instrument in the abdominal cavity and a proximal end of the ligating instrument externally of the abdominal cavity;

introducing a grasping instrument in the abdominal cavity through a small size port in the abdominal cavity wall to position a distal end of the grasping instrument to grasp a Fallopian tube in the abdominal cavity and a proximal end of the grasping instrument externally of the abdominal cavity;

drawing the Fallopian tube into a loop formation through the ligature loop with the grasping instrument from externally of the abdominal cavity;

contracting the ligature loop around the loop formation with the ligating instrument from externally of the abdominal cavity to form a ligature;

cutting a segment of the loop formation proximally of the ligature with a cutting member introduced in the abdominal cavity through a small size port;

repeating said drawing, said contracting and said cutting steps on the other Fallopian tube:

withdrawing the cut segments from the patient's body; and examining the cut segments to confirm that the cut segments were taken from the Fallopian tubes.

20. A method of endoscopic tubal ligation as recited in claim 19 and further including, after said step of cutting, the step of withdrawing the cut segment from the abdominal cavity.

21. A method of endoscopic tubal ligation as recited in claim 20 and further including, after said step of withdrawing, the step of performing a biopsy on the cut segment.

22. A method of endoscopic tubal ligation as recited in claim 21 wherein said step of introducing the grasping instrument includes introducing the cutting member in the abdominal cavity along with the grasping instrument.

23. A method of endoscopic tubal ligation as recited in claim 19 wherein said steps of introducing include introducing the endoscope through a first port and introducing the ligating instrument and the grasping instrument through a second port.

24. A method of endoscopic tubal ligation comprising the steps of introducing an endoscope through a small size port in the abdominal cavity wall to position a distal end of the endoscope in the abdominal cavity and a proximal end of the endoscope externally of the abdominal cavity to provide visualization of the abdominal cavity from externally thereof;

introducing a ligating instrument in the abdominal cavity through a small size port in the abdominal cavity wall to position a contractible ligature loop of filamentous ligature material of the ligating instrument in the abdominal cavity and a proximal end of the ligating instrument externally of the abdominal cavity;

introducing a grasping instrument in the abdominal cavity through a small size port in the abdominal cavity wall to position a distal end of the grasping instrument to grasp a Fallopian tube in the abdominal cavity and a proximal end of the grasping instrument externally of the abdominal cavity, said steps of introducing including introducing each of the endoscope, the ligating instrument and the grasping instrument through a different small size port;

drawing the Fallopian tube into a loop formation through the ligature loop with the grasping instrument from externally of the abdominal cavity;

contracting the ligature loop around the loop formation with the ligating instrument from externally of the abdominal cavity to form a ligature; and repeating said drawing and contracting steps on the other Fallopian tube.

25. A method of endoscopic tubal ligation comprising the steps of introducing an endoscope through a small size port in the abdominal cavity wall to position a distal end of the endoscope in the abdominal cavity and a proximal end of the endoscope externally of the abdominal cavity to provide visualization of the abdominal cavity from externally thereof;

introducing a ligating instrument in the abdominal cavity through a small size port in the abdominal cavity wall to position a contractible ligature loop of filamentous ligature material of the ligating instrument in the abdominal cavity and a proximal end of the ligating instrument externally of the abdominal cavity;

introducing a grasping instrument in the abdominal cavity through a small size port in the abdominal cavity wall to position a distal end of the grasping instrument to grasp a Fallopian tube in the abdominal cavity and a proximal end of the grasping instrument externally of the abdominal cavity, said steps of introducing including introducing the endoscope and the grasping instrument through a first small size port and introducing the ligating instrument through a second small size port;

drawing the Fallopian tube into a loop formation through the ligature loop with the grasping instrument from externally of the abdominal cavity;

contracting the ligature loop around the loop formation with the ligating instrument from externally of the abdominal cavity to form a ligature; and repeating said drawing and contracting steps on the other Fallopian tube.

26. A method of endoscopic tubal ligation comprising the steps of introducing an endoscope through a small size port in the abdominal cavity wall to position a distal end of the endoscope in the abdominal cavity and a proximal end of the endoscope eternally of the abdominal cavity to provide visualization of the abdominal cavity from externally thereof;

introducing a ligating instrument in the abdominal cavity through a small size port in the abdominal cavity wall to position a contractible ligature loop of filamentous ligature material of the ligating instrument in the abdominal cavity and a proximal end of the ligating instrument externally of the abdominal cavity;

introducing a grasping instrument in the abdominal cavity through a small size port in the abdominal cavity wall to position a distal end of the grasping instrument to grasp a Fallopian tube in the abdominal cavity and a proximal end of the grasping instrument eternally of the abdominal cavity, said steps of introducing including introducing the endoscope and the ligating instrument through a first small size port and introducing the grasping instrument through a second small size port;

drawing the Fallopian tube into a loop formation through the ligature loop with the grasping instrument from externally of the abdominal cavity;

contracting the ligature loop around the loop formation with the ligating instrument from externally of the abdominal cavity to form a ligature; and repeating said drawing and contracting steps on the other Fallopian tube.

\* \* \* \* \*